US009598712B2

(12) United States Patent
Crowe et al.

(10) Patent No.: US 9,598,712 B2
(45) Date of Patent: Mar. 21, 2017

(54) CHEMICAL PROCESS FOR PREPARING SPIROINDOLONES AND INTERMEDIATES THEREOF

(71) Applicants: Michael Crowe, Redwood City, CA (US); Michael Foulkes, Redwood City, CA (US); Giancarlo Francese, Basel (CH); Dominique Grimler, Basel (CH); Ernst Kuesters, Basel (CH); Kurt Laumen, Basel (CH); Yunzhong Li, Changshu (CN); Changxue Lin, Changshu (CN); Jovana Nazor, Redwood City, CA (US); Thomas Ruch, Basel (CH); Derek Smith, Redwood City, CA (US); Shiwei Song, Redwood City, CA (US); Shangjun Teng, Changshu (CN)

(72) Inventors: Michael Crowe, Redwood City, CA (US); Michael Foulkes, Redwood City, CA (US); Giancarlo Francese, Basel (CH); Dominique Grimler, Basel (CH); Ernst Kuesters, Basel (CH); Kurt Laumen, Basel (CH); Yunzhong Li, Changshu (CN); Changxue Lin, Changshu (CN); Jovana Nazor, Redwood City, CA (US); Thomas Ruch, Basel (CH); Derek Smith, Redwood City, CA (US); Shiwei Song, Redwood City, CA (US); Shangjun Teng, Changshu (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/384,233

(22) PCT Filed: Mar. 22, 2013

(86) PCT No.: PCT/EP2013/056170
§ 371 (c)(1),
(2) Date: Sep. 10, 2014

(87) PCT Pub. No.: WO2013/139987
PCT Pub. Date: Sep. 26, 2013

(65) Prior Publication Data
US 2015/0045562 A1  Feb. 12, 2015

(30) Foreign Application Priority Data
Mar. 23, 2012 (WO) ................ PCT/CN2012/000359

(51) Int. Cl.
C07D 209/12 (2006.01)
C07D 209/16 (2006.01)
C12P 17/10 (2006.01)
C07D 405/06 (2006.01)
C07D 471/20 (2006.01)
C07D 209/14 (2006.01)
C07D 209/34 (2006.01)
C12N 9/10 (2006.01)
C07D 209/38 (2006.01)

(52) U.S. Cl.
CPC ............ *C12P 17/10* (2013.01); *C07D 209/12* (2013.01); *C07D 209/14* (2013.01); *C07D 209/34* (2013.01); *C07D 209/38* (2013.01); *C07D 405/06* (2013.01); *C07D 471/20* (2013.01); *C12N 9/1096* (2013.01); *Y02P 20/52* (2015.11)

(58) Field of Classification Search
CPC .. C07D 403/06; C07D 209/16; C07D 405/06; C07D 409/06; C07D 209/12
USPC .......................... 548/468, 491, 485; 435/121
See application file for complete search history.

(56) References Cited

U.S. PATENT DOCUMENTS

| 3,183,170 A | 5/1965 | Kitai et al |
| 3,282,959 A | 11/1966 | John et al. |
| 4,073,795 A | 2/1978 | Batcho et al. |
| 4,859,591 A | 8/1989 | Walter et al. |
| 7,541,091 B2 | 6/2009 | Sisson et al. |
| 9,139,821 B2 * | 9/2015 | Nazor .................. C12N 9/1096 |

FOREIGN PATENT DOCUMENTS

| AT | 507050 | 1/2010 |
| EP | 0036741 | 9/1981 |
| EP | 0120208 | 10/1984 |
| EP | 0135846 | 4/1985 |
| GB | 974895 | 11/1964 |
| WO | 8701727 A1 | 3/1987 |
| WO | 2009132921 | 11/2009 |
| WO | WO 2009132921 A1 * | 11/2009 .......... C07D 471/20 |
| WO | 2010081053 | 7/2010 |

(Continued)

OTHER PUBLICATIONS

Nichols D. E et al., " Synthesis and serotonin receptor affinities of a series of enantiomers of alpha-methyltryptamhes: evidence for the binding conformation of tryptamines at serotonin S-HT1B receptors", J. Med. Chem., 31 (7), pp. 1406-1412, XP001149357 1988.

(Continued)

*Primary Examiner* — Alicia L Otton
*Assistant Examiner* — Sagar Patel
(74) *Attorney, Agent, or Firm* — Daniel Woods

(57) ABSTRACT

The present invention relates to processes and intermediates useful for the manufacture of spiroindolone compounds such as (1'R,3'S)-5,7'-dichloro-6'-fluoro-3'-methyl-2',3',4',9'-tetrahydrospiro[indoline-3,1'-pyrido[3,4-b]indol]-2-one and salts and hydrates and solvates thereof.

7 Claims, No Drawings

(56) References Cited

FOREIGN PATENT DOCUMENTS

WO    2012007548    1/2012

OTHER PUBLICATIONS

Iwao Tabushi et al., "A-(modified B6)-B-[ .omega.-amino(ethylamino)]beta.-cyclodextrin as an artificial B6 enzyme for chiral aminotransfer reaction", J. Am. Chem. Soc., 1 07(19), pp. 5545-5546, XP055064105, 1985.
Baldwin J. E. et al., "Application of *E. coli* aspartate transaminase to amino acid synthesis"; Tetrahedron Lett., (32) pp. 3745-19873746, XP002507159, 1987.
Asano Y. et al, "High Yield Synthesis of L-Amino Acids by Phenylalanine Dehydrogenase From Sporosarcina Ureae", Agric. Biol. Chem., 51 (7), p. 2035-2036, XP009025113, 1987.

\* cited by examiner

CHEMICAL PROCESS FOR PREPARING SPIROINDOLONES AND INTERMEDIATES THEREOF

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "PAT055051_seql2.txt", a creation date of Mar. 22, 2013, and a size of 447 kilobytes. The Sequence Listing filed via EFS-Web is part of the specification and is incorporated in its entirety by reference herein.

PRIOR ART (1'R,3'S)-5,7'-dichloro-6'-fluoro-3'-methyl-2',3',4',9'-tetrahydrospiro[indoline-3,1'-pyrido[3,4-b]indol]-2-one (eg. a compound of formula (IV), which comprises a spiroindolone moiety) and a 6-steps synthetic method for preparing, including known chiral amine intermediate compound (IIA) are known (WO 2009/132921):

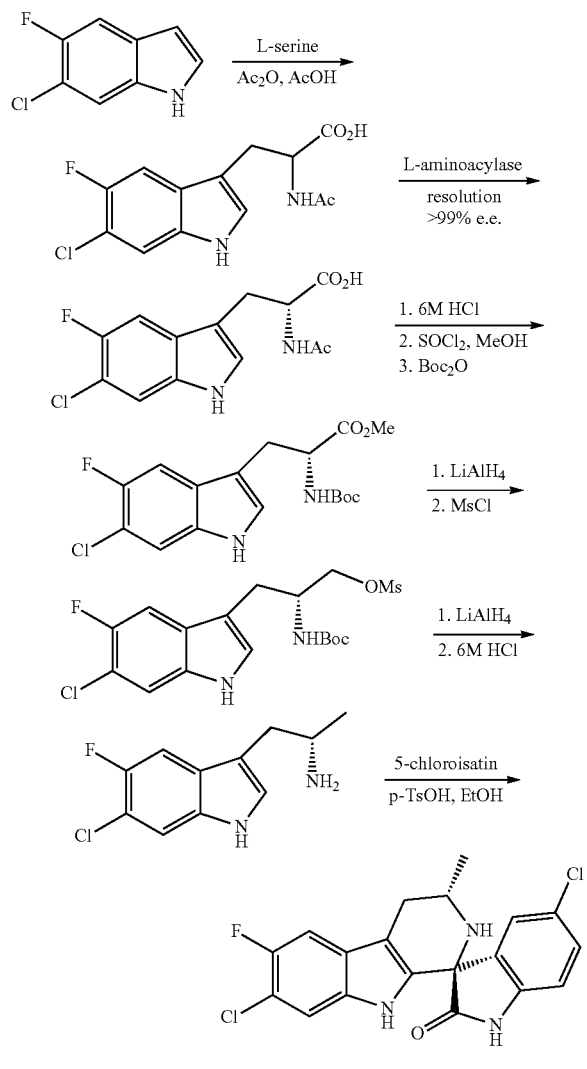

INVENTION

The present invention is directed to an improved method of synthesizing spiroindolone compounds, in particular, (1'R,3'S)-5,7'-dichloro-6'-fluoro-3'-methyl-2',3',4',9'-tetrahydrospiro[indoline-3,1'-pyrido[3,4-b]indol]-2-one, and intermediates used in the improved method.

In a first embodiment, the invention is a process for preparing a compound of formula (II), or a salt or solvate or hydrate thereof,

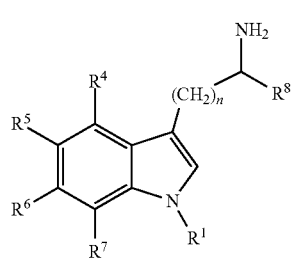

comprising converting a compound of formula (I) to compound of formula (II), or a salt, solvate or hydrate thereof,

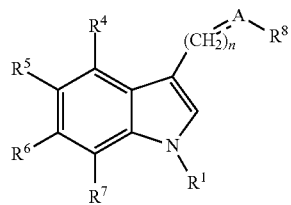

wherein: the dashed line is a bond or absent; A is selected from C=O and C=NH; or when the dashed line is a double bond A-$R^8$ is:

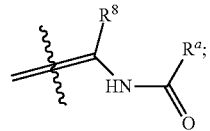

$R^a$ is $C_{1-6}$ alkyl; $R^1$ is H, —$CH_3$,

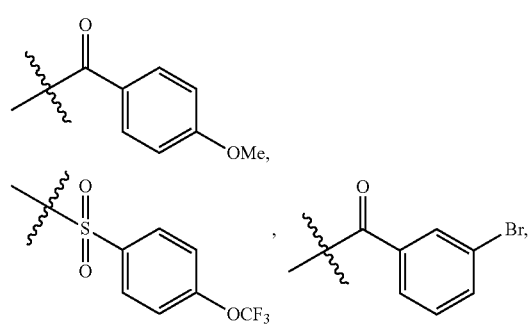

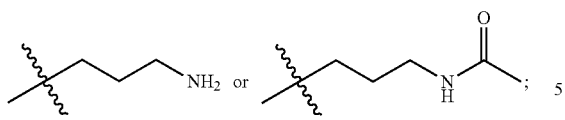

$R^4$ and $R^7$ are each, independently, H or —Cl; $R^5$ is H, —OH, —CH$_3$, —OCH$_3$, —F, —Cl, —CF$_3$ or —CN; $R^6$ is H, —OH, —OCH$_3$, —F or —Cl; $R^8$ is H, —CH$_3$, —CH$_2$CH$_3$, —CH$_2$OH, —CO$_2$H, —CO$_2$CH$_3$, —CO$_2$CH$_2$CH$_3$ or —CF$_3$; and n is 1 or 2.

In a second embodiment, the invention is a process for preparing a compound of formula (IIA) or a salt or hydrate or solvate thereof,

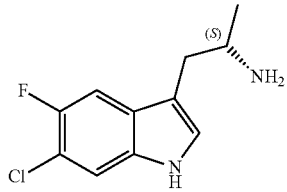

(IIA)

comprising enzymatically transaminating a compound of formula (IA) or a salt or solvate or hydrate thereof,

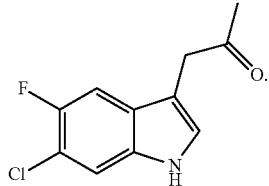

(IA)

to provide the compound of formula (IIA).

In a third embodiment, the invention is a process for preparing a compound of formula (IV), or a salt or hydrate or solvate thereof,

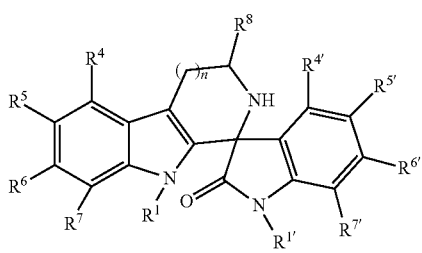

(IV)

comprising, reacting a compound of formula (III), or a salt or hydrate or solvate thereof,

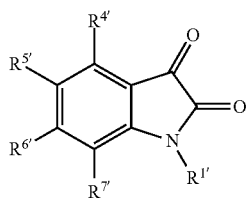

(III)

with a compound of formula (II), or a salt or hydrate or solvate thereof,

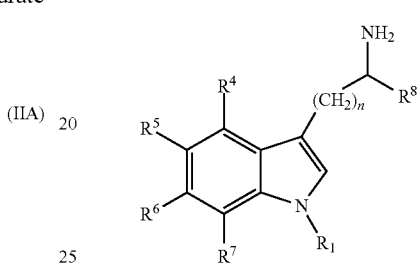

(II)

wherein the compound of formula (II), or a salt or hydrate or solvate thereof, is prepared from a compound of formula (I), or a salt or hydrate or solvate thereof,

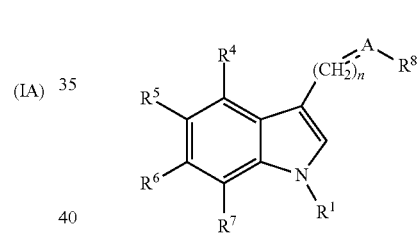

(I)

wherein: the dashed line is a bond or absent; A is selected from C═O and C═NH; or when the dashed line is a double bond A-$R^8$ is:

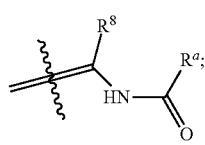

$R^a$ is $C_{1-6}$ alkyl; $R^1$ is $(C_1-C_6)$ alkyl, optionally substituted with an amino, $(C_1-C_6)$ alkyl amino, $(C_1-C_6)$ alkyl di-alkyl amino or $(C_1-C_6)$ alkyl C(O)NH (C1-6) alkyl; $R^4$ and $R^7$ are each, independently. H or halo; $R^5$ and $R^6$ are each, independently hydrogen, halo, hydroxyl, $(C_1-C_6)$ alkyl, trihalo $(C_1)$ alkyl, cyano or $(C_1-C_6)$ alkoxy; $R^8$ is $(C_1-C_6)$ alkyl, optionally substituted with a hydroxyl; n is 1 or 2; $R^1$ is hydrogen or $(C_1-C_6)$alkyl; and $R^{4'}$, $R^{5'}$, $R^{6'}$ and $R^{7'}$, are each, independently hydrogen, halo, hydroxy, amino, alkylamino, dialkylamino, $(C_1-C_6)$alkyl, and $(C_1-C_6)$alkyloxy.

In a fourth embodiment, the invention is a process for preparing a compound of formula (IVA), or a salt or solvate or hydrate thereof,

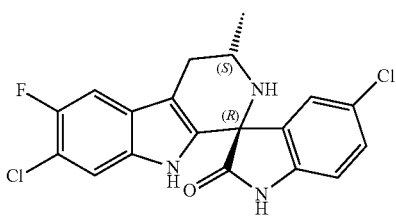

(IVA)

comprising: reacting a compound of formula (IIIA) or a salt or solvate or hydrate thereof,

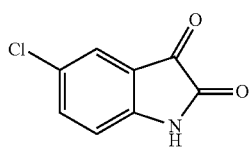

(IIIA)

with a compound of formula (II) or a salt or solvate or hydrate thereof,

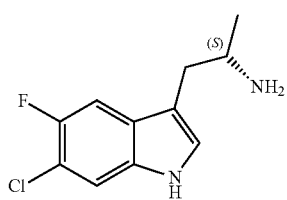

(IIA)

to provide the compound of formula (IVA), or a salt or solvate or hydrate thereof, wherein the compound of formula (IIA) is prepared from the compound of formula (IA), or a salt or hydrate or solvate thereof,

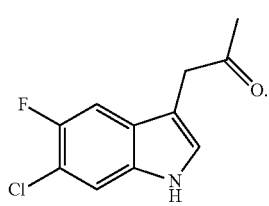

In a fifth embodiment, the invention is a compound of formula (IC):

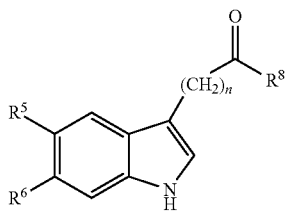

(IC)

wherein: $R^1$ is ($C_1$-$C_6$) alkyl, optionally substituted with an amino, ($C_1$-$C_6$) alkyl amino, ($C_1$-$C_6$) alkyl di-alkyl amino or ($C_1$-$C_6$) alkyl C(O)NH (C1-6) alkyl; $R^5$ and $R^6$ are each, independently hydrogen, halo, hydroxyl, ($C_1$-$C_6$) alkyl, trihalo ($C_1$) alkyl, cyano or ($C_1$-$C_6$) alkoxy; $R^8$ is ($C_1$-$C_6$) alkyl, optionally substituted with a hydroxyl; n is 1 or 2; or a pharmaceutically acceptable salt or hydrate or solvate thereof.

In a sixth embodiment the invention is a compound selected from:

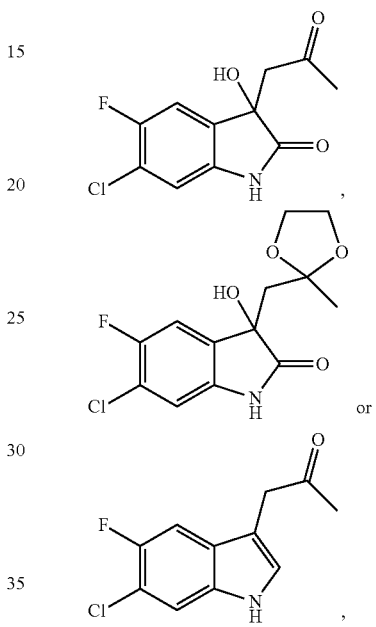

or a pharmaceutically acceptable salt, solvate or hydrate thereof.

FIELD OF THE INVENTION

The invention relates to novel processes a novel process step and a novel intermediate useful for the preparation of spiroindolone compounds useful for the treatment of parasitic diseases comprising e.g. a spiroindolone moiety, such as (1'R,3'S)-5,7'-dichloro-6'-fluoro-3'-methyl-2',3',4',9'-tetrahydrospiro[indoline-3,1'-pyrido[3,4-b]indol]-2-one.

BACKGROUND OF THE INVENTION

The present invention relates to processes for the preparation of spiroindolone compounds, such as (1'R,3'S)-5,7'-dichloro-6'-fluoro-3'-methyl-2',3',4',9'-tetrahydrospiro[indoline-3,1'-pyrido[3,4-b]indol]-2-one.

(1'R, 3'S)-5,7'-dichloro-6'-fluoro-3'-methyl-2',3',4',9'-tetrahydrospiro[indoline-3,1'-pyrido[3,4-b]indol]-2-one is useful in the treatment and/or prevention of infections such as those caused by *Plasmodium falciparum, Plasmodium vivax, Plasmodium malariae, Plasmodium ovale, Trypanosoma cruzi* and parasites of the *Leishmania* genus such as, for example, *Leishmania donovani.*, and it has the following structure:

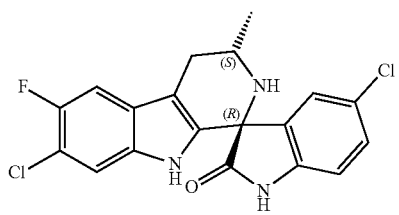

(IVA)

(1'R, 3'S)-5,7'-dichloro-6'-fluoro-3'-methyl-2',3',4',9'-tetrahydrospiro[indoline-3,1'-pyrido[3,4-b]indol]-2-one and a synthesis thereof are described in WO 2009/132921 AI in particular in Example 49 therein.

There is a need to provide new process for the preparation of (1'R, 3'S)-5,7'-dichloro-6'-fluoro-3'-methyl-2',3',4',9'-tetrahydrospiro[indoline-3,1'-pyrido[3,4-b]indol]-2-one in order to improve the overall efficiency of the synthesis to make it suitable for manufacturing. In particular, there is a need to increase the efficiency of synthesizing the chiral amine intermediate (IIA):

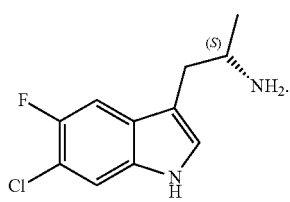

(IIA)

DETAILED DESCRIPTION OF THE INVENTION

The process(es), according to the present invention, for producing spiroindolone compounds, such as compounds according to formula (IV), or salt or hydrate or solvate thereof, and intermediates, as defined herein, are summarized in Scheme 1.

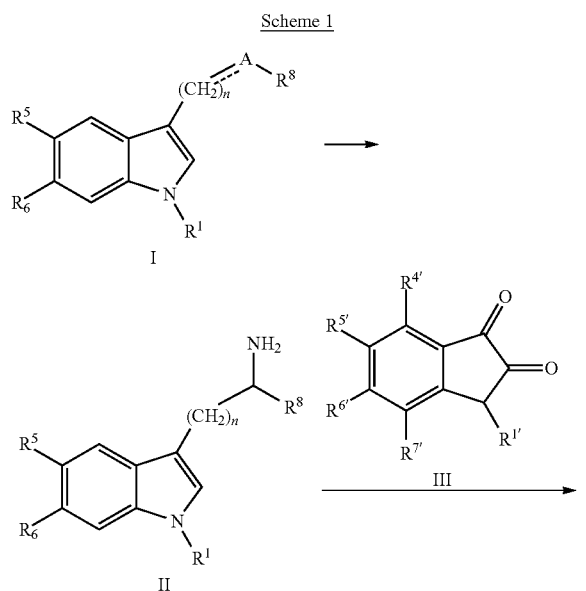

Scheme 1

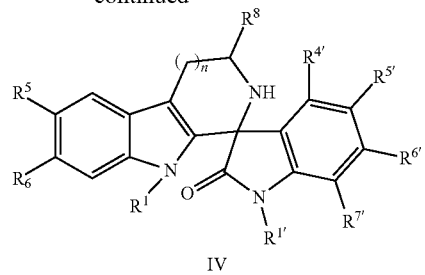

IV

Namely, a compound of formula (I), or salt or hydrate or solvate thereof, is converted into a compound of formula (II), or salt or hydrate or solvate thereof, according to methods 1, 2, 3, 4, 5 or 6 wherein method 1 comprises
a) Enzymatic transamination to convert a compound of formula (I), or salt or hydrate or solvate thereof, into a compound of formula (II), or salt or hydrate or solvate thereof

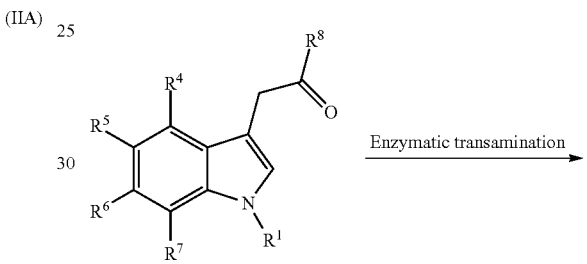

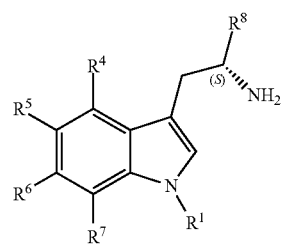

method 2 comprises;
a) Chemical asymmetric catalysis to convert a compound of formula (I), or salt or hydrate or solvate thereof, into a compound of formula (II), or salt thereof;

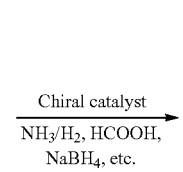

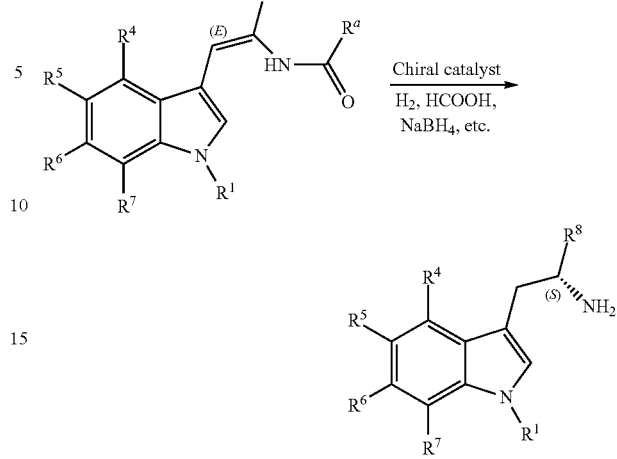
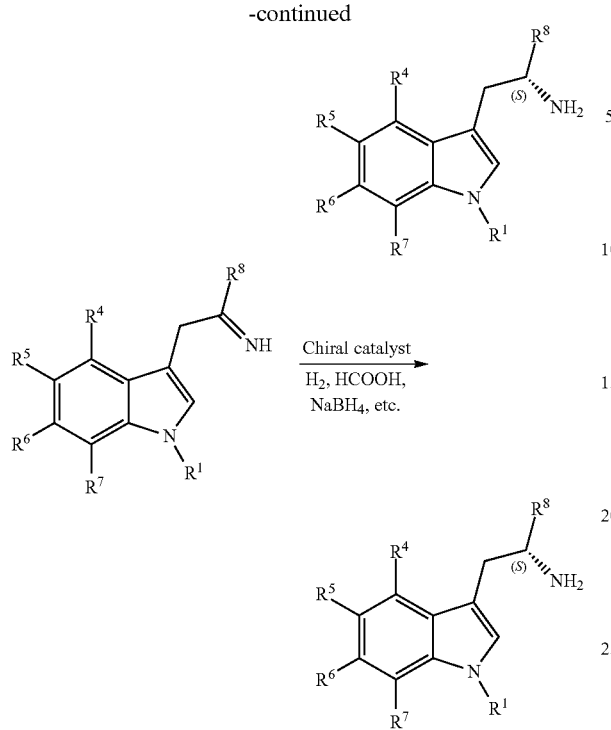
method 3 comprises
a) Chemical asymmetric reduction to convert a compound of formula (I), or salt or hydrate or solvate thereof, into a compound of formula (II), or salt or hydrate or solvate thereof;
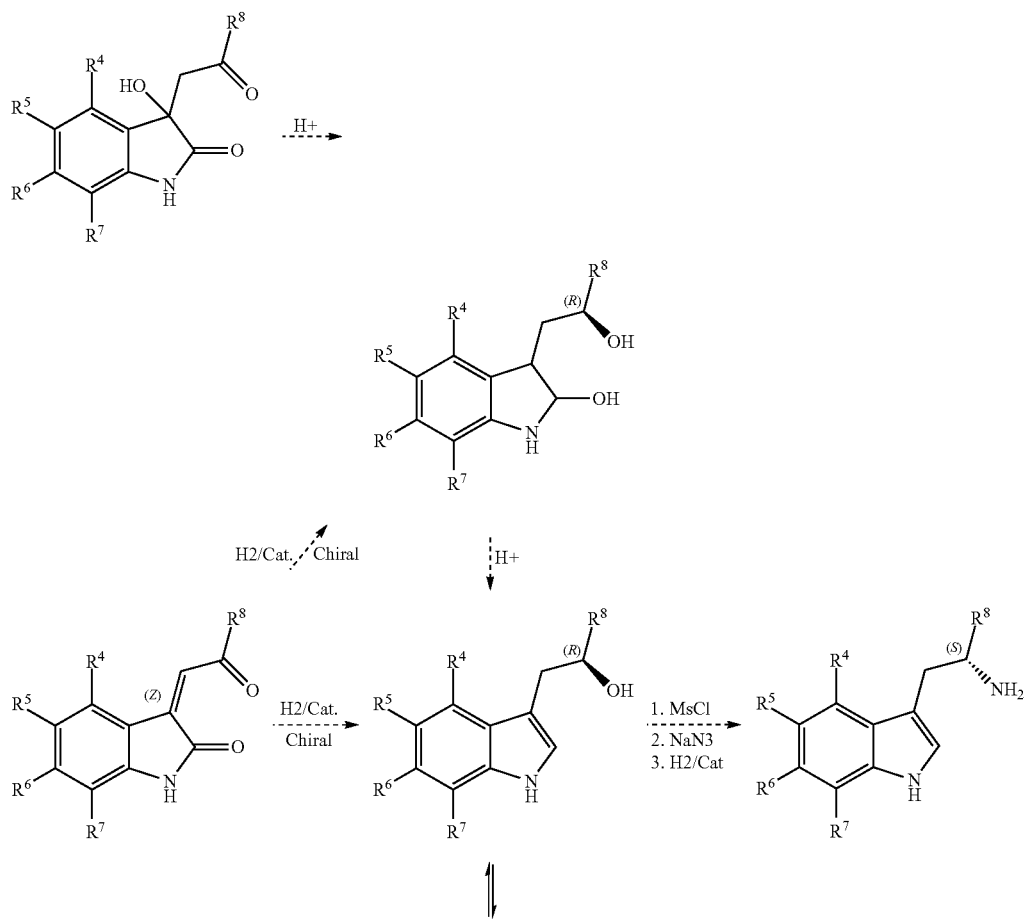

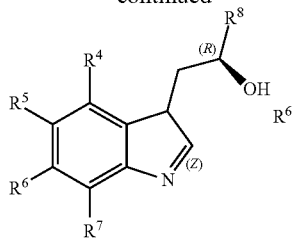

method 4 comprises a) Reduction followed by chiral resolution to convert a compound of formula (I), or salt or hydrate or solvate thereof, into a compound of formula (II), or salt or hydrate or solvate thereof;

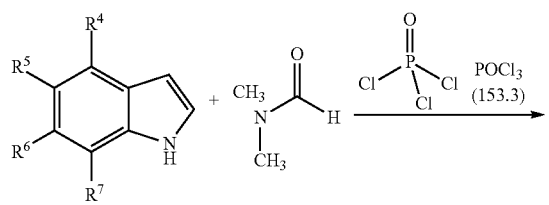

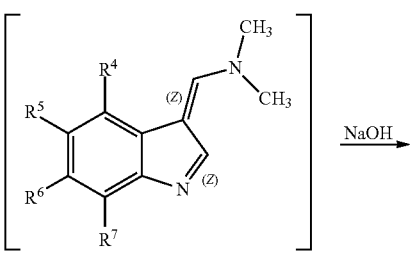

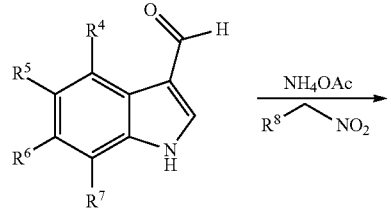

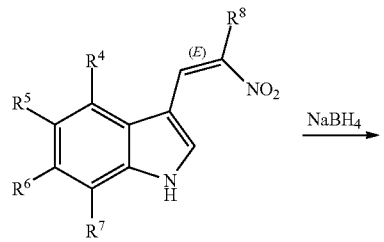

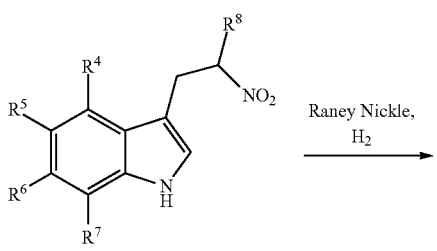

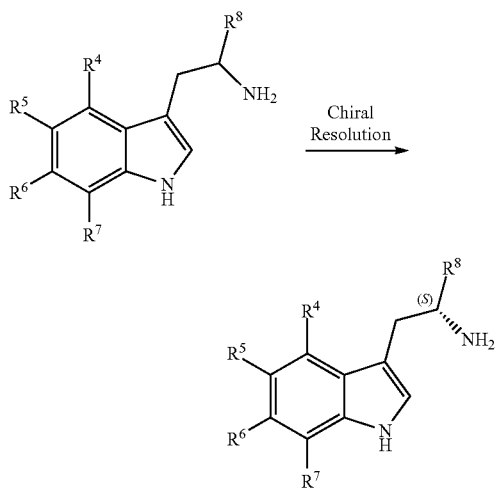

method 5 comprises a) Lipase resolution to convert a racemate of a compound of formula (II), or salt or hydrate or solvate thereof, into a single enantiomer compound of formula (II), or salt or hydrate or solvate thereof;

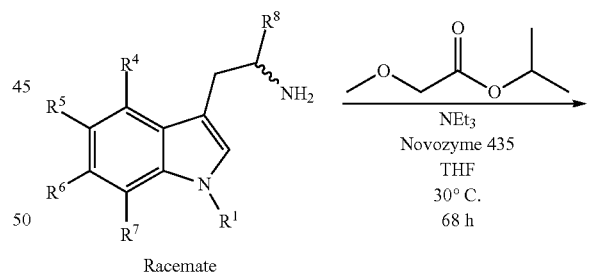

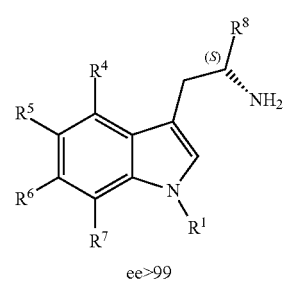

ee>99

-continued

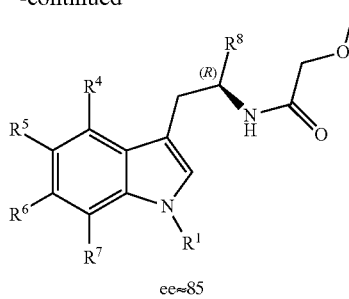

ee≈85

Novozym 435: *Candida antarctica* Lipase B imobilized on an acrylic resin method 6 comprises
a) A combination of two or more of methods 1-5 to convert a compound of formula (I), or salt or hydrate or solvate thereof, into a compound of formula (II), or salt or hydrate or solvate thereof.

A compound of formula (II), or salt thereof, may be converted into a compound formula (IV), or salt thereof, for example, as described in WO 2009/132921 in particular as described in the relevant claims and examples, which are incorporated by reference herein.

The invention specially relates to the processes described in each section. The invention likewise relates, independently, to every single step described in a process sequence within the corresponding section. Therefore, each and every single step of any process, consisting of a sequence of steps, described herein is itself a preferred embodiment of the present invention. Thus, the invention also relates to those embodiments of the process, according to which a compound obtainable as an intermediate in any step of the process is used as a starting material.

The invention likewise relates to novel starting materials which have been specifically developed for the preparation of the compounds according to the invention, to their use and to processes for their preparation.

The invention also relates to intermediates which have been specifically developed for the preparation of the compounds according to the invention, to their use and to processes for their preparation.

It is noted that in the present application usually explanations made in one section are also applicable for other sections, unless otherwise stated. For example, the explanations for the residue $R^1$ in formula (I) given in section A also apply if formula (I) occurs in other sections, such as Section B, unless otherwise stated.

Section A: Preparation of a Compound of Formula (I)

A compound of formula (I), or salt thereof, or hydrate or solvate thereof, may be prepared as described below and/or according to Examples 1-3 contained herein.

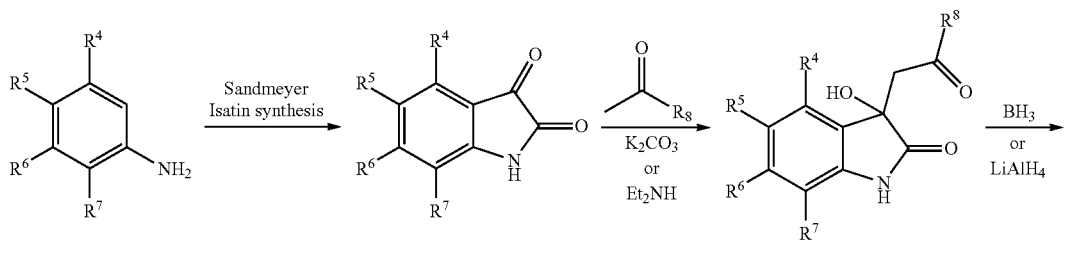

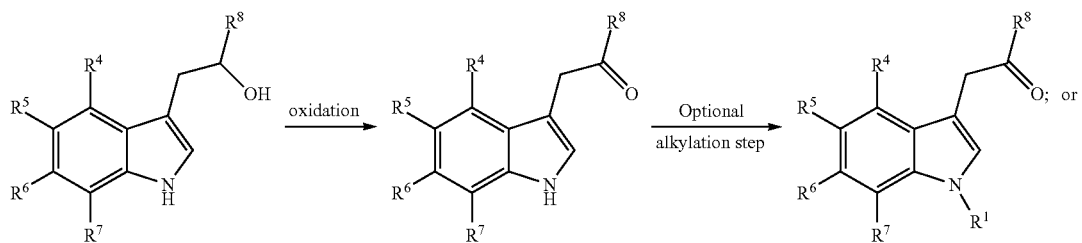

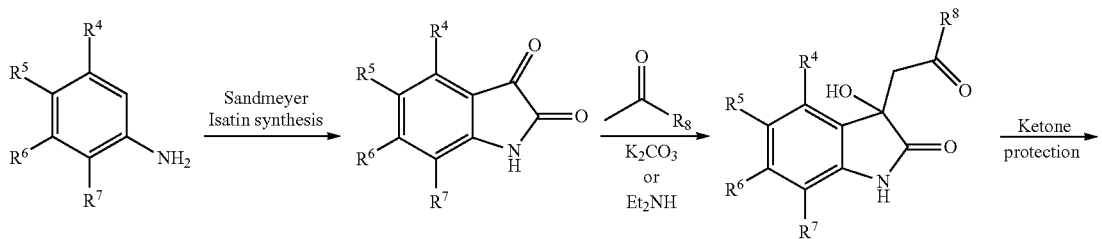

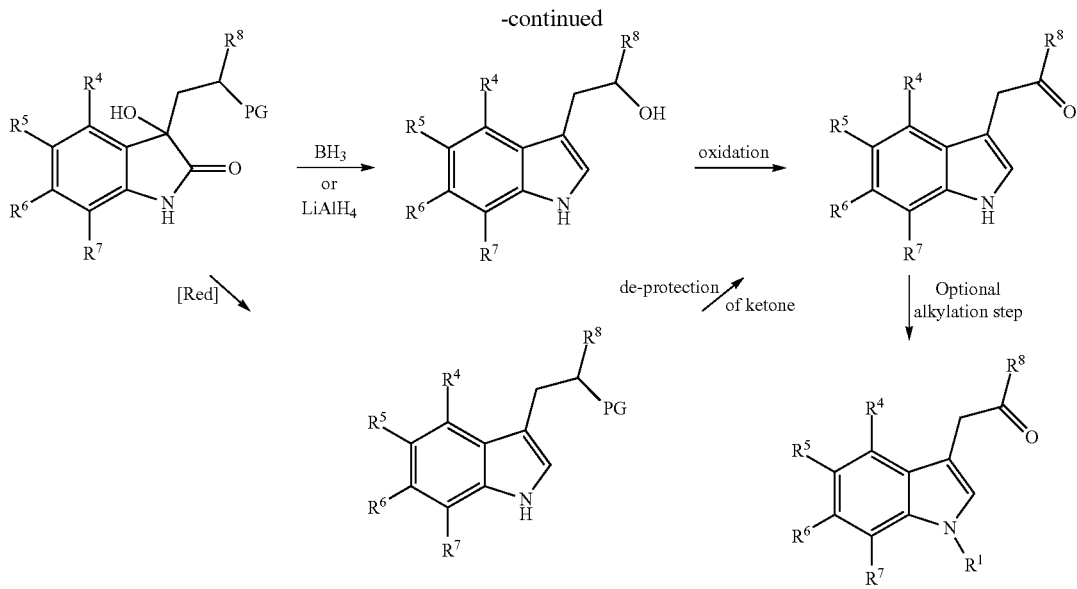

Section B: Conversion of a Compound of Formula (I) into a Compound of Formula (II)

In a first embodiment, the invention is a process for preparing a compound of formula (II), or a salt or solvate or hydrate thereof,

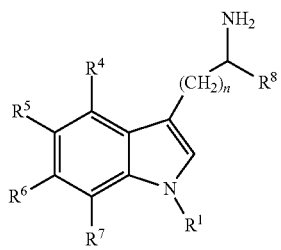

(II)

comprising converting a compound of formula (I) to compound of formula (II), or a salt, solvate or hydrate thereof,

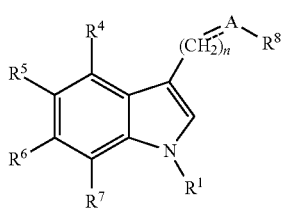

(I)

wherein: the dashed line is a bond or absent; A is selected from C=O and C=NH; or when the dashed line is a double bond A-$R^8$ is:

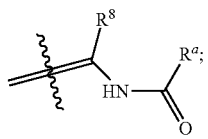

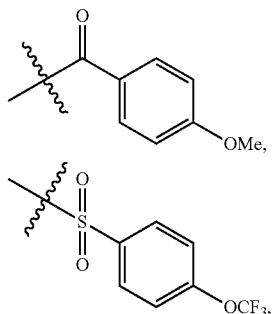

$R^a$ is $C_{1-6}$ alkyl; $R^1$ is H, —$CH_3$,

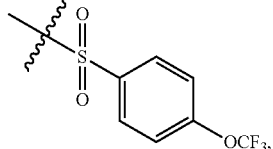

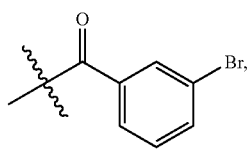

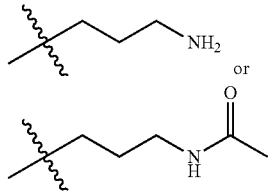

$R^4$ and $R^7$ are each, independently, H or —Cl; $R^5$ is H, —OH, —$CH_3$, —$OCH_3$, —F, —Cl, —$CF_3$ or —CN; $R^6$ is H, —OH, —$OCH_3$, —F or —Cl; $R^8$ is H, —$CH_3$, —$CH_2CH_3$, —$CH_2OH$, —$CO_2H$, —$CO_2CH_3$, —$CO_2CH_2CH_3$ or —$CF_3$, and n is 1 or 2.

In a first alternative embodiment, the invention is a process for converting a compound of formula (I) into a compound of formula (II), wherein, $R^5$ and $R^6$ are fluoro when: $R^8$ is —$CH_3$, and n is 1.

In a second alternative embodiment, the invention is a process for converting a compound of formula (I) into a compound of formula (II), wherein, $R^5$ and $R^6$ are fluoro and chloro, when: $R^8$ is —$CH_3$, and n is 1.

In a third alternative embodiment, the invention is a process for converting a compound of formula (I) into a compound of formula (II), wherein, $R^5$ and $R^6$ are hydrogen when: $R^8$ is —$CH_3$ and n is 1.

In a fourth alternative embodiment, the invention is a process for converting a compound of formula (I) into a compound of formula (II), wherein, $R^5$ is fluoro when: n is 1, and $R^6$ is hydrogen.

In a sixth alternative embodiment, the invention is a process for converting a compound of formula (I) into a compound of formula (II), wherein, the compound of formula (II) is of formula (IIA), or a salt or solvate or hydrate thereof,

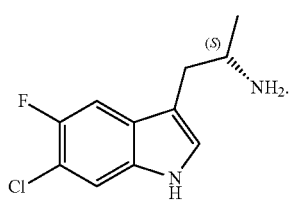

(IIA)

In a seventh alternative embodiment, the invention is a process for converting a compound of formula (I) into a compound of formula (II), wherein, the compound of formula (II) is converted from the compound of formula (I) under a condition selected from enzymatic transamination, chemical asymmetric catalysis, asymmetric reduction and chiral resolution, or a combination of two or more conditions.

In an eighth alternative embodiment, the invention is a process for converting a compound of formula (I) into a compound of formula (II), wherein, A is C=O.

In a ninth alternative embodiment, the invention is a process for converting a compound of formula (I) into a compound of formula (II), wherein, the compound of formula (I) is a compound of formula (IA) or a salt or hydrate or solvate thereof,

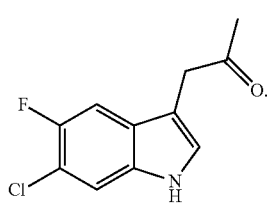

(IA)

In an exemplary embodiment, the enzyme is SEQ ID NO: 134.

In a second embodiment, the invention is a process for preparing a compound of formula (IIA) or a salt or hydrate or solvate thereof,

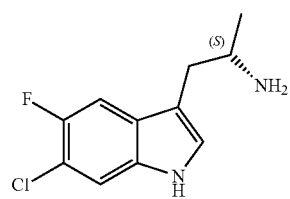

(IIA)

comprising enzymatically transaminating a compound of formula (IA) or a salt or solvate or hydrate thereof,

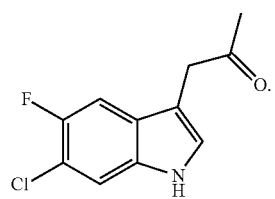

(IA)

to provide the compound of formula (IIA).

Typically, the ketone, compound (I) is dissolved in an organic solvent, e.g. glycol, and added to an aqueous mixture of isopropyl amine HCL and pyridoxalphosphate, followed by the addition of TEA buffer. The pH is then adjusted to neutral with an appropriate base, e.g. NaOH followed by warming and addition of the transaminase. The reaction is allowed to stir at temperature for approximately 24 hrs. The solid chiral amine product (compound of formula (II))) is isolated by means known to one of skill in the art, and/or according to examples 10-12.

In an exemplary embodiment, the enzyme is SEQ ID NO: 134.

Section C: Conversion of a Compound of Formula (Ii) into a Compound of Formula (IV)

In a third embodiment, the invention is a process for preparing a compound of formula (IV), or a salt or hydrate or solvate thereof,

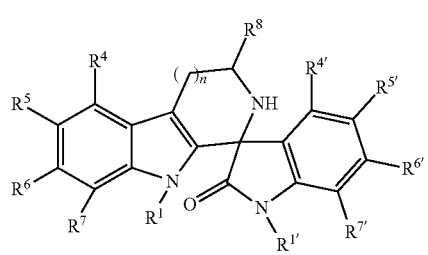

(IV)

comprising, reacting a compound of formula (III), or a salt or hydrate or solvate thereof,

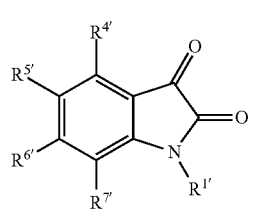

(III)

with a compound of formula (II), or a salt or hydrate or solvate thereof,

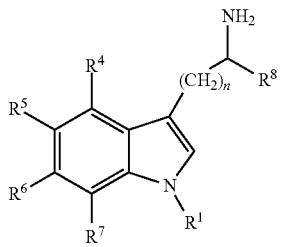
(II)

wherein the compound of formula (II), or a salt or hydrate or solvate thereof, is prepared from a compound of formula (I), or a salt or hydrate or solvate thereof,

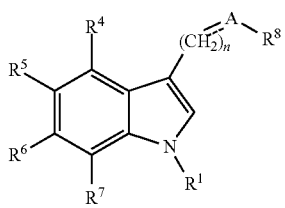
(I)

wherein: the dashed line is a bond or absent; A is selected from C=O and C=NH; or when the dashed line is a double bond A-$R^8$ is:

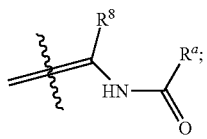

$R^a$ is $C_{1-6}$ alkyl; $R^1$ is $(C_1-C_6)$ alkyl, optionally substituted with an amino, $(C_1-C_6)$ alkyl amino, $(C_1-C_6)$ alkyl di-alkyl amino or $(C_1-C_6)$ alkyl C(O)NH $(C_1-C_6)$ alkyl; $R^4$ and $R^7$ are each, independently. H or halo; $R^5$ and $R^6$ are each, independently hydrogen, halo, hydroxyl, $(C_1-C_6)$ alkyl, trihalo $(C_1)$ alkyl, cyano or $(C_1-C_6)$ alkoxy; $R^8$ is $(C_1-C_6)$ alkyl, optionally substituted with a hydroxyl; n is 1 or 2, $R^{1'}$ is hydrogen or $(C_1-C_6)$alkyl; and $R^{4'}$, $R^{5'}$, $R^{6'}$ and $R^{7'}$, are each, independently hydrogen, halo, hydroxy, amino, alkylamino, dialkylamino, $(C_1-C_6)$alkyl, and $(C_1-C_6)$alkyloxy.

In a tenth alternative embodiment, the invention is a process for preparing a compound of formula (IV) wherein, $R^5$ and $R^6$ are fluoro when: $R^8$ is —$CH_3$, and n is 1.

In an eleventh alternative embodiment, the invention is a process for preparing a compound of formula (IV) wherein, $R^5$ and $R^6$ are fluoro and chloro when: $R^8$ is —$CH_3$, and n is 1.

In a twelve alternative embodiment, the invention is a process for preparing a compound of formula (IV) wherein, $R^5$ and $R^6$ are hydrogen when: $R^8$ is —$CH_3$ and n is 1.

In a fourteenth alternative embodiment, the invention is a process for preparing a compound of formula (IV) wherein, $R^5$ is fluoro when: n is 1, and $R^6$ is hydrogen. $R^1$ is H, —$CH_3$,

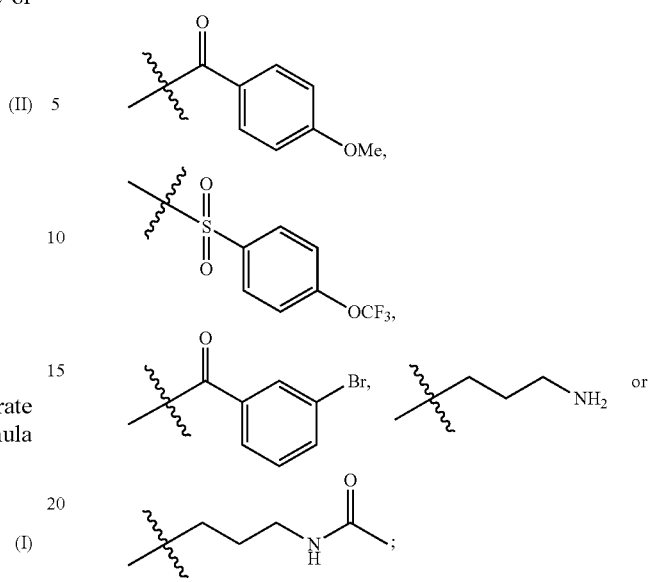

$R^4$ and $R^7$ are each, independently. H or —Cl; $R^5$ is H, —OH, —$CH_3$, —$OCH_3$, —F, —Cl, —$CF_3$ or —CN; $R^6$ is H, —OH, —$OCH_3$, —F or —Cl; $R^8$ is H, —$CH_3$, —$CH_2CH_3$, —$CH_2OH$, —$CO_2H$, —$CO_2CH_3$, —$CO_2CH_2CH_3$ or —$CF_3$; and n is 1 or 2.

In a fifteenth alternative embodiment, the invention is a process for preparing a compound of formula (IV) wherein, the compound of formula (II) is of formula (IIA), or a salt or solvate or hydrate thereof,

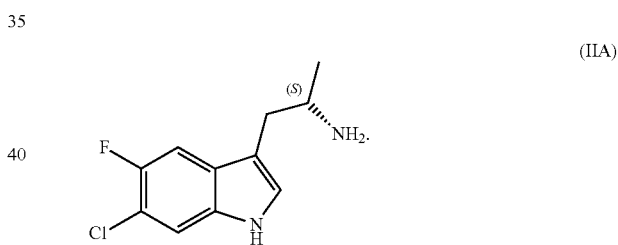
(IIA)

In a sixteenth alternative embodiment, the invention is a process for preparing a compound of formula (IV) wherein, wherein $R^{5'}$ is a halo.

In a seventeenth alternative embodiment, the invention is a process for preparing a compound of formula (IV) wherein, $R^{5'}$ is a chloro, and $R^{1'}$, $R^{4'}$, $R^{6'}$ and $R^{7'}$ are each hydrogen.

In a eighteenth alternative embodiment, the invention is a process for preparing a compound of formula (IV) wherein, the compound of formula (III) is of formula (IIIA), or a salt or hydrate or solvate thereof,

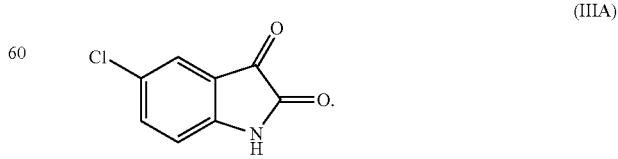
(IIIA)

In an exemplary embodiment, the enzyme is SEQ ID NO: 134.

In a fourth embodiment, the invention is a process for preparing a compound of formula (IVA), or a salt or solvate or hydrate thereof,

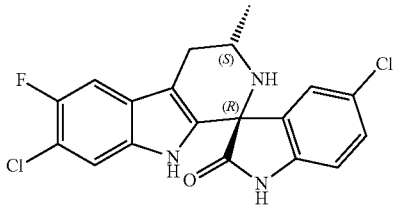
(IVA)

comprising: reacting a compound of formula (IIIA) or a salt or solvate or hydrate thereof,

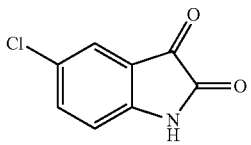
(IIIA)

with a compound of formula (II) or a salt or solvate or hydrate thereof,

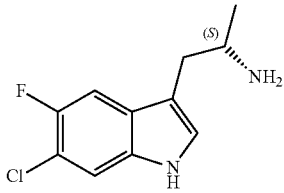
(IIA)

to provide the compound of formula (IVA), or a salt or solvate or hydrate thereof, wherein the compound of formula (IIA) is prepared from the compound of formula (IA), or a salt or hydrate or solvate thereof,

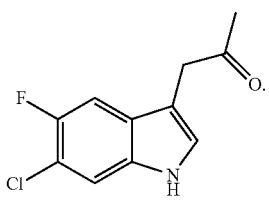

In a nineteenth alternative embodiment, the invention is a process for preparing a compound of formula (IVA) wherein, the compound of formula (IIA) is converted to a salt of formula (IIB):

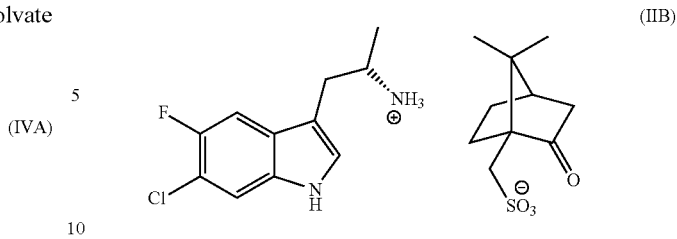
(IIB)

prior to reaction with the compound of formula (IIIA).

In an exemplary embodiment, the enzyme is SEQ ID NO: 134.

In a twentieth alternative embodiment, the invention is a process for preparing a compound of formula (IVA) wherein, the reaction is carried out under basic conditions.

In a twenty-first alternative embodiment, the invention is a process for preparing a compound of formula (IVA) wherein, the reaction is carried out in the presence of triethyl amine.

In a twenty-second alternative embodiment, the invention is a process for preparing a compound of formula (IVA) wherein, the compound of formula (IVA) is isolated as a salt of formula (IVB):

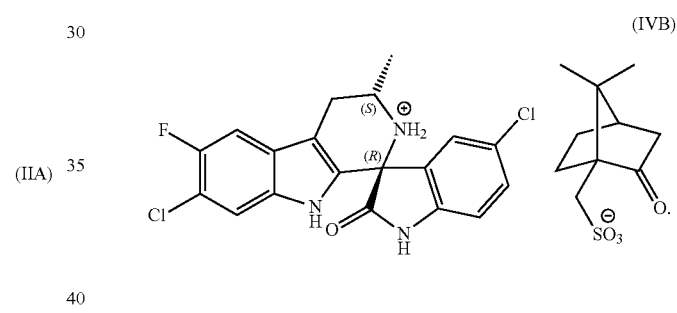
(IVB)

In a twenty-third alternative embodiment, the invention is a process for preparing a compound of formula (IVA) wherein, the salt of formula (IVB) is converted to the compound of formula (IVA) in free base.

In a twenty-fourth alternative embodiment, the invention is a process for preparing a compound of formula (IVA) wherein, the salt of formula (IVB) is converted to the compound of formula (IVA) in free base with sodium carbonate.

In a twenty-fifth alternative embodiment, the invention is a process for preparing a compound of formula (IVA) wherein, the compound of formula (IVA) is a hydrate.

In a twenty-sixth alternative embodiment, the invention is a process for preparing a compound of formula (IVA) wherein, the compound of formula (IVA) is a ½ hydrate.

In a twenty-seventh alternative embodiment, the invention is a process for preparing a compound of formula (IVA) ½ hydrate wherein, the compound of formula (IVA) ½ hydrate is milled after isolation.

Section D: Use of the Novel and Inventive Compounds of Formula (IC)

In a fifth embodiment, the invention is a compound of formula (IC):

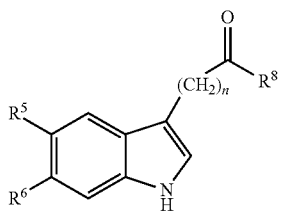
(IC)

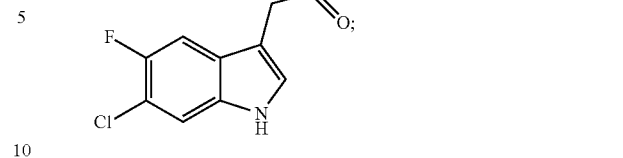
(IA)

wherein: $R^1$ is $(C_1-C_6)$ alkyl, optionally substituted with an amino, $(C_1-C_6)$ alkyl amino, $(C_1-C_6)$ alkyl di-alkyl amino or $(C_1-C_6)$ alkyl C(O)NH (C1-6) alkyl; $R^5$ and $R^6$ are each, independently hydrogen, halo, hydroxyl, $(C_1-C_6)$ alkyl, trihalo $(C_1)$ alkyl, cyano or $(C_1-C_6)$ alkoxy; $R^8$ is $(C_1-C_6)$ alkyl, optionally substituted with a hydroxyl; n is 1 or 2; or a pharmaceutically acceptable salt or hydrate or solvate thereof.

In a twenty-eighth alternative embodiment, the invention is a compound of formula (IC) wherein, $R^5$ and $R^6$ are fluoro when: $R^8$ is —$CH_3$, and n is 1.

In a twenty-ninth alternative embodiment, the invention is a compound of formula (IC) wherein, $R^5$ and $R^6$ are fluoro and chloro, when: $R^8$ is —$CH_3$, and n is 1.

In a thirtieth alternative embodiment, the invention is a compound of formula (IC) wherein, $R^5$ and $R^6$ are hydrogen when: $R^8$ is —$CH_3$ and n is 1.

In a thirty-first alternative embodiment, the invention is a compound of formula (IC) wherein, $R^5$ is fluoro when: n is 1, and $R^6$ is hydrogen.

In a thirty-second alternative embodiment, the invention is a compound of formula (IC) wherein, $R^1$ is H, —$CH_3$,

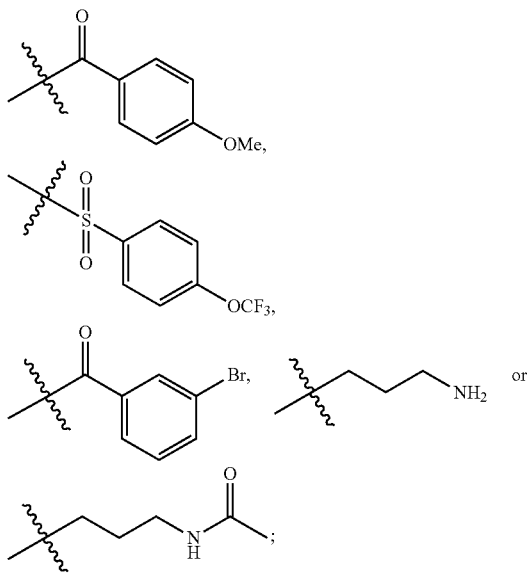

$R^5$ is H, —OH, —$CH_3$, —$OCH_3$, —F, —Cl, —$CF_3$ or —CN; $R^6$ is H, —OH, —$OCH_3$, —F or —Cl; $R^8$ is H, —$CH_3$, —$CH_2CH_3$, —$CH_2OH$, —$CO_2H$, —$CO_2CH_3$, —$CO_2CH_2CH_3$ or —$CF_3$; and n is 1 or 2.

In a thirty-third alternative embodiment, the invention is a compound of formula (I) wherein, the compound is of formula (IA):

or a pharmaceutically acceptable salt or hydrate or solvate thereof.

In a sixth embodiment the invention is a compound selected from:

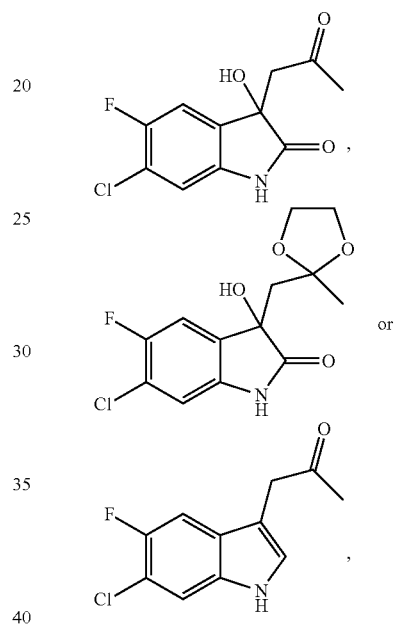

or a pharmaceutically acceptable salt, solvate or hydrate thereof.

Section I: General Terms

Listed below are definitions of various terms used to describe the novel intermediates and synthetic steps of the present invention. These definitions, either by replacing one, more than one or all general expressions or symbols used in the present disclosure and thus yielding embodiments of the invention, in particular apply to the terms as they are used throughout the specification unless they are otherwise defined in specific instances either individually or as part of a larger group. Thus, the general definitions used above and below, unless defined differently, have the following meanings:

The term "$C_1$-$C_{20}$-" defines a moiety with up to and including maximally 20, especially up to and including maximally 7 carbon atoms, said moiety being branched (one or more times) or straight-chained and bound via a terminal or a non-terminal carbon.

Alkyl being a radical or part of a radical is a straight or branched (one or, if desired and possible, more times) carbon chain, and is especially $C_1$-$C_7$-alkyl, such as $C_1$-$C_4$-alkyl, in particular branched $C_1$-$C_4$-alkyl, such as isopropyl. The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, iso-propyl, n-butyl, isobutyl, sec-butyl, tert-butyl, in particular methyl, ethyl, n-propyl, iso-propyl, n-butyl, isobutyl, sec-butyl, tert-butyl; preferably methyl.

Alkylamino and dialkylamino refer to alkyl-NH— and (alkyl)$_2$N—, respectively, wherein alkyl may be linear or branched. The alkyl group for example comprises 1 to 7 and in particular 1 to 4 C atoms. Some examples are methylamino, dimethylamino, ethylamino, and diethylamino; preferably methyamino.

Halo or halogen is preferably fluoro, chloro, bromo or iodo, preferably fluoro or chloro; where halo is mentioned as a substituent, where possible, one or more (e.g. up to three or one) halogen atoms may be present, e.g. in halo-$C_1$-$C_7$-alkyl, such as trifluoromethyl, 2,2-difluoroethyl or 2,2,2-trifluoroethyl.

Halo-$C_1$-$C_7$-alkyl may be linear or branched and in particular comprises 1 to 4 C atoms, for example 1 or 2 C atoms. Examples are fluoromethyl, difluoromethyl, trifluoromethyl, chloromethyl, dichloromethyl, trichloromethyl, 2-chloroethyl and 2,2,2-trifluoroethyl; preferably trifluoromethyl.

Alkoxy, being a radical or part of a radical, refers to alkyl-O—, wherein the term alkyl is as defined herein, and includes, for example, $C_1$-$C_{20}$-alkoxy (—O—$C_1$-$C_{20}$alkyl), preferably $C_1$-$C_7$-alkoxy (—O—$C_1$-$C_7$alkyl). In particular, alkoxy includes, for example, methoxy, ethoxy, n-propyloxy, isopropyloxy, n-butyloxy, isobutyloxy, sec-butyloxy, tert-butyloxy, pentyloxy, hexyloxy and heptyloxy radicals; preferably methoxy.

The term "optically active base" describes, for example, chiral amines, preferably chiral tertiary amines, more preferably cinchona alkaloids, such as quinidine and quinine, most preferably modified cinchona alkaloids. Examples of such modified cinchona alkaloids are detailed, for example, in Tian, S.-K.; Chen, Y.; Hang, J.; Tang, L.; McDiad, P.; Deng, L. *Acc. Chem. Res.* 2004, 37, 621-631 and references cited therein.

The term "phase transfer catalyst" as used herein refers to a catalytic amount of a chemical agent that enhances the rate of a reaction between chemical species located in different phases (eg. immiscible liquids or solid and liquid) by extracting one of the reactants, most commonly an anion, across the interface into the other phase. These catalysts include quaternary ammonium or phosphonium salts (e.g. tetraalkylammonium salts, wherein alkyl can be same or different), or agents that complex inorganic cations (e.g. crown ethers or other cryptands). The catalyst cation is not consumed in the reaction although an anion exchange does occur. In particular, suitable phase transfer catalysts to be used according to the present invention are quaternary ammonium salts, for example of the formula $R_mR_nR_iR_kNX$, wherein $R_mR_nR_iR_k$ are, either the same or different, alkyl, and X is halo (eg. chloride, bromide, iodide) or hydroxide, for example, tetra-n-butylammonium hydroxide.

A "heterogeneous" catalyst as used herein refers to a catalyst supported on a carrier, typically although not necessarily a substrate comprised of an inorganic material, for example, a porous material such as carbon, silicon and/or aluminum oxide.

A "homogeneous" catalyst as used herein refers to a catalyst that is not supported on a carrier.

The term "chiral" refers to molecules which have the property of non-superimposability on their mirror image partner, while the term "achiral" refers to molecules which are superimposable on their mirror image partner.

The term "catalyst" means any substance that affects the rate of a chemical reaction by lowering the activation energy for the chemical reaction.

The term "powder catalyst" means a catalyst with a water contain of from 0 to 30 mass %.

The term "substrate to catalyst ratio" (S/C\ refers to the molar ratio of starting compounds, or salts thereof, to "transition metal catalyst".

The term "work-up" means the work of isolation and/or purification which is carried out once the reaction is finished.

As used herein, unless specified otherwise, the term "room temperature" or "ambient temperature" means a temperature of from 15 to 30° C., such as of from 20 to 30° C., such as of from 20 to 25° C.

The term "inert" as used throughout this application, means unreactive with any of the reactants, solvents, or other components of the reaction mixture. Such inert conditions are generally accomplished by using inert gas such as carbon dioxide, helium, nitrogen, argon, among other gases.

Bonds with the asterisk (*) denote point of binding to the rest of the molecule.

The compounds of the present invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

In the formulae of the present application the term "∼∼∼", "↷" or "—" on a C-sp$^3$ represents a covalent bond wherein the stereochemistry of the bond is not defined. This means that the term "∼∼∼" or "—" on a C-sp$^3$ comprises an (S) configuration as well as an (R) configuration of the respective chiral centre. Furthermore, mixtures are also encompassed, e.g., mixtures of enantiomers, such as racemates, are encompassed by the present invention.

In the formulae of the present application the term "∼∼∼" or "↷" on a C-sp$^2$ represents a covalent bond, wherein the stereochemistry or the geometry of the bond is not defined. This means that the term "∼∼∼" on a C-sp$^2$ comprises a cis (Z) configuration as well as a trans (E) configuration of the respective double bond. Furthermore, mixtures are also encompassed, e.g., mixtures of double bond isomers are encompassed by the present invention.

In the formulae of the present application, the term "=====" indicates a Csp$^3$-Csp$^3$ bond or a Csp$^2$-Csp$^2$ bond.

The compounds of the present invention can possess one or more asymmetric centers. The preferred absolute configurations are as indicated herein specifically.

In the formulae of the present application the term "╱" on a C-sp$^3$ indicates the absolute stereochemistry, either (R) or (S).

In the formulae of the present application the term "╲" on a C-sp$^3$ indicates the absolute stereochemistry, either (R) or (S).

The term "stereomeric purity" at a given percentage means that the designated stereoisomer predominates at that given percentage in a mixture of stereosiomers.

The term "stereoisomer" means one of the absolute configurations of a single organic molecule having at least one asymmetric carbon. Included within the definition of a stereoisomer are enantiomers and diasteromers.

The term "resolution" refers to the separation or concentration or depletion of one of the stereoisomers of a molecule.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-. N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines for example triethylamine or tri(2-hydroxyethyl)amine, N-ethyl-piperidine. N,N'-dimethylpiperazine, t-butylamine, n-butylamine, phenylethylamine, dicyclohexylamine or cyclohexylamine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

Preferred salts forms include, for example, acid addition salts. The compounds having at least one acid group (e.g., COOH or 5-tetrazolyl) can also form salts with bases. Suitable salts with bases are, e.g., metal salts, such as alkali metal or alkaline earth metal salts, e.g., sodium, potassium, calcium or magnesium salts, or salts with ammonia or an organic amine, such as morpholine, thiomorpholine, piperidine, pyrrolidine, a mono-, di- or tri-lower alkylamine, e.g., ethyl-, tert-butyl-, diethyl-, diisopropyl-, triethyl-, tributyl- or dimethylpropylamine, or a mono-, di- or trihydroxy lower alkylamine, e.g., mono-, di- or tri-ethanolamine. Corresponding internal salts may furthermore be formed. Salts which are unsuitable for pharmaceutical uses but which can be employed, e.g., for the isolation or purification of free compounds I or their pharmaceutically acceptable salts, are also included. Most preferably the salt of formula (IV) is the camphorsulfonic acid salt.

In particular, the term "salt of a compound of formula (IV)" refers, for example, to an amine salt thereof, an alkali salt thereof or an earth alkali metal salt thereof (eg. sodium salt, potassium salt, calcium salt, magnesium salt, etc). In particular, the term "amine" in the expression "amine salt thereof", for example when referring to an amine salt of the compound of formula (IV), means tertiary amine of formula $NR9R10R11$, secondary amine of formula $NHR9R10R$ or primary amine of formula $NH_2R9$, wherein R9, R10 and R11 are, independently from one another, alkyl, aryl, cycloalkyl or heterocyclyl, as defined herein, preferably alkyl or cycloalkyl. The term "amine" is, for example, diphenylamine, diisopropylamine, dimethylamine, triethylamine, diisopropylethylamine, dicyclohexylamine, t-butylamine, n-butylamine or cyclohexylamine, in particular, t-butylamine, n-butylamine or cyclohexylamine, more preferably n-butylamine or cyclohexylamine.

As used in this specification and the appended claims, the singular forms "a", "an" and "the" include plural referents unless the context clearly indicates otherwise. Thus, for example, reference to "a polypeptide" includes more than one polypeptide.

Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure.

The section headings used herein are for organizational purposes only and not to be construed as limiting the subject matter described.

The abbreviations used for the genetically encoded amino acids are conventional and are as follows:

| Amino Acid | Three-Letter | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic acid" refers to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"Aminotransferase" and "transaminase" are used interchangeably herein to refer to a polypeptide having an enzymatic capability of transferring an amino group ($NH_2$) from a primary amine to a carbonyl group (C=O) of an acceptor molecule. Transaminases as used herein include naturally occurring (wild type) transaminase as well as non-naturally occurring engineered polypeptides generated by human manipulation.

"Amino acceptor" and "amine acceptor," "keto substrate," "keto," and "ketone" are used interchangeably herein to refer to a carbonyl (keto, or ketone) compound which accepts an amino group from a donor amine. In some embodiments, amino acceptors are molecules of the following general formula,

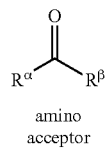

amino acceptor in which each of $R^\alpha$ and $R^\beta$, when taken independently, is an alkyl, cycloalkyl, heterocycloalkyl, aryl, or heteroaryl, which can be unsubstituted or substituted with one or more enzymatically acceptable groups, $R^\alpha$ may be the same or different from $R^\beta$ in structure or chirality. In some embodiments, $R^\square$ and $R^\square$, taken together, may form a ring that is unsubstituted, substituted, or fused to other rings. Amino acceptors include keto carboxylic acids and alkanones (ketones). Typical keto carboxylic acids are α-keto carboxylic acids such as glyoxalic acid, pyruvic acid, oxaloacetic acid, and the like, as well as salts of these acids. Amino acceptors also include substances which are converted to an amino acceptor by other enzymes or whole cell processes, such as fumaric acid (which can be converted to oxaloacetic acid), glucose (which can be converted to pyruvate), lactate, maleic acid, and others. Amino acceptors that can be used include, by way of example and not limitation, 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, 1-(4-bromophenyl)ethanone, 2-methylcyclohexamone, 7-methoxy-2-tetralone, 1-hydroxybutan-2-one, pyruvic acid, acetophenone, 3'-hydroxyacetophenone, 2-methoxy-5-fluoroacetophenone, levulinic acid, 1-phenylpropan-1-one, 1-(4-bromophenyl)propan-1-one, 1-(4-nitrophenyl)propan-1-one, 1-phenylpropan-2-one, 2-oxo-3-methylbutanoic acid, 1-(3-trifluoromethylphenyl)propan-1-one, hydroxypropanone, methoxyoxypropanone, 1-phenylbutan-1-one, 1-(2,5-dimethoxy-4-methylphenyl)butan-2-one, 1-(4-hydroxyphenyl)butan-3-one, 2-acetylnaphthalene, phenylpyruvic acid, 2-ketoglutaric acid, and 2-ketosuccinic acid, including both (R) and (S) single isomers where possible.

"Amino donor" or "amine donor" refers to an amino compound which donates an amino group to the amino acceptor, thereby becoming a carbonyl species. In some embodiments, amino donors are molecules of the following general formula,

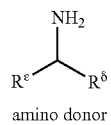

amino donor in which each of $R^\epsilon$ and $R^\delta$, when taken independently, is an alkyl, cycloalkyl, heterocycloalkyl, aryl, or heteroaryl, which is unsubstituted or substituted with one or more enzymatically non-inhibiting groups. $R^\epsilon$ can be the same or different from $R^\delta$ in structure or chirality. In some embodiments, $R^\epsilon$ and $R^\delta$, taken together, may form a ring that is unsubstituted, substituted, or fused to other rings. Typical amino donors that can be used include chiral and achiral amino acids, and chiral and achiral amines. Amino donors that can be used include, by way of example and not limitation, isopropylamine (also referred to as 2-aminopropane), α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, D,L-ornithine, β-alanine, taurine, n-octylamine, cyclohexylamine, 1,4-butanediamine (also referred to as putrescine), 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-nn-ethylcyclohexylamine, 1-aminotetralin, 2-aminotetralin, 2-amino-5-methoxytetralin, and 1-aminoindan, including both (R) and (S) single isomers where possible and including all possible salts of the amines.

"Chiral amine" refers to amines of general formula $R^1$—$CH(NH_2)$—$R^1$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^1$ and $R^2$ above) also can vary widely and include alkyl, aralkyl, aryl, halo, hydroxy, lower alkyl, lower alkoxy, lower alkylthio, cycloalkyl, carboxy, carbalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Pyridoxal-phosphate," "PLP," "pyridoxal-5'-phosphate," "PYP," and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7], Pyridoxal-5'-phosphate can be produced in vivo by phosphorylation and oxidation of pyridoxol (also known as Vitamin $B_6$). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces a chiral amine and regenerates the coenzyme. In some embodiments, the pyridoxal-5'-phosphate can be replaced by other members of the vitamin $B_6$ family, including pyridoxine (PN), pyridoxal (PL), pyridoxamine (PM), and their phosphorylated counterparts; pyridoxine phosphate (PNP), and pyridoxamine phosphate (PMP).

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:4 having at the residue corresponding to X14 a valine" or X14V refers to a reference sequence in which the corresponding residue at X14 in SEQ ID NO:4, which is a tyrosine, has been changed to valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X14 as compared to SEQ ID NO: 4" refers to a change of the amino acid residue at the polypeptide position corresponding to position 14 of SEQ ID NO:4. Thus, if the reference polypeptide of SEQ ID NO: 4 has a tyrosine at position 14, then a "residue difference at position X14 as compared to SEQ ID NO:4" an amino acid substitution of any residue other than tyrosine at the position of the polypeptide corresponding to position 14 of SEQ ID NO: 4. In most instances herein, the specific amino acid residue difference at a position is indicated as "XnY" where "Xn" specified the corresponding position as described above, and "Y" is the single letter identifier of the amino acid found in the engineered polypeptide (Le., the different residue than in the reference polypeptide). In some embodiments, there more than one amino acid can appear in a specified residue position, the alternative amino acids can be listed in the form XnY/Z, where Y and Z represent alternate amino acid residues. In some instances (e.g., in Table 2A and 2B), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. Furthermore, in some instances, a polypeptide of the present disclosure can include one or more amino acid residue differences relative to a reference sequence, which is indicated by a list of the specified positions where changes are made relative to the reference sequence. The present disclosure includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below.

TABLE 1

| Residue | Possible Conservative Substitutions |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the polypeptide of SEQ ID NO:2 or engineered transaminase of SEQ ID NO:34.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved transaminase enzymes may be present within a cell, present in the cellular medium, or prepared in various forms, such as lysates or isolated preparations. As such, in some embodiments, the improved transaminase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure transaminase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved transaminases polypeptide is a substantially pure polypeptide composition.

"Stereoselectivity" refers to the preferential formation in a chemical or enzymatic reaction of one stereoisomer over another. Stereoselectivity can be partial, where the formation of one stereoisomer is favored over. the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diasteromers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate, e.g., Compound (IA), to its corresponding chiral amine product, e.g., Compound (IIA), with at least about 85% stereomeric excess.

"Improved enzyme property" refers to a transaminase polypeptide that exhibits an improvement in any enzyme property as compared to a reference transaminase. For the engineered transaminase polypeptides described herein, the comparison is generally made to the wild-type transaminase enzyme, although in some embodiments, the reference transaminase can be another improved engineered transaminase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), stereospecificity, and stereoselectivity (including enantioselectivity).

"Increased enzymatic activity" refers to an improved property of the engineered transaminase polypeptides, which can be represented by an increase in specific activity (e.g., product produced/time/weight protein) or an increase in percent conversion of the substrate to the product (e.g., percent conversion of starting amount of substrate to product in a specified time period using a specified amount of transaminase) as compared to the reference transaminase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 times the enzymatic activity of the corresponding wild-type transaminase enzyme, to as much as 2 times, 5 times, 10 times, 20 times, 25 times, 50 times, 75 times, 100 times, or more enzymatic activity than the naturally occurring transaminase or another engineered transaminase from which the transaminase polypeptides were derived. Transaminase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following derivatization, such as with o-phthaldialdehyde (OPA). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a transaminase polypeptide can be expressed as "percent conversion" of the substrate to the product.

"Thermostable" refers to a transaminase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a transaminase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"Thermo- and solvent stable" refers to a transaminase polypeptide that is both thermostable and solvent stable.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature. G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci USA 83:8893-8897; Freier et al., 1986, Proc. Natl. Acad. Sci USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and VVetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered transaminase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the transaminase enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, cofactor loading, temperature, pH, buffers, co-solvents, etc.) under which a transaminase polypeptide of the present disclosure is capable of converting a substrate compound to a product compound (e.g., conversion of Compound (IA) to Compound (IIA)). Exemplary "suitable reaction conditions" are provided in the present disclosure and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the transaminase biocatalyst in the process disclosed herein is compound (IA).

"Product" in the context of a biocatalyst mediated process refers to the compound or molecule resulting from the action of the biocatalyst. For example, an exemplary product for the transaminase biocatalyst in the process disclosed herein is compound (IIA).

The present disclosure provides methods of using polypeptides having transaminase activity for the synthesis of (S)-1-(1H-5-fluoro-6-chloro-indol-3-yl)propan-2-amine in enantiomeric excess of (R)-1-(1H-5-fluoro-6-chloro-indol-3-yl)propan-2-amine. Where the description relates to polypeptides, it is to be understood that it also describes the polynucleotides encoding the polypeptides.

Aminotransferases, also known as transaminases, catalyze the transfer of an amino group from a primary amine of an amino donor substrate to the carbonyl group (e.g., a keto or aldehyde group) of an amino acceptor molecule. Aminotransferases have been identified from various organisms, such as *Alcaligenes denitrificans, Bordetella bronchiseptica, Bordetella parapertussis, Brucella melitensis, Burkholderia malle, Burkholderia pseudomallei, Chromobacterium violaceum, Oceanicola granulosus* HTCC2516, *Oceanobacter* sp. RED65, *Oceanospirillum* sp. MED92, *Pseudomonas putida, Ralstonia solanacearum, Rhizobium meliloti, Rhizobium* sp. (strain NGR234), *Vibrio fluvialis, Bacillus thuringensis,* and *Klebsiella pneumoniae* (Shin et al., 2001, Biosci. Biotechnol, Biochem. 65:1782-1788).

Transaminases are useful for the chiral resolution of racemic amines by exploiting the ability of the transaminases to carry out the reaction in a stereospecific manner, i.e., preferential conversion of one enantiomer to the corresponding ketone, thereby resulting in a mixture enriched in the other enantiomer (see, e.g., Koselewski et al., 2009. Org Lett. 11(21):4810-2). The stereoselectivity of transaminases in the conversion of a ketone to the corresponding amine also make these enzymes useful in the asymmetric synthesis of optically pure amines from the corresponding keto compounds (see, e.g., Höhne et al., "Biocatalytic Routes to Optically Active Amines," Chem Cat Chem 1(1):42-51; Zua and Hua, 2009, Biotechnol J. 4(10):1420-31).

The □ ω-transaminase from *Vibrio fluvialis* □ω-VfT) displays high enantioselectivity for (S)-enantiomer of chiral amines and has distinctive substrate specificity for chiral aromatic amines (Shin and Kim, 2001, J. Org. Chem. 67:2848-2853). The high enantioselectivity of□ ω-VfT has been applied to chiral resolution of amines (H. Yun, B.-K. Cho, B.-G. Kim, Biotechnol. Bioeng. 2004, 87, 772-778; J.-S. Shin, B.-G. Kim, Biotechnol. Bioeng. 1997, 55, 348-358; M. Hçhne, K. Robins, U. T. Bornscheuer, Adv. Synth. Catal. 2008, 350,802-807). The enzyme has also been used in the asymmetric synthesis of optically pure amines using a prochiral ketone substrate. However, limitation in asymmetric synthesis is the unfavorable equilibrium of the reverse reaction (Shin and Kim, 1999, Biotechnol. Bioeng. 65, 206-211), inhibition of□ ω-VfT enzyme by the amine product (Shin et al., 2001, Biotechnol Bioeng 73:179-187; Yun and Kim, 2008, Biosci. Biotechnol. Biochem. 72(11): 3030-3033); low activity on amino acceptors having bulky side chains, such as aromatic groups (Shin and Kim, 2002, J. Org. Chem. 67:2848-2853); and low enzyme stability (Yun and Kim, supra).

Engineered transaminases derived from the transaminase of *Vibrio fluvialis* having increased resistance to aliphatic ketones are described in Yun et al., 2005, Appl Environ Micriobiol., 71(8):4220-4224) while ω-VfTs with broadened amino donor substrate specificity are described in Cho et al., 2008, Biotechnol Bioeng. 99(2):275-84. Patent publications WO2010081053 and US20100209981, incorporated by reference herein, describe engineered ω-VfTs having increased stability to temperature and/or organic solvent and enzymatic activity towards structurally different amino acceptor molecules.

The present disclosure relates to methods of using engineered transaminase polypeptides derived from *V. fluvialis* that efficiently mediate conversion of 1-(1H-5-fluoro-6-chloro-indol-3-yl)propan-2-one, to product compound (S)-1-(1H-5-fluoro-6-chloro-indol-3-yl)propan-2-amine in enantiomeric excess. Significantly, the disclosure identifies amino acid residue positions and corresponding mutations in the transaminase polypeptide that increase the enzymatic activity, enantioselectivity, stability and refractoriness to the product inhibition in the conversion of 1-(1H-5-fluoro-6-chloro-indol-3-yl)propan-2-one, to product compound (S)-1-(1H-5-fluoro-6-chloro-indol-3-yl)propan-2-amine.

Accordingly, in one aspect, the present disclosure relates to methods of using polypeptides that are capable of converting the substrate converting substrate compound (IA), 1-(1H-5-fluoro-6-chloro-indol-3-yl)propan-2-one, to product compound (IIA), (S)-1-(1H-5-fluoro-6-chloro-indol-3-yl)propan-2-amine,

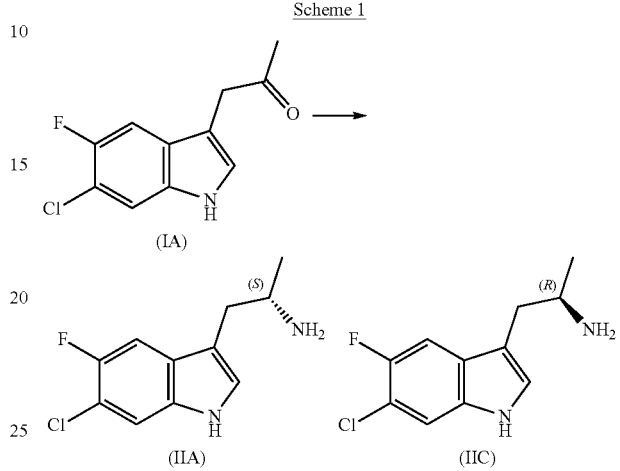

Scheme 1 in the presence of an amino donor, where the (S)-1-(1H-5-fluoro-6-chloro-indol-3-yl)propan-2-amine is produced in enantiomeric excess of compound (IIC), (R)-1-(1H-5-fluoro-6-chloro-indol-3-yl)propan-2-amine.

In some embodiments, the polypeptides used in the methods are non-naturally occurring transaminases engineered for improved properties as compared to the wild-type *V. fluvialis* polypeptide of SEQ ID NO:2, or another engineered polypeptide, for example SEQ ID NO:4. These engineered transaminase polypeptides adapted for efficient conversion of conversion of 1-(1H-5-fluoro-6-chloro-indol-3-yl)propan-2-one to (S)-1-(1H-5-fluoro-6-chloro-indol-3-yl)propan-2-amine have one or more residue differences as compared to the amino acid sequence of SEQ ID NO:2 or a reference engineered transaminase polypeptide, such as the reference polypeptide of SEQ ID NO:4. The residue differences are associated with enhancements in enzyme properties, including enzymatic activity, enzyme stability, and resistance to inhibition by the product amine.

In some embodiments, the engineered transaminase polypeptides used in the instant disclosure show increased activity in the conversion of the substrate 1-(1H-5-fluoro-6-chloro-indol-3-yl)propan-2-one to product (S)-1-(1H-5-fluoro-6-chloro-indol-3-yl)propan-2-amine product in enantiomeric excess in a defined time with the same amount of enzyme as compared to the wild type or a reference engineered enzyme. In some embodiments, the engineered transaminase polypeptide has at least about 1.2 fold, 1.5 fold, 2 fold, 3 fold, 4 fold, 5 fold, 10 fold, 20 fold, 30 fold, 40 fold, or 50 fold or more the activity as compared to the polypeptide represented by SEQ ID NO:4 under suitable reaction conditions.

In some embodiments, the engineered transaminase polypeptides used in the instant disclosure have increased stability to temperature and/or solvents used in the conversion reaction as compared to the wild type or a reference engineered enzyme. In some embodiments, the engineered transaminase polypeptide has at least 1.2 fold, 1.5 fold, 2 fold, 3 fold, 4 fold, 5 fold, 10 fold or more the stability as compared to the polypeptide of SEQ ID NO:4 under suitable reaction conditions.

In some embodiments, the engineered transaminase polypeptides used in the instant disclosure have increased refractoriness or resistance to product amine (S)-1-(1H-5-fluoro-6-chloro-indol-3-yl)propan-2-amine as compared to the wild type or a reference engineered enzyme. In some embodiments, the engineered transaminase polypeptide has at least 1.2 fold, 1.5 fold, 2 fold, 3 fold, 4 fold, 5 fold, or more resistant to inhibition by 1-(1H-5-fluoro-6-chloro-indol-3-yl)propan-2-amine, in particular (S)-1-(1H-5-fluoro-6-chloro-indol-3-yl)propan-2-amine, as compared to the polypeptide represented by SEQ ID NO:4 under suitable reaction conditions, as further described below.

In some embodiments, the engineered transaminase polypeptides used in the instant disclosure are capable of converting the substrate 1-(1H-5-fluoro-6-chloro-indol-3-yl)propan-2-one to product (S)-1-(1H-5-fluoro-6-chloro-indol-3-yl)propan-2-amine in enantiomeric excess of greater than 90%, 91%, 92%, 93%, 94%, 95%, 96%, 97%, 98%, 99%, 99.5 or greater over (R)-1-(1H-5-fluoro-6-chloro-indol-3-yl)propan-2-under suitable reaction conditions.

In some embodiments, the engineered transaminase polypeptides used in the instant disclosure are capable of converting compound (IA) to compound (IIA) with increased tolerance for the presence of substrate relative to the reference polypeptide of SEQ ID NO: 4 under suitable reaction conditions. Thus, in some embodiments the engineered transaminase polypeptides are capable of converting the substrate compound (IIA) to product compound (IA) in the presence of a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L. about 175 g/L or about 200 g/L or more with a percent conversion of at least about at least about 50%, at least about 60%, at least about 70%, at least about 80%, at least about 90%, at least about 95%, at least about 98%, or at least about 99%, in a reaction time of about 72 h or less, about 48 h or less, about 36 h or less, or about 24 h less, under suitable reaction conditions.

The suitable reaction conditions under which the above-described improved properties of the engineered polypeptides carry out the conversion can be determined with respect to concentrations or amounts of polypeptide, substrate, cofactor, buffer, co-solvent, pH, and/or conditions including temperature and reaction time, as further described below and in the Examples.

The exemplary engineered polypeptides used in the instant disclosure have associated with their improved properties for conversion of compound (IA) to compound WA) and which include one or more residue differences as compared to SEQ ID NO:2 at the following residue positions: X9; X14; X18; X21; X26; X31; X33; X41; X45; X47; X57; X70; X86; X88; X107; X113; X132; X133; X146; X147; X148; X153; X163; X168; X173; X177; X203; X211; X233T; X235; X244; X250; X284; X294; X314; X315; X318; X323; X324; X324; X346; X383; X391; X395; X398; X400; X417; X419; X420; X423; X424; X427; X448; and X451. The specific amino acid differences at each of these positions that are associated with the improved properties of the exemplary polypeptides of Table 2A and 2B include: X9T; X14V; X18A; X21H; X26R; X31M; X31S; X33T; X41L; X45H; X47N; X57F; X57Y; X70A; X86D; X86Y; X88A; X88L; X107P; X113L; X113V; X132F; X133R; X146L; X147K; X148Q; X148R; X153S; X163F; X163I; X163L; X163R; X163V; X168K; X168S; X173A; X177L; X203S; X211K; X233T; X235P; X244T; X250A; X284A; X294V; X314N; X315G; X318D; X323T; X324G; X324H; X346L; X383V; X391A; X395P; X398L; X398V; X398W; X400G; X417M; X419S; X420N; X4231; X424V; X424A; X427Y; X448E; and X451D.

The residue differences as compared to the engineered transaminase represented by SEQ ID NO:4 includes those at residue positions: X14; X26; X31; X33; X41; X47; X57; X70; X86; X88; X107; X113; X132; X148; X163; X168; X173; X203; X250; X284; X314; X315; X324; X346; X395; X398; X400; X417; X419; X420; X423; X424; X448; and X451. The specific amino acid differences at these positions include: X14V; X26R; X31S; X33T; X41L; X47N; X57F; X57Y; X70A; X86D; X88A; X88L; X107P; X113L; X113V; X132F; X148Q; X148R; X163I; X163L; X163R; X163V; X168K; X168S; X173A; X203S; X250A; X284A; X314N; X315G; X324H; X346L; X395P; X398L; X398V; X398W; X400G; X417M; X419S; X420N; X4231; X424V; X448E; and X451D. Although residue differences compared to SEQ ID NO:4 also occur at residue positions X153 and X383, these differences represent reversions to the amino acid residue present on the wild type sequence of SEQ ID NO:2, indicating that interconversions between amino acids S and V at residue position X153 and between amino acids A and V at residue position X383 have no significant deleterious effects on the engineered enzyme properties.

The structure and function information for exemplary non-naturally occurring (or engineered) transaminase polypeptides used in the method of the present disclosure are shown below in Table 2A and 2B. The odd numbered sequence identifiers (i.e., SEQ ID NOs) refer to the nucleotide sequence encoding the amino acid sequence provided by the even numbered SEQ ID NOs, and the sequences are provided in the electronic sequence listing file accompanying this disclosure, which is hereby incorporated by reference herein. The amino acid residue differences are based on comparison to the reference sequence of SEQ ID NO: 4, which is an engineered transaminases derived from the wild type ω-VfT polypeptide having the following 24 amino acid residue differences A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; F427Y relative to SEQ ID NO:2. The activity of each engineered polypeptide relative to the reference polypeptide of SEQ ID NO: 4 was determined as conversion of the ketone substrate 1-(1H-5-fluoro-6-chloro-indol-3-yl)propan-2-one, to product amine compound (S)-1-(1H-5-fluoro-6-chloro-indol-3-yl)propan-2-amine over a set time period and temperature in a high-throughput (HTP) assay, which was used as the primary screen. The HTP assay values in Table 2A were determined using *E. coli* clear cell lysates in 96 well-plate format of ~200 μL volume per well following assay reaction conditions as noted in the table and the Examples. In some instances, a shake-flask powder (SFP) and/or downstream processed (DSP) powder assay were used as a secondary screen to assess the properties of the engineered transaminases, the results of which are provided in Table 2B. The SFP and DSP forms provide a more purified powder preparation of the engineered polypeptides. For example, the engineered transaminase in the SFP preparations is approximately 30% of the total protein while the DSP preparations can contain the engineered transaminases that are approximately 80% of total protein.

The levels of activity (i.e., "+" "++", etc.) are defined as follows: "+" indicates 1.2 fold or greater activity as compared to that of SEQ ID NO: 4 for engineered transaminase polypeptide SEQ ID NO: 6 to 14, and 1.2 or greater activity as compared to that of SEQ ID NO: 8 for engineered transaminase polypeptide SEQ ID NO: 16 to 154; and a "++" indicates 5 fold or greater activity as compared to that of SEQ ID NO:4 for engineered transaminase polypeptides SEQ ID NO: 6-14, and 5 fold or greater activity as compared that of SEQ ID NO:8 for engineered transaminase polypeptides SEQ ID NO: 16 to 154. The stability data is obtained by including the following amounts of product (S)-1-(1H-5-fluoro-6-chloro-indol-3-yl)propan-2-amine in the assay and comparing the activity to that of a reference enzyme under the same conditions: 14 g/L for analysis of the engineered transaminase polypeptides of SEQ ID NO. 6 to 14, and 16 g/L for analysis of the engineered transaminases polypeptides SEQ ID NO. 16 to 154. Assessment of stability was made by comparing activities at two different temperatures, 55° C. and 50° C.

TABLE 2A

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 1/2 | n/a | | Nd | nd | nd |
| 3/4 | A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; F427Y; | | "Control" | "Control" | "Control" |
| 5/6 | A9T; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y; | F163L; | + | + | + |
| 7/8 | A9T; G18A; D21H; V31M; N45H; F86Y; A133R; R146L; W147K; V153S; K163I; V177L; R211K; P233T; A235P; P244T; M294V; P318D; A323T; S324G; A383V; T391A; C424A; F427Y; | F163I; | + | + | nd |
| 9/10 | A9T; G18A; D21H; V31M; N45H; F86Y; A133R; R146L; W147K; V153S; K163R; V177L; R211K; P233T; A235P; P244T; M294V; P318D; A323T; S324G; A383V; T391A; C424A; F427Y; | F163R; | + | nd | nd |
| 11/12 | A9T; G18A; D21H; V31M; N45H; F86D; A133R; R146L; W147K; V153S; K163F; V177L; R211K; P233T; A235P; P244T; M294V; P318D; A323T; S324G; A383V; T391A; C424A; F427Y; | Y86D; | + | + | + |
| 13/14 | A9T; G18A; D21H; V31M; N45H; F86Y; A133R; R146L; W147K; V153S; K163V; V177L; R211K; P233T; A235P; P244T; M294V; P318D; A323T; S324G; A383V; T391A; C424A; F427Y; | F163V; | + | nd | nd |
| 15/16 | A9T; Y14V; G18A; D21H; H26R; V31M; N45H; F86Y; R88L; Y113L; A133R; R146L; W147K; V153S; K163L; V177L; R211K; P233T; A235P; P244T; M294V; P318D; A323T; S324G; A383V; T391A; C424A; F427Y; | Y14V; H26R; R88L; Y113L; F163L; | + | + | ++ |
| 17/18 | A9T; Y14V; G18A; D21H; H26R; V31M; N45H; W57F; F86Y; A133R; R146L; W147K; V153S; K163L; V177L; R211K; P233T; A235P; P244T; M294V; P318D; A323T; S324G; A383V; T391A; C424A; F427Y; | Y14V; H26R; W57F; F163L; | Nd | + | + |
| 19/20 | A9T; Y14V; G18A; D21H; V31M; V33T; N45H; W57F; F86Y; R88L; Y113L; A133R; R146L; W147K; V153S; K163L; V177L; R211K; P233T; A235P; P244T; M294V; P318D; A323T; S324G; A383V; T391A; C424A; F427Y; V448E; | Y14V; V33T; W57F; R88L; Y113L; F163L; V448E; | Nd | + | nd |
| 21/22 | A9T; Y14V; G18A; D21H; H26R; V31M; N45H; F86Y; R88A; Y113L; A133R; R146L; | Y14V; H26R; R88A; Y113L; N148Q; L163I; | + | + | + |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| | W147K; N148Q; V153S; K163I; V177L; R203S; R211K; P233T; A235P; P244T; M294V; P318D; A323T; S324G; A383V; T391A; C424A; F427Y; | R203S; | | | |
| 23/24 | A9T; G18A; D21H; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y; V448E; | W57F; R88L; Y113L; N148Q; L163I; V448E; | + | + | + |
| 25/26 | A9T; Y14V; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y; | Y14V; F163L; | Nd | nd | + |
| 27/28 | A9T; Y14V; G18A; D21H; H26R; V31M; N45H; F86Y; R88A; A133R; R146L; W147K; N148Q; V153S; K163I; V177L; R211K; P233T; A235P; P244T; M294V; P318D; A323T; S324G; A383V; T391A; C424A; F427Y; | Y14V; H26R; R88A; N148Q; L163I; | + | + | + |
| 29/30 | A9T; Y14V; G18A; D21H; H26R; V31M; N45H; F86Y; R88L; Y113V; A133R; R146L; W147K; V153S; K163L; V177L; R211K; P233T; A235P; P244T; M294V; P318D; A323T; S324G; A383V; T391A; C424A; F427Y; | Y14V; H26R; R88L; Y113V; F163L; | + | + | + |
| 31/32 | A9T; Y14V; G18A; D21H; V31M; N45H; W57F; F86Y; Y113V; A133R; R146L; W147K; N148Q; V153S; K163L; V177L; R211K; P233T; A235P; P244T; M294V; P318D; A323T; S324G; A383V; T391A; C424A; F427Y; | Y14V; W57F; Y113V; N148Q; F163L; | + | + | nd |
| 33/34 | A9T; Y14V; G18A; D21H; H26R; V31M; N45H; W57F; F86Y; A133R; R146L; W147K; N148Q; V153S; K163I; V177L; R211K; P233T; A235P; P244T; M294V; P318D; A323T; S324G; A383V; T391A; C424A; F427Y; | Y14V; H26R; W57F; N148Q; L163I; | Nd | + | + |
| 35/36 | A9T; Y14V; G18A; D21H; H26R; V31M; N45H; F86Y; A133R; R146L; W147K; V153S; K163L; V177L; R211K; P233T; A235P; P244T; M294V; P318D; A323T; S324G; A383V; T391A; C424A; F427Y; | Y14V; H26R; F163L; | Nd | + | + |
| 37/38 | A9T; Y14V; G18A; D21H; H26R; V31M; N45H; W57F; F86Y; Y113L; A133R; R146L; W147K; V153S; K163L; V177L; R211K; P233T; A235P; P244T; M294V; P318D; A323T; S324G; A383V; T391A; C424A; F427Y; | Y14V; H26R; W57F; Y113L; F163L; | Nd | + | + |
| 39/40 | A9T; Y14V; G18A; D21H; H26R; V31M; N45H; F86Y; A133R; R146L; W147K; V153S; K163I; V177L; R211K; P233T; A235P; P244T; M294V; P318D; A323T; S324G; A383V; T391A; C424A; F427Y; | Y14V; H26R; L163I; | Nd | + | + |
| 41/42 | A9T; Y14V; G18A; D21H; H26R; V31M; N45H; W57F; F86Y; R88L; A133R; R146L; W147K; V153S; K163I; V177L; R211K; P233T; A235P; P244T; | Y14V; H26R; W57F; R88L; L163I; | Nd | + | + |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 43/44 | M294V; P318D; A323T; S324G; A383V; T391A; C424A; F427Y; A9T; Y14V; G18A; D21H; H26R; V31M; N45H; F86Y; Y113V; A133R; R146L; W147K; V153S; K163I; V177L; R211K; P233T; A235P; P244T; M294V; P318D; A323T; S324G; A383V; T391A; C424A; F427Y; | Y14V; H26R; Y113V; L163I; | Nd | + | nd |
| 45/46 | A9T; Y14V; G18A; D21H; H26R; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y; | Y14V; H26R; W57F; R88L; Y113L; N148Q; L163I; | Nd | + | + |
| 47/48 | A9T; Y14V; G18A; D21H; V31M; N45H; W57F; F86Y; R88L; A133R; R146L; W147K; N148Q; V153S; K163I; V177L; R211K; P233T; A235P; P244T; M294V; P318D; A323T; S324G; A383V; T391A; C424A; F427Y; | Y14V; W57F; R88L; N148Q; L163I; | + | + | + |
| 49/50 | A9T; Y14V; G18A; D21H; H26R; V31M; N45H; W57F; F86Y; R88L; Y113V; A133R; R146L; W147K; N148R; V153S; K163L; V177L; R211K; P233T; A235P; P244T; M294V; P318D; A323T; S324G; A383V; T391A; C424A; F427Y; | Y14V; H26R; W57F; R88L; Y113V; N148R; F163L; | Nd | + | nd |
| 51/52 | A9T; Y14V; G18A; D21H; V31M; N45H; F86Y; R88A; Y113V; A133R; R146L;W147K; V153S; K163I; V177L; R211K; P233T; A235P; P244T; M294V; P318D; A323T; S324G; A383V; T391A; C424A; F427Y; | Y14V; R88A; Y113V; L163I; | + | + | + |
| 53/54 | A9T; Y14V; G18A; D21H; H26R; V31M; N45H; F86Y; A133R; R146L; W147K; V153S; K163L; V177L; R211K; P233T; A235P; P244T; D250A; M294V; P318D; A323T; S324G; A383V; T391A; C424A; F427Y; | Y14V; H26R; F163L; D250A; | Nd | nd | + |
| 55/56 | A9T; Y14V; G18A; D21H; H26R; V31M; N45H; F86Y; R88L; Y113L; A133R; R146L; W147K; V153S; K163I; V177L; R211K; P233T; A235P; P244T; M294V; P318D; A323T; S324G; A383V; T391A; C424A; F427Y; | Y14V; H26R; R88L; Y113L; L163I; | + | + | + |
| 57/58 | A9T; Y14V; G18A; D21H; V31M; N45H; W57F; F86Y; R88A; Y113L; A133R; R146L; W147K; V153S; K163L; V177L; R211K; P233T; A235P; P244T; M294V; P318D; A323T; S324G; A383V; T391A; C424A; F427Y; | Y14V; W57F; R88A; Y113L; F163L; | Nd | nd | + |
| 59/60 | A9T; Y14V; G18A; D21H; H26R; V31M; N45H; W57F; F86Y; Y113L; A133R; R146L; W147K; N148R; V153S; K163L; V177L; R211K; P233T; A235P; P244T; M294V; P318D; A323T; S324G; A383V; T391A; C424A; F427Y; | Y14V; H26R; W57F; Y113L; N148R; F163L; | Nd | + | + |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 61/62 | A9T; Y14V; G18A; D21H; V31M; N45H; W57F; F86Y; Y113L; A133R; R146L; W147K; V153S; K163I; V177L; R211K; P233T; A235P; P244T; M294V; P318D; A323T; S324G; A383V; T391A; C424A; F427Y; | Y14V; W57F; Y113L; L163I; | + | + | + |
| 63/64 | A9T; G18A; D21H; V31M; N45H; F86Y; R88L; A133R; R146L; W147K; V153S; K163I; L173A; V177L; R211K; P233T; A235P; P244T; S284A; M294V; P318D; A323T; S324G; A383V; T391A; S400G; L417M; C424V; F427Y; | D86Y; R88L; F163I; L173A; S400G; A424V; | + | + | nd |
| 65/66 | A9T; G18A; D21H; V31M; V33T; N45H; F86Y; R88L; A133R; R146L; W147K; V153S; K163F; L173A; V177L; R211K; P233T; A235P; P244T; S284A; M294V; P318D; A323T; S324G; T391A; S400G; C424A; F427Y; | V33T; D86Y; R88L; L173A; V383A; S400G; | + | + | nd |
| 67/68 | A9T; G18A; D21H; V31M; N45H; F86D; A133R; R146L; W147K; V153S; K163F; V177L; R211K; P233T; A235P; P244T; M294V; P318D; A323T; S324H; A383V; T391A; S400G; C424A; F427Y; | Y86D; G324H; S400G; | + | + | nd |
| 69/70 | A9T; G18A; D21H; V31M; N45H; F86D; A133R; R146L; W147K; V153S; K163F; V168K; V177L; R211K; P233T; A235P; P244T; S284A; M294V; P318D; A323H; S324H; T391A; S400G; C424A; F427Y; | Y86D; V168K; G324H; V383A; S400G; | Nd | + | nd |
| 71/72 | A9T; G18A; D21H; V31M; N45H; F86D; A133R; R146L; W147K; V153S; K163F; L173A; V177L; R211K; P233T; A235P; P244T; S284A; M294V; P318D; A323T; S324H; A383V; T391A; C424A; F427Y; | Y86D; L173A; G324H; | Nd | + | nd |
| 73/74 | A9T; G18A; D21H; V31M; N45H; F86D; A133R; R146L; W147K; V153S; K163F; V177L; R211K; P233T; A235P; P244T; M294V; P318D; A323T; S324G; T391A; S400G; C424A; F427Y; | Y86D; V383A; S400G; | Nd | + | + |
| 75/76 | A9T; G18A; D21H; V31M; N45H; F86D; A133R; R146L; W147K; V153S; K163F; L173A; V177L; R211K; P233T; A235P; P244T; M294V; P318D; A323T; S324G; A383V; T391A; S400G; C424A; F427Y; V448E; | Y86D; L173A; S400G; V448E; | Nd | + | + |
| 77/78 | A9T; G18A; D21H; V31M; N45H; F86D; A133R; R146L; W147K; V153S; K163F; V177L; R211K; P233T; A235P; P244T; S284A; M294V; P318D; A323T; S324H; A383V; T391A; S400G; C424A; F427Y; | Y86D; G324H; S400G; | Nd | + | nd |
| 79/80 | A9T; G18A; D21H; V31M; N45H; F86D; A133R; R146L; W147K; V153S; K163F; L173A; V177L; R211K; P233T; A235P; P244T; S284A; M294V; P318D; A323T; S324H; A383V; T391A; S400G; C424A; F427Y; | Y86D; L173A; G324H; S400G; | Nd | + | nd |
| 81/82 | A9T; G18A; D21H; V31M; I41L; N45H; W57Y; D70A; F86Y; D107P; H132F; A133R; R146L; W147K; V153S; K163L; V177L; | I41L; W57Y; D70A; D107P; H132F; F163L; I314N; S398V; | Nd | + | nd |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| | R211K; P233T; A235P; P244T; M294V; I314N; P318D; A323T; S324G; A383V; T391A; S398V; C424A; F427Y; E451D; | E451D; | | | |
| 83/84 | A9T; G18A; D21H; V31M; I41L; N45H; R47N; W57Y; F86Y; A133R; R146L; W147K; V153S; K163L; V177L; R211K; P233T; A235P; P244T; M294V; E315G; P318D; A323T; S324G; A383V; T391A; S398V; L423I; C424A; F427Y; | I41L; R47N; W57Y; F163L; E315G; S398V; L423I; | Nd | + | nd |
| 85/86 | A9T; G18A; D21H; V31M; I41L; N45H; W57Y; F86Y; A133R; R146L; W147K; V153S; K163L; V177L; R211K; P233T; A235P; P244T; M294V; E315G; P318D; A323T; S324G; A383V; T391A; S398V; C424A; F427Y; | I41L; W57Y; F163L; E315G; S398V; | + | + | nd |
| 87/88 | A9T; G18A; D21H; V31M; I41L; N45H; W57Y; F86Y; D107P; H132F; A133R; R146L; W147K; V153S; V177L; R211K; P233T; A235P; P244T; M294V; E315G; P318D; A323T; S324G; A383V; T391A; G395P; S398W; C424A; F427Y; | I41L; W57Y; D107P; H132F; F163L; E315G; G395P; S398W; | + | + | nd |
| 89/90 | A9T; G18A; D21H; V31M; I41L; N45H; F86Y; D107P; H132F; A133R; R146L; W147K; V153S; K163L; V177L; R211K; P233T; A235P; P244T; M294V; P318D; A323T; S324G; A383V; T391A; S398V; C424A; F427Y; E451D; | I41L; D107P; H132F; F163L; S398V; E451D; | + | + | nd |
| 91/92 | A9T; G18A; D21H; V31M; I41L; N45H; W57Y; F86Y; D107P; H132F; A133R; R146L; W147K; V153S; K163L; V177L; R211K; P233T; A235P; P244T; M294V; I314N; E315G; P318D; A323T; S324G; A383V; T391A; S398V; L423I; C424A; F427Y; E451D; | I41L; W57Y; D107P; H132F; F163L; I314N; E315G; S398V; L423I; E451D; | + | + | nd |
| 93/94 | A9T; G18A; D21H; V31M; I41L; N45H; W57Y; F86Y; D107P; H132F; A133R; R146L; W147K; V153S; K163L; V177L; R211K; P233T; A235P; P244T; M294V; E315G; P318D; A323T; S324G; A383V; T391A; S398V; L423I; C424A; F427Y; | I41L; W57Y; D107P; H132F; F163L; E315G; S398V; L423I; | Nd | + | nd |
| 95/96 | A9T; G18A; D21H; V31M; I41L; N45H; W57Y; D70A; F86Y; D107P; H132F; A133R; R146L; W147K; V153S; K163L; V177L; R211K; P233T; A235P; P244T; M294V; I314N; P318D; A323T; S324G; A383V; T391A; S398W; Q419S; C424A; F427Y; | I41L; W57Y; D70A; D107P; H132F; F163L; I314N; S398W; Q419S; | Nd | + | nd |
| 97/98 | A9T; G18A; D21H; V31S; N45H; W57F; F86Y; A133R; R146L; W147K; V153S; K163I; V177L; R211K; P233T; A235P; P244T; M294V; I314N; P318D; A323T; S324G; A346L; A383V; T391A; G395P; S398W; C424A; F427Y; E451D; | M31S; W57F; L163I; I314N; A346L; G395P; S398W; E451D; | + | + | + |
| 99/100 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398L; Q419S; C424A; F427Y; | M31S; W57F; L163I; E315G; A346L; S398L; Q419S; | + | + | nd |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 101/102 | A9T; G18A; D21H; V31S; I41L; N45H; W57F; F86Y; R88A; A133R; R146L; W147K; V153S; K163I; V168S; V177L; R211K; P233T; A235P; P244T; M294V; P318D; A323T; S324G; A346L; A383V; T391A; S398V; C424A; F427Y; E451D; | M31S; I41L; W57F; R88A; L163I; V168S; A346L; S398V; E451D; | Nd | + | nd |
| 103/104 | A9T; G18A; D21H; V31S; N45H; W57F; F86Y; A133R; R146L; W147K; V153S; K163L; V168S; V177L; R211K; P233T; A235P; P244T; M294V; E315G; P318D; A323T; S324G; A346L; A383V; T391A; S398V; Q419S; C424A; F427Y; | M31S; W57F; F163L; V168S; E315G; A346L; S398V; Q419S; | + | + | nd |
| 105/106 | A9T; G18A; D21H; V31S; N45H; W57F; F86Y; A133R; R146L; W147K; V153S; K163L; V177L; R211K; P233T; A235P; P244T; M294V; I314N; P318D; A323T; S324G; A383V; T391A; S398W; C424A; F427Y; | M31S; W57F; F163L; I314N; S398W; | + | + | nd |
| 107/108 | A9T; G18A; D21H; V31S; N45H; W57F; F86Y; A133R; R146L; W147K; V153S; K163L; V177L; R211K; P233T; A235P; P244T; M294V; P318D; A323T; S324G; A383V; T391A; C424A; F427Y; | M31S; W57F; F163L; | + | + | nd |
| 109/110 | A9T; G18A; D21H; V31S; N45H; W57F; F86Y; A133R; R146L; W147K; V153S; K163I; V168K; V177L; R211K; P233T; A235P; P244T; M294V; E315G; P318D; A323T; S324G; A346L; A383V; T391A; S398W; C424A; F427Y; E451D; | M31S; W57F; L163I; V168K; E315G; A346L; S398W; E451D; | + | + | nd |
| 111/112 | A9T; Y14V; G18A; D21H; V31S; N45H; W57F; F86Y; A133R; R146L; W147K; V153S; K163L; V177L; R211K; P233T; A235P; P244T; M294V; I314N; P318D; A323T; S324G; A346L; A383V; T391A; S398V; C424A; F427Y; | Y14V; M31S; W57F; F163L; I314N; A346L; S398V; | + | + | nd |
| 113/114 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398L; C424A; F427Y; | M31S; W57F; L163I; E315G; A346L; S398L; | + | + | nd |
| 115/116 | A9T; G18A; D21H; V31S; N45H; F86Y; A133R; R146L; W147K; V153S; K163I; V177L; R211K; P233T; A235P; P244T; M294V; E315G; P318D; A323T; S324G; A346L; A383V; T391A; S398V; C424A; F427Y; E451D; | M31S; L163I; E315G; A346L; S398V; E451D; | + | + | nd |
| 117/118 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398W; C424A; F427Y; E451D; | M31S; W57F; L163I; E315G; A346L; S398W; E451D; | + | + | nd |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 119/120 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398V; C424A; F427Y; | M31S; W57F; L163I; E315G; A346L; S398V; | 188, 190, 193, 194, 196, | + | nd |
| 121/122 | A9T; G18A; D21H; V31M; N45H; W57F; F86Y; A133R; R146L; W147K; V153S; K163L; V177L; R211K; P233T; A235P; P244T; M294V; P318D; A323T; S324G; A346L; A383V; T391A; S398L; C424A; F427Y; | W57F; F163L; A346L; S398L; | Nd | + | + |
| 123/124 | A9T; G18A; D21H; V31M; N45H; W57F; F86Y; A133R; R146L; W147K; V153S; K163L; V168K; V177L; R211K; P233T; A235P; P244T; M294V; I314N; E315G; P318D; A323T; S324G; A346L; A383V; T391A; S398V; C424A; F427Y; | W57F; F163L; V168K; I314N; E315G; A346L; S398V; | + | + | ++ |
| 125/126 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398V; L423I; C424A; F427Y; | M31S; W57F; L163I; E315G; A346L; S398V; L423I; | + | + | nd |
| 127/128 | A9T; G18A; D21H; V31S; N45H; W57F; F86Y; A133R; R146L; W147K; V153S; K163L; V177L; R211K; P233T; A235P; P244T; M294V; I314N; E315G; P318D; A323T; S324G; A346L; A383V; T391A; S398V; Q419S; C424A; F427Y; | M31S; W57F; F163L; I314N; E315G; A346L; S398V; Q419S; | + | + | nd |
| 129/130 | A9T; Y14V; G18A; D21H; H26R; V31M; N45H; F86Y; A133R; R146L; W147K; V153S; K163I; V177L; R211K; P233T; A235P; P244T; S284A; M294V; P318D; A323T; S324G; A383V; T391A; S400G; L417M; S420N; C424A; F427Y; | Y14V; H26R; L163I; S284A; S400G; L417M; S420N; | Nd | nd | + |
| 131/132 | A9T; Y14V; G18A; D21H; V31M; N45H; F86Y; A133R; R146L; W147K; V153S; K163L; L173A; V177L; R211K; P233T; A235P; P244T; M294V; P318D; A323T; S324G; A383V; T391A; S400G; S420N; C424A; F427Y; | Y14V; F163L; L173A; S400G; S420N; | + | + | ++ |
| 133/134 | A9T; Y14V; G18A; D21H; V31M; N45H; F86Y; Y113L; A133R; R146L; W147K; V153S; K163L; V177L; R211K; P233T; A235P; P244T; S284A; M294V; P318D; A323T; S324G; A383V; T391A; C424V; F427Y; | Y14V; Y113L; F163L; S284A; A424V; | + | + | ++ |
| 135/136 | A9T; Y14V; G18A; D21H; V31M; N45H; F86Y; R88L; A133R; R146L; W147K; V153S; K163L; V177L; R211K; P233T; A235P; P244T; M294V; P318D; A323T; S324H; A383V; T391A; S400G; L417M; C424A; F427Y; | Y14V; R88L; F163L; G324H; S400G; L417M; | + | + | nd |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a,b] | Stability[b] | Product Tolerance[c,d] |
|---|---|---|---|---|---|
| 137/138 | A9T; Y14V; G18A; D21H; H26R; V31M; N45H; W57F; F86Y; Y113L; A133R; R146L; W147K; V153S; K163L; V177L; R211K; P233T; A235P; P244T; S284A; M294V; P318D; A323T; S324G; A383V; T391A; C424A; F427Y; | Y14V; H26R; W57F; Y113L; F163L; S284A; | Nd | nd | + |
| 139/140 | A9T; Y14V; G18A; D21H; H26R; V31M; N45H; F86Y; A133R; R146L; W147K; V153S; K163L; V177L; R211K; P233T; A235P; P244T; S284A; M294V; P318D; A323T; S324G; T391A; S400G; C424A; F427Y; | Y14V; H26R; F163L; S284A; V383A; S400G; | Nd | nd | ++ |
| 141/142 | A9T; Y14V; G18A; D21H; H26R; V31M; N45H; F86Y; Y113L; A133R; R146L; W147K; V153S; K163L; V177L; R211K; P233T; A235P; P244T; M294V; P318D; A323T; S324G; T391A; C424V; F427Y; | Y14V; H26R; Y113L; F163L; V383A; A424V; | + | + | nd |
| 143/144 | A9T; G18A; D21H; V31M; N45H; F86Y; R88L; A133R; R146L; W147K; V153S; K163L; V177L; R211K; P233T; A235P; P244T; M294V; P318D; A323T; S324G; A383V; T391A; C424A; F427Y; | R88L; F163L; | + | + | #VALUE! |
| 145/146 | A9T; Y14V; G18A; D21H; H26R; V31M; N45H; F86Y; A133R; R146L; W147K; N148Q; V153S; K163I; V177L; R211K; P233T; A235P; P244T; S284A; M294V; P318D; A323T; S324G; T391A; S400G; S420N; C424A; F427Y; | Y14V; H26R; N148Q; L163I; S284A; V383A; S400G; S420N; | Nd | + | ++ |
| 147/148 | A9T; Y14V; G18A; D21H; V31M; V33T; N45H; W57F; F86Y; Y113L; A133R; R146L; W147K; V153S; K163L; V177L; R211K; P233T; A235P; P244T; M294V; P318D; A323T; S324G; A383V; T391A; C424A; F427Y; | Y14V; V33T; W57F; Y113L; F163L; | + | + | nd |
| 149/150 | A9T; Y14V; G18A; D21H; V31M; N45H; W57F; F86Y; R88L; Y113L; A133R; R146L; W147K; N148Q; V153S; K163I; L173A; V177L; R211K; P233T; A235P; P244T; M294V; P318D; A323T; S324G; T391A; S400G; C424A; F427Y; | Y14V; W57F; R88L; Y113L; N148Q; L163I; L173A; V383A; S400G; | Nd | + | nd |
| 151/152 | A9T; G18A; D21H; V31M; N45H; W57F; F86Y; A133R; R146L; W147K; V153S; K163L; V177L; R211K; P233T; A235P; P244T; M294V; P318D; A323T; S324G; A383V; T391A; C424A; F427Y; | W57F; F163L; | Nd | + | + |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a, b] | Stability[b] | Product Tolerance[c, d] |
|---|---|---|---|---|---|
| 153/154 | A9T; Y14V; G18A; D21H; H26R; V31M; N45H; F86Y; A133R; R146L; W147K; V153S; K163L; V177L; R211K; P233T; A235P; P244T; S284A; M294V; P318D; A323T; S324H; A383V; T391A; S400G; C424A; F427Y; | Y14V; H26R; F163L; S284A; G324H; S400G; | + | + | nd |

[a] HTP Assay Condition 1: Cells grown in 96 well plates were lysed with 200 vL of Lysis Buffer (1 mg/mL lysozyme, 0.5 mg/mL polymyxin B sulfate, 1 mM PLP, 0.1M triethanolamine (TEA), pH 7.0). The reaction conditions comprised: 10 g/L (44.4 mM) Compound (IA); 1 mM pyridoxal-5-phosphate (PLP); 2M isopropylamine (IPM), pH 7.0; 100 mM triethanolamine (TEA), pH 7.0; 5% PEG 200 v/v; 10 vL Lysate; and 50° C. for 24 h.

[b] HTP Assay Condition 2: Cells grown in 96 well plates were lysed with 400 vL of Lysis Buffer (1 mg/mL lysozyme, 0.5 mg/mL polymyxin B sulfate, 1 mM PLP, 0.1M triethanolamine (TEA), pH 7.0). The reaction conditions comprised: 10 g/L (44.4 mM) Compound (IA); 1 mM pyridoxal-5-phosphate (PLP); 2M isopropylamine (IPM), pH 7.0; 100 mM triethanolamine (TEA), pH 7.0; 5% PEG 200 v/v; 10 vL Lysate; and 50° C. for 24 h.

[c] Stability Assay conditions: 10 g/L (44.4 mM) Compound (IA); 1 mM pyridoxal-5-phosphate (PLP); 2M isopropylamine (IPM), pH 7.0; 100 mM triethanolamine (TEA), pH 7.0; 5% PEG 200 v/v; 10 vL Lysate (prepared according to HTP Assay Condition 1 or 2); and 55° C. for 24 h. Lysates were prepared according to HTP Assay Condition 1 (for SEQ ID NO: 4-90) or HTP Assay Condition 2 (for SEQ ID NO: 92-230).

[d] Product Inhibition Assay Condition 1: 10 g/L (44.4 mM) Compound (IA); 14 g/L Compound (IIA); 1 mM pyridoxal-5-phosphate (PLP); 2M isopropylamine (IPM), pH 7.0; 100 mM triethanolamine (TEA), pH 7.0; 5% PEG 200 v/v; 10 vL Lysate; and 50° C. Lysates were prepared according to HTP Assay Condition 1.

[e] Product Inhibition Assay Condition 2: 10 g/L (44.4 mM) Compound (IA); 16 g/L Compound (IIA); 1 mM pyridoxal-5-phosphate (PLP); 2M isopropylamine (IPM), pH 7.0; 100 mM triethanolamine (TEA), pH 7.0; 5% PEG 200 v/v; 10 vL Lysate; and 50° C. Lysates were prepared according to HTP Assay Condition 2.

nd: not determined

TABLE 2B

Engineered Polypeptides and Relative Enzyme improvements Using Shake Flask and DSP Preparations

| SEQ ID NO: | Active Mutations (relative to Wild-type of SEQ ID NO: 2) | Active Mutations (relative to SEQ ID NO: 4) | Shake Flask % ee | Shake Flask Activity[a] | DSP % ee | DSP Activity[b] |
|---|---|---|---|---|---|---|
| 1/2 | n/a | | nd | Nd | nd | nd |
| 3/4 | A9T; G18A; D21H; V31M; N45H; F86Y; A133R; R146L; VV147K; V153S; K163F; V177L; R211K; P233T; A235P; P244T; M294V; P318D; A323T; S324G; A383V; T391A; C424A; F427Y | | "Control" | "Control" | "Control" | "Control" |
| 5/6 | A9T; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y; | F163L | 99.7 | + | nd | nd |
| 7/8 | A9T; G18A; D21H; V31M; N45H; F86Y; A133R; R146L; W147K; V153S; K163I; V177L; R211K; P233T; A235P; P244T; M294V; P318D; A323T; S324G; A383V; T391A; C424A; F427Y | F163I | 99.5 | + | nd | nd |
| 45/46 | A9T; Y14V; G18A; D21H; H26R; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y | Y14V; H26R; W57F; R88L; Y113L; N148Q; L163I | 99.6 | + | 99.4 | + |
| 99/100 | A9T; G18A; D21H; V31S; N45H; W57F; F86Y; A133R; R146L; W147K; V153S; K163I; V177L; R211K; P233T; A235P; P244T; | M31S; W57F; L163I; E315G; A346L; S398L; Q419S | 99.8 | + | nd | nd |

TABLE 2B-continued

Engineered Polypeptides and Relative Enzyme improvements
Using Shake Flask and DSP Preparations

| SEQ ID NO: | Active Mutations (relative to Wild-type of SEQ ID NO: 2) | Active Mutations (relative to SEQ ID NO: 4) | Shake Flask % ee | Shake Flask Activity[a] | DSP % ee | DSP Activity[b] |
|---|---|---|---|---|---|---|
| | M294V; E315G; P318D; A323T; S324G; A346L; A383V; T391A; S398L; Q419S; C424A; F427Y | | | | | |
| 111/112 | A9T; Y14V; G18A; D21H; V31S; N45H; W57F; F86Y; A133R; R146L; W147K; V153S; K163L; V177L; R211K; P233T; A235P; P244T; M294V; I314N; P318D; A323T; S324G; A346L; A383V; T391A; S398V; C424A; F427Y | Y14V; M31S; W57F; F163L; I314N; A346L; S398V | 99.7 | + | nd | nd |
| 133/134 | A9T; Y14V; G18A; D21H; V31M; N45H; F86Y; Y113L; A133R; R146L; W147K; V153S; K163L; V177L; R211K; P233T; A235P; P244T; S284A; M294V; P318D; A323T; S324G; A383V; T391A; C424V; F427Y | Y14V; Y113L; F163L; S284A; A424V | nd | Nd | 99.8 | + |
| 143/144 | A9T; G18A; D21H; V31M; N45H; F86Y; R88L; A133R; R146L; W147K; V153S; K163L; V177L; R211K; P233T; A235P; P244T; M294V; P318D; A323T; S324G; A383V; T391A; C424A; F427Y | R88L; F163L | 99 | Nd | nd | nd |

[a] Shake Flask Assay Conditions: 25 g/L (or 50 or 100 g/L) Compound (IA); 1 mM pyridoxal-5-phosphate (PLP); 2M isopropylamine (IPM), pH 7.0; 5% v/v PEG200; 100 mM triethanolamine (TEA), pH 7.0; 2 g/L protein of transaminase-containing shake flask preparation; and 50° C. for a reaction time of 24 h.
[b] DSP Assay Conditions: 25 g/L (or 50 or 100 g/L) Compound (IA); 1 mM pyridoxal-5-phosphate (PLP); 2M isopropylamine (IPM), pH 7; 5% v/v PEG200; 100 mM triethanolamine (TEA), pH 7; 2 g/L protein from transaminase-containing DSP preparation; and 50° C. for a reaction time of 24 h.

From an inspection of the exemplary polypeptides useful in the methods of the present invention, improvements in enzyme properties are associated with residue differences as compared to SEQ ID NO:4 at residue positions X14; X26; X31; X33; X41; X47; X57; X70; X86; X88; X107; X113; X132; X148; X163; X168; X173; X203; X250; X284; X314; X315; X324; X346; X395; X398; X400; X417; X419; X420; X423; X424; X448; and X451. The specific residue differences at each of these positions that are associated with the improved properties include: X14V; X26R; X31S; X33T; X41L; X47N; X57F; X57Y; X70A; X86D; X88A; X88L; X107P; X113L; X113V; X132F; X148Q; X148R; X163I; X163L; X163R; X163V; X168K; X168S; X173A; X203S; X250A; X284A; X314N; X315G; X324H; X346L; X395P; X398L; X398V; X398W; X400G; X417M; X419S; X420N; X423I; X424V; X448E; and X451D.

Accordingly, in some embodiments, the engineered transaminase polypeptide useful in the methods of the instant disclosure are capable of converting substrate Compound (IA), 1-(1H-5-fluoro-6-chloro-indol-3-yl)propan-2-one, to the product Compound (IIA), (S)-1-(1H-5-fluoro-6-chloro-indol-3-yl)propan-2-amine with improved properties as compared to SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.

In some embodiments, the engineered transaminase polypeptide useful in the instantly disclosed methods is capable of converting substrate Compound (IA) to the product Compound (IIA) with improved properties as compared to SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:4 and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the engineered transaminase polypeptides are capable of carrying out the conversion with the enantioselectivities described above, e.g., ≥90% ee.

In some embodiments, the transaminase polypeptide useful in the instantly disclosed methods is capable of converting substrate Compound (IA) to product Compound (IIA) with improved properties as compared to SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the reference sequence is selected from SEQ ID NO: 4, 8, 14, 16, 132, 134, and 146. In some embodiments, the reference sequence is SEQ ID NO:4. In some embodiments, the reference sequence is SEQ ID NO:8. In some embodiments, the reference sequence is SEQ ID NO:134. In some embodiments, the reference sequence is SEQ ID NO:146.

In some embodiments, the transaminase polypeptide capable of converting substrate Compound (IA) to product Compound (IIA) with improved properties as compared to SEQ ID NO:4, comprises an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and having one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the amino acid sequence is selected from SEQ ID NO: 4, 8, 14, 16, 132, 134, and 146. In some embodiments, the amino acid sequence is SEQ ID NO:4. In some embodiments, the amino acid sequence is SEQ ID NO:8. In some embodiments, the amino acid sequence is SEQ ID NO:134. In some embodiments, the amino acid sequence is SEQ ID NO:146.

In some embodiments, the engineered transaminase polypeptide is capable of converting the substrate Compound (IA) to the product Compound (IIA) with at least 1.2 fold the activity relative to SEQ ID NO:4 comprises an amino acid sequence selected from: SEQ ID NO: 6, 8, 10, 12, 14, 16, 22, 24, 28, 30, 32, 48, 52, 56, 62, 64, 66, 68, 86, 88, 90, 92, 98, 100, 104, 106, 108, 110, 112, 114, 116, 118, 124, 126, 128, 132, 134, 136, 142, 144, 148, and 154.

In some embodiments, the engineered transaminase polypeptide is capable of converting the substrate Compound (IA) to the product Compound (IIA) with at least 5 fold the activity relative to SEQ ID NO:4 and comprises an amino acid sequence having one or more residue differences selected from: X14V, X26R; X33T; X88A/L; X163I/L; and X284A.

In some embodiments, the engineered transaminase polypeptide useful in the instantly disclosed methods is capable of converting the substrate Compound (IA) to the product Compound (IIA) with at least 5 fold the activity relative to SEQ ID NO:4 comprises an amino acid sequence selected from: SEQ ID NO: 6, 8, 10, 14, 16, 22, 24, 28, 30, 32, 48, 52, 56, 62, 64, 86, 88, 90, 92, 98, 100, 104, 106, 108, 110, 112, 114, 116, 118, 124, 126, 128, 132, 134, 136, 142, 144, 148, and 154.

In some embodiments, the engineered transaminase polypeptide has at least 1.2 fold, 1.5 fold, 2 fold, 3 fold, 4 fold, 5 fold, or more refractoriness to inhibition by 1-(1H-5-fluoro-6-chloro-indol-3-yl)propan-2-amine, in particular (S)-1-(1H-5-fluoro-6-chloro-indol-3-yl)propan-2-amine, as compared to the polypeptide represented by SEQ ID NO:4 in the conversion of Compound (IA) to Compound (IIA). Generally, the increase in refractoriness or resistance to inhibition by the product compound can be measured under HTP assay conditions in presence of 14 g/L or 16 g/L of Compound (IIA), as described in Table 2A and 2B and the Examples. In some embodiments, the engineered transaminase polypeptide having at least 1.2 fold or greater refractoriness to inhibition by 1-(1H-5-fluoro-6-chloro-indol-3-yl)propan-2-amine comprises an amino acid sequence having one or more residue differences as compared to SEQ ID NO:4 selected from: X26R; X70A; X86D; X88A/L; X132F; X163L; X315G; X395P; X398L; and X419S.

In some embodiments, the engineered transaminase polypeptide with improved properties in the conversion of Compound (IA) to Compound (IIA) has an amino acid sequence comprising a sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In some embodiments, the engineered transaminase capable of converting Compound (IA) to Compound (IIA) under suitable reaction conditions, comprises an amino acid sequence having at least 80%, 85%, 86%, 87%, 88%, 89%, 90%, 91%, 92%, 93%, 94% 95%, 96%, 97%, 98%, or 99% identity to one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and the amino acid residue differences as compared to SEQ ID NO:4 present in any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, as provided in Tables 2A and 2B.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the transaminase polypeptides can be bound on a physical substrate. The transaminase polypeptide can be bound non-covalently or covalently on a physical substrate such that they retain their improved activity, stereoselectivity, product tolerance, stability, and/or other improved properties relative to the reference polypeptide of SEQ ID NO: 4. In such embodiments, the immobilized polypeptides can facilitate the biocatalytic conversion of the suitable ketone substrates, e.g, Compound (IA) or structural analogs thereof, to the corresponding amine product, e.g., Compound (IIA) or corresponding structural analogs, and after the reaction is complete are easily retained (e.g., by retaining beads on which polypeptide is immobilized) and then reused or recycled in subsequent reactions. Such immobilized enzyme processes allow for further efficiency and cost reduction. Methods of enzyme immobilization are well-known in the art. Various methods for conjugation to substrates, e.g., membranes, beads, glass, etc. are described in, among others, Hermanson, G. T., Bioconjugate Techniques, Second Edition, Academic Press; (2008), and Bioconjugation Protocols: Strategies and Methods, In Methods in Molecular Biology, C. M. Niemeyer ed., Humana Press (2004); the disclosures of which are incorporated herein by reference.

Polynucleotides Encoding Engineered Transaminases, Expression Vectors and Host Cells In another aspect, the present disclosure provides polynucleotides encoding the engineered transaminase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered transaminase can be introduced into appropriate host cells to express the corresponding transaminase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved transaminase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2A and 2B, and disclosed in the sequence listing incorporated by reference herein as SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. In some embodiments, all codons need not be replaced to optimize the codon usage of the transaminases since the natural sequence will comprise preferred codons and because use of preferred codons may not be required for all amino acid residues. Consequently, codon optimized polynucleotides encoding the transaminase enzymes may contain preferred codons at about 40%, 50%, 60%, 70%, 80%, or greater than 90% of codon positions of the full length coding region.

An isolated polynucleotide encoding an improved transaminase polypeptide may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, $3^{rd}$ Ed., Cold Spring Harbor Laboratory Press; and Current Protocols in Molecular Biology, Ausubel. F. ed., Greene Pub. Associates, 1998, updates to 2006.

In the embodiments herein, the improved polypeptides and corresponding polynucleotides can be obtained using methods used by those skilled in the art. The parental polynucleotide sequence encoding the wild-type polypeptide of Vibrio fluvialis is described in Shin et al., 2003, Appl. Microbiol. Biotechnol. 61(5-6):463-471, and methods of generating engineered transaminase polypeptides with improved stability and substrate recognition properties are disclosed in patent application publications WO2010081053 and US20100209981, incorporated herein by reference.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources.

Accordingly, in some embodiments, a method for preparing the engineered transaminases polypeptide can comprise: (a) synthesizing a polynucleotide encoding a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154 and having one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.; and (b) expressing the transaminase polypeptide encoded by the polynucleotide.

The expressed engineered transaminase can be measured for the desired improved property, e.g., activity, enantioselectivity, stability, and product tolerance, in the conversion of compound (IA) to compound (IIA) by any of the assay conditions described herein.

In some embodiments, any of the engineered transaminase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the transaminase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved transaminase enzymes. For affinity chromatography purification, any antibody which specifically binds the transaminase polypeptide may be used. For the production of antibodies, various host animals, including but not limited to rabbits, mice, rats, etc., may be immunized by injection with a transaminase polypeptide, or a fragment thereof. The transaminase polypeptide or fragment may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Methods of Using the Engineered Transaminase Enzymes

In another aspect, the transaminases described herein can be used in a process for carrying out transaminase reactions in which an amino group from an amino donor is transferred to an amino acceptor, e.g., ketone substrate, to produce an amine. Use of a prochiral ketone acceptor can result in the production of a chiral amine in enantiomeric excess. Generally, the process for performing the transamination reaction comprises contacting or incubating an amino donor and an amino acceptor with an engineered transaminase polypeptide of the disclosure under reaction conditions suitable for converting the amino acceptor to an amine.

In some embodiments, the transaminases can be used in the conversion of substrate compound of formula (I) to product compound of formula (II). Accordingly, in some embodiments, a process for preparing the compound of formula (II) in enantiomeric excess comprises contacting the compound of formula (I) in the presence of an amino donor under suitable reaction conditions with an engineered transaminase polypeptide described herein. In some embodiments of the process, the compound of formula (II) can be formed in at least 90%, 91%, 92%, 93%, 94%, 95%, 96%, 97%, 98%, 99% or greater enantiomeric excess.

For the foregoing processes, any of the engineered transaminases described herein can be used. By way of example and without limitation, in some embodiments, the process can use an engineered transaminases polypeptide comprising comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the reference sequence is selected from SEQ ID NO: 4, 8, 14, 16, 132, 134, and 146. In some embodiments, the reference sequence is SEQ ID NO:4. In some embodiments, the reference sequence is SEQ ID NO:8. In some embodiments, the reference sequence is SEQ ID NO:134. In some embodiments, the reference sequence is SEQ ID NO:146.

In some embodiments, exemplary transaminases capable of carrying out the processes herein can be a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154. Guidance on the choice and use of the engineered transaminases is provided in the descriptions herein, for example Table 2 and the Examples.

In the embodiments herein and illustrated in the Examples, various ranges of suitable reaction conditions that can be used in the processes, including but not limited, to ranges of amino donor, pH, temperature, buffer, solvent system, substrate loading, polypeptide loading, cofactor loading, pressure, and reaction time. Further suitable reaction conditions for carrying out the process for biocatalytic conversion of substrate compounds to product compounds using an engineered transaminase polypeptide described herein can be readily optimized in view of the guidance provided herein by routine experimentation that includes, but is not limited to, contacting the engineered transaminase polypeptide and substrate compound under experimental reaction conditions of concentration, pH, temperature, solvent conditions, and detecting the product compound.

In the embodiments described herein, the transaminase polypeptide uses an amino donor to form the product compounds. In some embodiments, the amino donor in the reaction condition can be selected from isopropylamine (also referred to herein as "IPM"), putrescine, L-lysine, α-phenethylamine, D-alanine. L-alanine, or D,L-alanine, or D,L-ornithine. In some embodiments, the amino donor is selected from the group consisting of IPM, putrescine, L-lysine. D- or L-alanine. In some embodiments, the amino donor is IPM. In some embodiments, the suitable reaction conditions comprise the amino donor, in particular IPM, present at a concentration of at least about 0.1 to about 3.0 M, 0.2 to about 2.5 M. about 0.5 to about 2 M or about 1 to about 2 M. In some embodiments, the amino donor is present at a concentration of about 0.1, 0.2, 0.3, 0.4, 0.5, 0.6, 0.7, 0.8, 1, 1.5, 2, 2.5 or 3 M. Higher. concentrations of amino donor, e.g., IPM, can be used to shift the equilibrium towards amine product formation.

Suitable reaction conditions using the engineered transaminase polypeptides also typically comprise a cofactor. Cofactors useful in the processes using the engineered transaminase enzymes include, but are not limited to, pyridoxal-5'-phosphate (also known as pyridoxal-phosphate, PLP, P5P), pyridoxine (PN), pyridoxal (PL), pyridoxamine (PM), and their phosphorylated counterparts; pyridoxine phosphate (PNP), and pyridoxamine phosphate (PMP). In some embodiments, the cofactor PLP is present naturally in the cell extract and does not need to be supplemented. In some embodiments of the methods, the suitable reaction conditions comprise cofactor added to the enzyme reaction mixture, for example, when using partially purified, or purified transaminase enzyme. In some embodiments, the suitable reaction conditions can comprise the presence of a cofactor selected from PLP, PN, PL, PM, PNP, and PMP, at a concentration of about 0.1 g/L to about 10 g/L, about 0.2 g/L to about 5 g/L, about 0.5 g/L to about 2.5 g/L. In some embodiments, the reaction conditions comprise a PLP concentration of about 0.1 g/L or less, 0.2 g/L or less, 0.5 g/L or less, 1 g/L or less, 2.5 g/L or less, 5 g/L or less, or 10 g/L or less. In some embodiments, the cofactor can be added either at the beginning of the reaction and/or additional cofactor is added during the reaction.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, 5 to about 150 g/L, about 10 to about 100 g/L, 20 to about 100 g/L or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater.

The improved activity and/or stereoselectivity of the engineered transaminase polypeptides disclosed herein provides for processes wherein higher percentage conversion can be achieved with lower concentrations of the engineered polypeptide. In some embodiments of the process, the suitable reaction conditions comprise an engineered polypeptide concentration of about 0.01 to about 50 g/L; about 0.05 to about 50 g/L; about 0.1 to about 40 g/L; about 1 to about 40 g/L; about 2 to about 40 g/L; about 5 to about 40 g/L; about 5 to about 30 g/L; about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the transaminase polypeptide is concentration at about 0.01, 0.05, 0.1, 0.2, 0.5, 1, 2, 5, 10, 15, 20, 25, 30, 35, 40, or 50 g/L.

During the course of the transamination reactions, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, carbonate, phosphate, triethanolamine buffer, and the like. In some embodiments, the buffer is borate. In some embodiments of the process, the suitable reaction conditions comprise a buffer solution of triethanolamine, where the triethanolamine concentration is from about 0.01 to about 0.4 M. 0.05 to about 0.4 M. 0.1 to about 0.3 M. or about 0.1 to about 0.2 M. In some embodiments, the reaction condition comprises a triethanolamine concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the process, the reaction conditions can comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH comprise a pH from about 6 to about 12, pH from about 6 to about 10, pH from about 6 to about 8, pH from about 7 to about 10, pH from about 7 to about 9, or pH from about 7 to about 8. In some embodiments, the reaction conditions comprise a solution pH of about 6, 6.5, 7, 7.5, 8, 8.5, 9, 9.5, 10, 10.5, 11, 11.5, 12.

In the embodiments of the processes herein, a suitable temperature can be used for the reaction conditions, for example, taking into consideration the increase in reaction rate at higher temperatures, and the activity of the enzyme during the reaction time period. For example, the engineered polypeptides of the present disclosure have increased stability relative to naturally occurring transaminase polypeptide e.g., the wild type polypeptide of SEQ ID NO: 2, which allow the engineered polypeptides to be used at higher temperatures for increased conversion rates and improved substrate solubility characteristics for the reaction. Accordingly, in some embodiments, the suitable reaction conditions comprise a temperature of about 10° C. to about 70° C., about 10° C. to about 65° C., about 15° C. to about 60° C., about 20° C. to about 60° C., about 20° C. to about 55° C., about 30° C. to about 55° C., or about 40° C. to about 50° C. In some embodiments, the suitable reaction conditions comprise a temperature of about 10° C., 15° C., 20° C., 25° C., 30° C., 35° C., 40° C., 45° C., 50° C., 55° C., 60° C., 65° C., or 70° C. In some embodiments, the temperature during the enzymatic reaction can be maintained at a temperature throughout the course of the reaction. In some embodiments, the temperature during the enzymatic reaction can be adjusted over a temperature profile during the course of the reaction.

The processes of the disclosure are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes using the engineered transaminase polypeptides are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl t butyl ether (MTBE), toluene, and the like), ionic or polar solvents (e.g., 1 ethyl 4 methylimidazolium tetrafluoroborate, 1 butyl 3 methylimidazolium tetrafluoroborate, 1 butyl 3 methylimidazolium hexafluorophosphate, glycerol, polyethylene glycol, and the like). In some embodiments, the co-solvent can be a polar solvent, such as a polyol, dimethylsulfoxide. DMSO, or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the transaminase enzyme under the reaction conditions. Appropriate co-solvent systems can be readily identified by measuring the enzymatic activity of the specified engineered transaminase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises a polyol solvent, particularly glycols. Examples of suitable polyol solvents include, by way of example and not limitation, polyethylene glycol, polyethylene glycol methyl ether, diethylene glycol dimethyl ether, triethylene glycol dimethyl ether, and polypropylene glycol. In some embodiments, the aqueous co-solvent comprises polyethylene glycol, which is available in different molecular weights. Particularly useful are lower molecular weight glycols, such as PEG200 to PEG600. Accordingly, in some embodiments, the aqueous co-solvent comprises PEG200 of about 1% to about 40% v/v; about 1% to about 40% v/v; about 2% to about 40% v/v; about 5% to about 40% v/v; 2% to about 30% v/v; 5% to about 30% v/v; 1 to about 20% v/v; about 2% to about 20% v/v; about 5% to about 20% v/v; about 1% to about 10% v/v; about 2% to about 10% v/v. In some embodiments, the suitable reaction conditions comprises an aqueous co-solvent comprising PEG200 at about 1%, 2%, 5%, 10%, 15%, 20%; 25%; 30%; 35%; 35% or about 40% v/v.

In some embodiments of the process, the suitable reaction conditions comprise an aqueous co-solvent, where the co-solvent comprises DMSO at about 1% to about 80% (v/v), about 1 to about 70% (v/v), about 2% to about 60% (v/v), about 5% to about 40% (v/v), 10% to about 40% (v/v), 10% to about 30% (v/v), or about 10% to about 20% (v/v). In some embodiments of the process, the suitable reaction conditions comprise an aqueous co-solvent comprising DMSO at least about 1%, 5%, 10%, 15%, 20%, 25%, 30%, 35%, 40%, 45%, 50%, 55%, 60%, 65%, 70%, 75%, or 80% (v/v).

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the transaminase, and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The transamination reaction is generally allowed to proceed until further conversion of ketone substrate to amine product doe s not change significantly with reaction time, e.g., less than 10% of substrate being converted, or less than 5% of substrate being converted). In some embodiments, the reaction is allowed to proceed until there is complete or near complete conversion of substrate ketone to product amine. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and are often greater than about 97%. In some embodiments, the methods for preparing compounds of formula (II) using an engineered transaminase polypeptide under suitable reaction conditions results in at least about 91%, 92%, 93%, 94%, 95%, 96%, 97%, 98%, 99% or greater conversion of ketone substrate, e.g, compound of formula (I), to the amine product compound, e.g., compound of formula (II) in about 48 h or less, in about 36 h or less, in about 24 h or less, or even less time.

In some embodiments of the process, the suitable reaction conditions comprise a substrate loading of substrate compound of at least about 20 g/L, 30 g/L, 40 g/L, 50 g/L, 60 g/L, 70 g/L, 100 g/L, or more, and wherein the method results in at least about 91%, 92%, 93%, 94%, 95%, 96%, 97%, 98%, 99% or greater conversion of substrate compound to product compound in about 48 h or less, in about 36 h or less, or in about 24 h or less.

The engineered transaminase polypeptides of the present disclosure when used in the process under suitable reaction conditions result in an enantiomeric excess of the chiral amine in at least 97%, 98, 99%, 99.1%, 99.2%, 99.3%, 99.4%, 99.5%, 99.6%, 99.7%, 99.8%, or 99.9%. e.e.

In a further embodiment of the methods for converting substrate compound to amine product compound using the engineered transaminase polypeptides, the suitable reaction conditions comprise an initial substrate loading to the reaction solution which is then contacted by the polypeptide. This reaction solution is the further supplemented with additional substrate of compound as a continuous addition over time at a rate of at least about 1 g/L/h, at least about 2 g/L/h, at least about 4 g/L/h, at least about 6 g/L/h, or higher. Thus, according to these suitable reaction conditions polypeptide is added to a solution having an initial substrate loading of at least about 20 g/L, 30 g/L, or 40 g/L. This addition of polypeptide is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the method, the suitable reaction conditions comprise addition of the polypeptide to a solution having an initial substrate loading of at least about 20 g/L, 30 g/L, or 40 g/L followed by addition of further substrate to the solution at a rate of about 2 g/L/h, 4 g/L/h, or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of ketone substrate to amine product of at least about 91%, 92%, 93%, 94%, 95%, 96%, 97%, 98%, 99% or greater. In some embodiments of this method, the further substrate added is in a solution comprising isopropylamine or isopropylamine acetate at a concentration of at least about 0.5 M, at least about 1.0 M. at least about 2.5 M. at least about 5.0 M, at least about 7.5 M. at least about 10.0 M.

In some embodiments of the processes, the transamination reaction using an engineered transaminase polypeptide can comprise the following suitable reaction conditions: (a) substrate loading at about 5 g/L to 200 g/L; (b) about 0.1 to 50 g/L of transaminases polypeptide; (c) about 0.1 to 4 M of isopropylamine (IPM); (d) about 0.1 to 10 g/L of pyridoxal phosphate (PLP) cofactor; (e) pH of about 6 to 9; and (f) temperature of about 30 to 60° C.

In some embodiments of the processes, the transamination reaction using an engineered transaminase polypeptide can comprise the following suitable reaction conditions: (a) substrate loading at about 5 to about 20 g/L; (b) about 0.05 to 2 g/L of transaminases polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine (TEA); (g) pH of about 6 to 8; and (h) temperature of about 45 to 55° C.

In some embodiments of the processes, the transamination reaction using an engineered transaminase polypeptide can comprise the following suitable reaction conditions: (a) substrate loading of about 25 to about 100 g/L; (b) about 0.5 to 10 g/L of transaminases polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine; (g) pH of about 6 to 8; and (h) temperature of about 45 to 55° C.

In some embodiments, additional reaction components or additional techniques carried out to supplement the reaction conditions. These can include taking measures to stabilize or prevent inactivation of the enzyme, reduce product inhibition, shift reaction equilibrium to product amine formation.

Accordingly, in some embodiments of the process for preparing an amine, such as a chiral amine, additional quantities of the amino acceptor can be added (up to saturation) and/or the amino acceptor (ketone) formed can be continuously removed from the reaction mixture. For example, a solvent bridge or a two phase co-solvent system can be used to move the amine product to an extraction solution, and thereby reduce inhibition by amine product and also shift the equilibrium towards product formation (see, e.g., Yun and Kim, 2008, Biosci. Biotechnol. Biochem. 72(11):3030-3033).

In some embodiments of the processes, the suitable reaction conditions comprise the presence of the reduced cofactor, nicotinamide adenine dinucleotide (NADH), which can act to limit the inactivation of the transaminase enzyme (see e.g., van Ophem et al., 1998. Biochemistry 37(9):2879-88). In such embodiments where NADH is present, a cofactor regeneration system, such as glucose dehydrogenase (GDH) and glucose or formate dehydrogenase and formate can be used to regenerate the NADH in the reaction medium.

In some embodiments, the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product. Removal of the carbonyl by-product can be carried in a number of ways. Where the amino group donor is an amino acid, such as alanine, the carbonyl by product, a keto acid, can be removed by reaction with a peroxide (see, e.g., US 2008/0213845, incorporated herein by reference). Peroxides which can be used include, among others, hydrogen peroxide; peroxyacids (peracids) such as peracetic acid $(CH_3CO_3H)$, trifluoroperacetic acid and metachloroperoxybenzoic acid; organic peroxides such as t-butyl peroxide $((CH_3)_3COOH)$, or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation by employing pyruvate decarboxylase (see, e.g., Höhne et al., 2008, Chem BioChem 9: 363-365) or acetolactate synthase (see, Yun and Kim, supra).

Alternatively, in embodiments where an amino acid is used as amino group donor, the keto acid carbonyl by-product can be recycled back to the amino acid by reaction with ammonia and NADH using an appropriate dehydrogenase enzyme, e.g., amino acid dehydrogenase, in presence of an amine donor, such as ammonia, thereby replenishing the amino group donor.

In some embodiments, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas. In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a transaminase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal and to maintain the pH of the reaction (e.g., at about 8.5).

In further embodiments, any of the above described process for the conversion of substrate compound to product compound can further comprise one or more steps selected from: extraction; isolation; purification; and crystallization of product compound. Methods, techniques, and protocols for extracting, isolating, purifying, and/or crystallizing the product amine from biocatalytic reaction mixtures produced by the above disclosed methods are known to the ordinary artisan and/or accessed through routine experimentation. Additionally, illustrative methods are provided in the Examples below.

Section J: Examples

The following Examples serve to illustrate the invention without limiting the scope thereof, while they on the other hand represent preferred embodiments of the reaction steps, intermediates and/or the process of the present invention.

ABBREVIATIONS

δ chemical shift
μl microliter
μm micrometre
aq aqueous
(+)CSA (+) Camphorsulphonic Acid
ESTP Ethyl Acetate
IPA Isopropyl Acetate
TRMA Treithyl Amine
Ac acetyl
AcOH acetic acid
br broad
brm broad multiplet
br. m. broad multiplet
br. mult. broad multiplet
br. s. broad signal
br. sign. broad signal
cat. catalytic amount
compl. m complex multiplet
compl. mult. complex multiplet
copl. m. complex multiplet
cpl. m. complex multiplet
$CDCl_3$ deuterated chloroform
$CH_2Cl_2$ dichloromethane
$CH_2O$ formaldehyde
$CO_2$ carbon dioxide
d doublet
dd doublet of doublet
de diastereomeric excess
dr diastereomeric ratio
DCM dichloromethane
DEA diethyl amine
DMSO dimethylsulfoxide
DMSO-$d_6$ dimethylsulfoxide deuterated
ee enantiomeric excess
equiv equivalent
ES electrospray
ES+ positive electrospray ionisation
ESI electrospray ionisation
Et ethyl
$Et_2O$ diethyl ether
EtOAc ethyl acetate
EtOH ethanol
FTIR fourier transform infrared
g gram(s)
GC gass chromatography
h hour(s)
HCl hydrochloric acid
$HCl_{aq}$ hydrogen chloride aqueous solution
HNMR proton nuclear magnetic resonance
$^1$HNMR proton nuclear magnetic resonance
HPLC high performance liquid chromatography
$H_3PO_4$ phosphoric acid
HRMS high resolution mass spectroscopy
$H_2SO_4$ sulfuric acid
Hz hertz
iPr isopropyl
$iPr_2NEt$ N-ethyldiisopropylamine
iPrOAc isopropyl acetate
iPrOH isopropanol
IR infrared
J coupling constant
$K_2CO_3$ potassium carbonate
L liter
LC-MS liquid chromatography-mass spectrometry
LCMS liquid chromatography-mass spectrometry
LRMS low resolution mass spectroscopy
m multiplet
m/e mass-to-charge ratio
mg milligram
min minute(s)
ml milliliter
mL milliliter
mmol(s) millimole(s)
mol(s) mole(s)
monosub. monosubstituted
mp melting point
m.p. melting point
mult. d multiplet doublets
m/z mass-to-charge ratio
M molarity/molar
Me methyl
2-MeTHF 2-methyltetrahydrofuran
MeOH methanol
$MgSO_4$ magnesium sulfate
MS mass spectrometry
[MS]+ mass of proton adduct
MTBE tertbutylmethylether
nm nanometre
N nitrogen atom
$N_2$ nitrogen
NaCl sodium chloride
$Na_2CO_3$ sodium carbonate
$NaHCO_3$ sodium bicarbonate
NaHMDS sodium bis(trimethylsilyl)amide
NaOH sodium hydroxide
$Na_2SO_4$ sodium sulfate
$NH_4Cl$ ammonium chloride
NMR nuclear magnetic resonance
oct. octet
ppm parts per million
psi pounds per square inch Pd/C palladium on carbon
Pd(PPh$_3$)$_4$ tetrakis(triphenylphosphine)palladium(0)
Pt/C platinum on carbon
q quartet
Rh/C rhodium on carbon
RT=rt room temperature
s singlet
sev. brm several broad multiplets
sev. dd several doublets of doublets
t triplet
temp. temperature
temperature
$t_R$ retention time
tBu tertiary-butyl
TEA triethylamine
TFA trifluoroacetic acid
THF tetrahydrofuran
Tol toluene
UV ultraviolet light
vol. volume
wt. weight Example 1

Synthesis of Ketone Intermediate

6-Chloro-5-fluoro-3-hydroxy-3-(2-oxo-propyl)-1,3-dihydro-indol-2-one

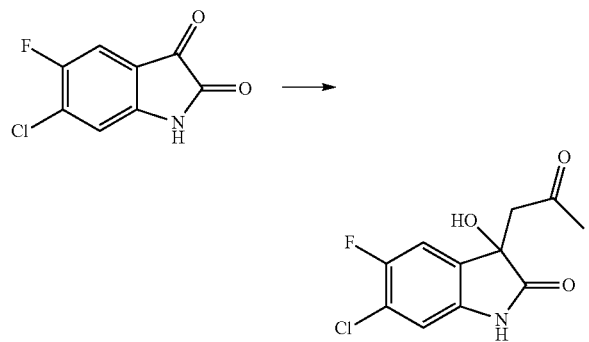

To the suspension of 6-Chloro-5-fluoro-isatin (25 g, 125 mmol) in acetone (620 ml), Et$_2$NH (0.9 g, 12.5 mmol) and K$_2$CO$_3$ (1.7 g, 12.5 mmol) were added. The reaction mixture was heated to reflux for 2 hours. After cooled down to the r.t., the reaction mixture was filtrated and the solvent was removed under reduced pressure. The crude product was re-dissolved in MeOH (300 ml) at 50° C. and water (300 ml) was added. With addition of water, the solid was precipitate. MeOH (250 mL) was removed under reduce pressure at 50° C.; The mixture was cooled down to 0-5° C. and stirred for 30 mins; The solid was filtered and dried to produce 6-Chloro-5-fluoro-3-hydroxy-3-(2-oxo-propyl)-1,3-dihydro-indol-2-one (27 g). $^1$H NMR (DMSO-d$_6$): 2.00 (3H, s, CH$_3$), 3.09 (1H, d, CH, J=16 Hz), 3.39 (1H, d, CH, J=16 Hz), 6.16 (1H, s, OH); 6.88 (1H, d, CH, J=8 Hz), 7.36 (1H, d, CH, J=12 Hz), 10.37 (1H, s, NH). MS (ESI) m/z 258.0 (M+H)$^+$ HPLC method: Column: Agilent Extend-C18; 150×3.0 mm; 3.5 μm. Mobile Phase A (0.1% H3PO4) in water; Mobile Phase B (Acetonitrile). Gradient: 0 min (95% A); 0.5 min (95% A), 14 min (5% A), 19.5 min (5% A). Flow rate: 0.5 ml min-1. Wavelength: 210 nm. Temperature: 40° C. Retention time: 7.52 min.

6-Chloro-5-fluoro-3-hydroxy-3-(2-methyl-[1,3]dioxolan-2-ylmethyl)-1,3-dihydro-indol-2-one

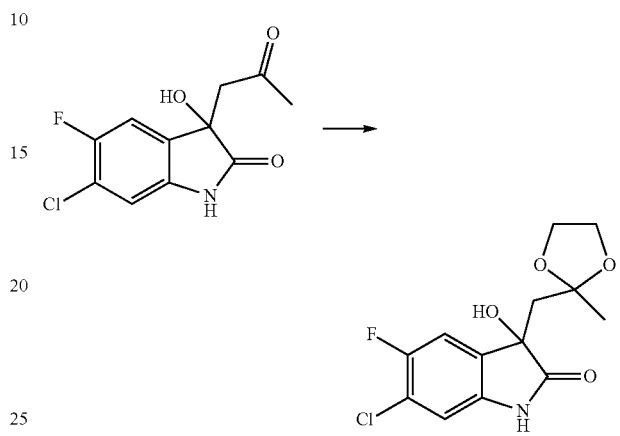

To the suspension of 6-chloro-5-fluoro-3-hydroxy-3-(2-oxopropyl)indolin-2-one (25 g, 97 mmol) in ethylene glycol (250 mL), triethyl orthoformate (43 g, 291 mmol) and toluene-4-sulfonic acid monohydrate (0.9 g, 4.8 mmol) were added. The reaction mixture was heated at 40-50° C. for 2 hours. MeTHF (500 mL) and 10% NaCl aqueous solution (500 mL) were successively added. The organic layer was separated and washed with water twice. After the solvent was evaporated under vacuum, the white solid was washed with TBME (400 mL) and dried to produce 6-Chloro-5-fluoro-3-hydroxy-3-(2-methyl-[1,3]dioxolan-2-ylmethyl)-1,3-dihydro-indol-2-one (27.8 g). $^1$H NMR (DMSO-d$_6$): 1.00 (3H, s, CH$_3$), 2.37 (2H, d, CH$_2$), 3.13 (1H, q, CHH), 3.58 (1H, q, CHH), 3.59 (1H, q, CHH), 3.68 (1H, q, CHH), 6.00 (1H, s, OH); 6.85 (1H, d, CH, J=8 Hz), 7.31 (1H, d, CH, J=12 Hz), 10.24 (1H, s, NH). MS (ESI) m/z 302.0 (M+H)$^+$ HPLC method: Column: Agilent Extend-C18; 150×3.0 mm; 3.5 μm. Mobile Phase A (0.1% H3PO4) in water; Mobile Phase B (Acetonitrile). Gradient: 0 min (95% A); 0.5 min (95% A), 14 min (5% A), 19.5 min (5% A). Flow rate: 0.5 ml min-1. Wavelength: 210 nm. Temperature: 40° C. Retention time: 7.94 min.

1-(6-Chloro-5-fluoro-1H-indol-3-yl)-propan-2-one

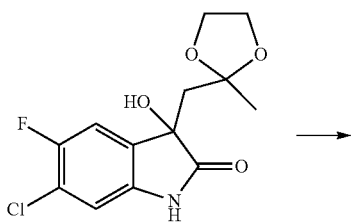

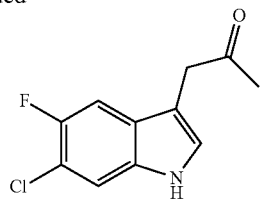

To the solution of 6-chloro-5-fluoro-3-hydroxy-3-((2-methyl-1,3-dioxolan-2-yl)methyl) indolin-2-one (27.8 g, 92 mmol) in THF (250 mL), Red-Al (79.8 g, 276 mmol) in THF (100 mL) was added slowly at 60° C. under $N_2$ atmosphere. After the addition, the mixture was stirring at r.t. for 3 hours. 20% HCl (400 mL) was added and the mixture was stirred for 20 mins. Ethyl acetate (500 mL) was added and stirred for 10 mins. The organic layer was separated and washed with water (100 ml×2); After treated with $Na_2SO_4$ (50 g) and active carbon (5 g) at r.t., the mixture was filtered and the filtration was concentrated. The crude product was recrystallized with MeOH (80 mL) and water (60 mL) to produce 1-(6-Chloro-5-fluoro-1H-indol-3-yl)-propan-2-one (15.5 g).

1H NMR (DMSO-d6): 2.21 (3H, s, CH3), 3.78 (2H, s, CH2), 7.13 (1H, d, CH, J=4 Hz);

MS (ESI) m/z 226.0 (M+H)+

HPLC method: Column: Agilent Extend-C18; 150×3.0 mm; 3.5 μm. Mobile Phase A (0.1% H3PO4) in water; Mobile Phase B (Acetonitrile). Gradient: 0 min (95% A; 0.5 min (95% A), 14 min (5% A), 19.5 min (5% A). Flow rate: 0.5 ml min-1. Wavelength: 210 nm. Temperature: 40 C Retention time: 10.75 min.

Example 2

Second Alternative Synthesis of Ketone Starting Material 1-(6-Chloro-5-fluoro-1H-indol-3-yl)-propan-2-one

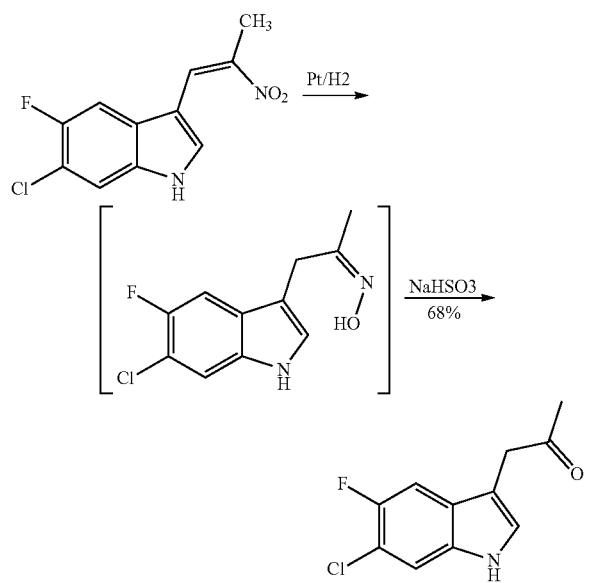

Under $N_2$, Pt/C (10 g, 5% Pt on Carbon) was charged to the suspension of 6-Chloro-5-fluoro-3-((Z)-2-nitro-propenyl)-1H-indole (100 g, 0.39 mol) in ethyl acetate (500 mL). The reaction mixture vacuumed and purged with $H_2$ three times and stirred at r.t. for overnight. The catalyst was filtered off and the organic solvent was removed under reduced pressure to give brown oil. The oil was re-dissolved in EtOH (500 mL) and sodium bisulfite (81.7 g, 0.79 mol) in $H_2O$ ( ) was added. The suspension was heated up to 80° C. for overnight. The precipitate was filtered off and ethanol was removed under pressure. The residue was diluted with water (500 mL) and extracted with ethyl acetate (300 mL×2). The combined organic layer was dried over $Na_2SO_4$ and condensed on the rota vapor to give brown oil (53 g, 60% yield).

Example 3

Second Alternative Synthesis of Ketone Intermediate 1-(6-Chloro-5-fluoro-1H-indol-3-yl)-propan-2-one

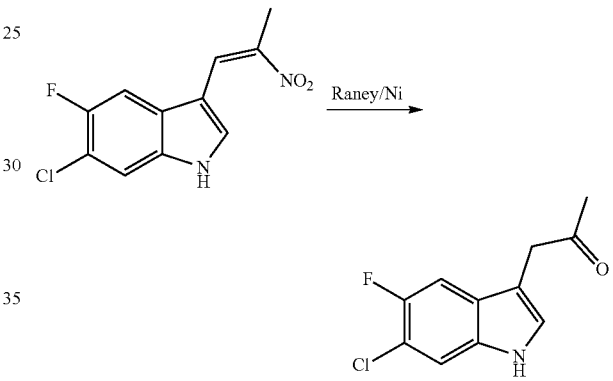

Raney/Ni (0.75 g) and acetic acid (1.1 mL, 19.6 mmol) were charged to the suspension of 6-Chloro-5-fluoro-3-((Z)-2-nitro-propenyl)-1H-indole (5 g, 19.6 mmol) in the mixture of MeOH and $H_2O$ (2:1, 50 mL) at r.t. The reaction mixture vacuumed and purged with $H_2$ three times and heated at 50° C. for overnight. MeOH (50 mL) was added to the reaction mixture and the catalyst was filtered off over celite. The solvent was concentrated to 50 mL and $H_2O$ (300 ml) was added. With the addition of $H_2O$, off-white solid was produced. The solid was filtered and washed by water. After dried in the oven, 2.53 g off-white solid was isolated.

Example 4

Synthesis, Optimization, and Screening Engineered Transaminase Polypeptides

Gene Synthesis and Optimization: The polynucleotide sequence encoding the reported wild-type omega transaminase polypeptide from *Vibrio fluvialis* of SEQ ID NO: 2 was codon optimized and synthesized as the gene of SEQ ID NO: 1. The synthetic gene of SEQ ID NO: 1 was cloned into a pCK110900 vector system (see e.g., US Patent Application Publication 20060195947, which is hereby incorporated by reference herein) and subsequently expressed in *E. coli* W3110fhuA. The *E. coli* W3110 expresses the transaminase polypeptides as an intracellular protein under the control of the lac promoter. The polynucleotide (SEQ ID NO:3) encoding the engineered transaminase polypeptide of SEQ ID NO: 4 was obtained by directed evolution of the codon-optimized gene SEQ ID NO:1. The polypeptide of SEQ ID NO:4 has 24 amino acid residue differences (A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; F427Y) relative to SEQ ID NO:2. This synthetic gene SEQ ID NO: 3 (encoding the polypeptide of SEQ ID NO: 4) was used as the starting backbone for further optimization using standard methods of directed evolution via iterative variant library generation by gene synthesis followed by screening and sequencing of the hits to generate genes encoding engineered transaminases capable of converting compound (IA) to compound (IIA) with improved enzyme properties relative to the polypeptides SEQ ID NOs: 2 and 4. The resulting engineered transaminase polypeptide sequences and specific mutations and relative activities are listed in Table 2A.

Example 5

Production of Engineered Transaminases

The engineered transaminase polypeptides were produced in *E. coli* W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic process disclosed herein.

High-Throughput Growth & Expression. Cells were picked and grown overnight in LB media containing 1% glucose and 30 µg/mL chloramphenicol (CAM), 30° C., 200 rpm, 85% humidity. 20 µL of overnight growth were transferred to a deep well plate containing 380 µL 2×YT growth media containing 30 µg/mL CAM, 1 mM IPTG, 1 mM MgSO$_4$, and incubated for ~18 h at 30° C., 200 rpm, 85% humidity. Subculture TB media was made up of TB media (380 uL/well), 30 ug/mL CAM, 1 mM MgSO4, and 1 mM IPTG. Cell cultures were centrifuged at 4000 rpm, 4° C. for 10 min., and the media discarded. Cell pellets were resuspended in 200 or 400 µL Lysis Buffer (0.1 M triethanolamine (TEA) buffer, pH 9.0, containing 1 mM MgSO$_4$, 400 µg/mL PMBS and 500 µg/mL Lysozyme), as described below.

Production of Shake Flask Powders (SFP): A shake-flask procedure was used to generate engineered transaminase polypeptide powders used in secondary screening assays or in the biocatalytic process disclosed herein. Shake flask powder (SFP) includes approximately 30% total protein and accordingly provide a more purified preparation of an engineered enzyme as compared to the cell lysate used in HTP assays. A single microbial colony of *E. coli* containing a plasmid encoding an engineered transaminase of interest is inoculated into 50 mL Luria Bertani broth containing 30 µg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM MgSO$_4$) containing 30 µg/ml chloramphenicol, in a 1 liter flask to an optical density at 600 nm (OD600) of 0.2 and allowed to grow at 30° C. Expression of the transaminase gene is induced by addition of isopropyl-β-D-thiogalactoside ("IPTG") to a final concentration of 1 mM when the OD600 of the culture is 0.6 to 0.8 and incubation is then continued overnight (at least 16 hours). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0 (optionally including 2 mM MgSO$_4$), and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude transaminase polypeptide. Alternatively, the cell pellet (before or after washing) can be stored at 4° C. or −80° C.

Production of Downstream Process (DSP) Powders: DSP powders contains approximately 80% total protein and accordingly provide a more purified preparation of the engineered transaminase enzyme as compared to the cell lysate used in the high throughput assay. Larger-scale (~100-120 g) fermentation of the engineered transaminase for production of DSP powders can be carried out as a short batch followed by a fed batch process according to standard bioprocess methods. Briefly, transaminase expression is induced by addition of IPTG to a final concentration of 1 mM. Following fermentation, the cells are harvested and resuspended in 100 mM Triethanolamine-H$_2$SO$_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 6

Analytical Procedures

HPLC Analysis of HTP Reactions: An aliquot of the quenched reaction was subject to HPLC analysis under the following conditions.

| | |
|---|---|
| Column | Mightysil RP-18 GP Aqua 150 × 4.6 mm, 5 µm |
| Temperature | 30° C. |
| Mobile Phase | Isocratic, 60% 20 mM NH$_4$Ac (pH 6.6)/40% acetonitrile |
| Flow Rate | 2.5 mL/min |
| Detection | 254 nm |
| Retention Times | Amine Product compound (IIA): 0.96 min; Substrate Impurity: 1.8 min; Ketone Substrate compound (IA): 2.7 min |

Conversion of compound (IA) to compound (IIA) was determined from the resulting chromatograms as follows:

Conversion(%)=Product Area/(Product Area+Substrate Area×0.73)×100%

HPLC Analysis of 5 mL and 100 mL Scale Reactions: Aliquots of the quenched reaction was subject to HPLC analysis under the following conditions.

| | |
|---|---|
| Column | Mightysil RP-18 GP Aqua 250 × 4.6 mm, 5 um |
| Temperature | 30° C. |
| Mobile Phase | Isocratic: 60% 20 mM NH$_4$Ac (pH 6.6)/40% acetonitrile |
| Flow Rate | 2.0 mL/min |
| Detection | 254 nm |

-continued

| Retention Times | Amine Product compound (IIA): 2.1 min<br>Ketone Substrate compound (IA): 7.6 min |

Conversion of compound (IA) to compound WA) was determined from the chromatograms as follows:

Conversion(%)=Product Area/(Product Area+Substrate Area×0.73)×100%

Determination of Product Chiral Purity (% Ee): The chiral purity or enantiomeric excess of compound (IIA) was assessed by HPLC using the following conditions.

| Column | Astec Chirobiotic TAG column |
|---|---|
| Temperature | 15° C. |
| Mobile Phase | Methanol/Acetic acid/Triethylamine (100/0.2/0.1) |
| Flow Rate | 1.0 mL/min |
| Detection Wavelength | 225 nm |
| Retention Times | Ketone substrate: 3.6 min<br>R-product: 17.9 min;<br>S-product: 18.9 min |

Determination of Product Purity: The purity of product was determined by HPLC using the following conditions.

| Column | Mightysil Rp-18 GP aqua 250 × 4.6 mm, 5 µm | |
|---|---|---|
| Temperature | 30° C. | |
| Mobile Phase | Gradient, A: 20 mM NH$_4$Ac (pH 6.6); B: acetonitrile | |
| | Time | Composition |
| | 0 min | 5% B |
| | 1.5 min | 5% B |
| | 35 min | 70% B |
| | 40 min | 70% B |
| | 45 min | 5% B |
| | 60 min | 5% B |
| Flow Rate | 1.5 mL/min | |
| Detection Wavelength | 254 nm | |
| Retention Times | Major impurity: 22.2 min; amine product: 17.5 min; ketone substrate: 25.4 min | |

Example 7

High Throughput (HTP) Screening of Transaminases for Conversion of Compound (IA) to Compound (IIA)

HTP Screening Assays: High-throughput screening used to guide primary selection of variants was carried out in 96-well plates using cell lysates under assay conditions of 10 g/L compound (IA); 1 mM pyridoxal phosphate (PLP); 2 M isopropylamine (IPM), pH 7.0); 0.1 M triethanolamine (TEA), pH 7; 5% v/v PEG200; 10 uL lysate; and 50 or 55° C.

Cells were grown in 96-well plates as described above and lysates prepared by dispensing 200 uL (for Round 1) or 400 uL (for Round 2) of Lysis Buffer (1 mg/mL lysozyme, 0.5 mg/mL polymyxin B sulfate, 1 mM PLP, 0.1 M triethanolamine (TEA), pH 7.0) into each well. Plates were sealed, shaken for 2 h, and then centrifuged for 20 min at 4,000 rpm at 4° C. to pellet the cell debris.

A 10 uL of stock substrate solution (200 g/L compound (IIA) dissolved in PEG200) was added to each well of a 96-well plate followed by 180 uL of a stock solution of isopropylamine (IPM)/pyridoxal phosphate (PLP) (2.2 M IPM and 1.06 mM PLP in 100 mM TEA, pH 7.0. For assessing refractoriness to product compound (IIA) inhibition, compound WA) was added to the reaction mixture to a final 14 g/L for Round 1 and 16 g/L Round 2 assays. Reactions were initiated by adding 10 uL of cell lysate/well. Plates were sealed and incubated with shaking at 50 or 55° C. for 24 h. Reactions were quenched with 600 uL of acetonitrile and samples examined by HPLC as described in Example 5.

Example 8

Process for Conversion of Compound (IA) to Compound (IIA) in 5 mL Scale

A 5 ml scale reactions were carried out as follows. To a 20 mL glass vial with equipped a cross-shaped magnetic stirring bar was added 0.75 mL (or 0.5 mL in case of 10% v/v PEG 200 concentration) of 100 mM TEA buffer (pH 7.0). 2 mL of 5 M IPM.HCl stock solution was added to the vial followed by 1 mL of 5 mM PLP stock solution. The mixture was stirred at 500 rpm (magnetic stirring). The pH of the mixture was then adjusted to 7.0 using 1 M NaOH solution. 125 mg (or 250 mg for 50 g/L or 500 mg for 100 g/L concentration) substrate (solid) was then added to the vial. 0.25 mL (or 0.5 mL for 10% v/v) PEG 200 was then added to the mixture. Final concentrations of components were: 25 g/L (or 50 or 100 g/L) of compound (IA); 1 mM PLP; 2 M IPM; 5% v/v (or 10%) PEG 200; 2 g/L TA enzyme; 100 mM TEA, pH 7.0). The mixture was then stirred and heated to 50° C.

Reactions were initiated by adding 1 mL of the enzyme stock solution (10 g/L). 20 uL samples were taken at different time points and diluted with 750 uL methanol and analyzed by HPLC. After 24 h, the reaction mixtures were quenched with 5 mL acetonitrile and samples analyzed by HPLC to get the final % conversion.

Example 9

Process for Conversion of Compound (IA) to Compound (IIA) in 100 mL Scale

A 100 mL scale reaction was carried out as follows. To a 250 mL round bottom flask with an anchor-shaped stirring blade was added 15 mL of 100 mM TEA buffer (pH 7). 40 mL of the 5 M IPM.HCl stock solution was added to the round bottom flask followed by 20 mL of the 5 mM PLP stock solution. The mixture was stirred at 100 rpm (overhead stirring) and the pH adjusted to 7.0 using 10 M NaOH. Solid substrate Compound (IA) was then added to the round bottom flask over ~5 min with stirring. PEG 200 (5 mL) was then added and the mixture heated to 50° C. 20 mL of the enzyme stock solution (10 g/L) was then added to start the reaction. The reaction was stirred at 200 rpm (overhead stirring). 20 uL samples were taken at different time points and diluted with 750 uL methanol and analyzed by HPLC. In some cases, where work up was not pursued, after 24 h, the reaction mixtures were quenched with 100 mL acetonitrile and samples analyzed by HPLC to get the final % conversion (FIG. 9). Concentration of different components in the reaction: ketone: 25 g/L (or 50 or 100 g/L); PLP: 1 mM; IPM: 2 M; PEG200: 5% v/v; TA enzyme:2 g/L; buffer: 100 mM TEA, pH 7.0. Conversion of substrate to product was analyzed by HPLC as described in Example 3.

Product Workup: After 24 h reaction under the conditions described above (up to point 11) the reaction mixture was cooled to room temperature. The mixture was filtered through a standard G4 sintered glass funnel with a piece of filter paper (Whatman 1, pore size 11 μm). The round bottom flask was rinsed with 20 mL deionized water which was then filtered through the same funnel. The filter cake was washed twice with 20 mL deionized water. The pH of the filtrate was adjusted from 6.8 to 3 using a 5 M HCl solution. The filtrate was then transferred into a separatory funnel and extracted with 100 mL MTBE. The biphasic mixture was allowed to separate. The MTBE layer containing unreacted substrate and impurities was discarded. The aqueous layer was transferred into a beaker and 100 mL MTBE was added. The pH of the aqueous layer was then adjusted from 3 to 10 using 10 M NaOH solution. The mixture was transferred into a separatory funnel and the phases allowed to separate.

The aqueous layer was then extracted with 100 mL MTBE three times (nb: repeated until product was not present in aqueous layer). The MTBE phases from the three extractions were combined and evaporated to dryness using a rotary evaporator. The crude product was further dried under vacuum for 48 h.

Example 10

Process for Conversion of Compound (IA) to Compound (IIA) in 30 g Scale

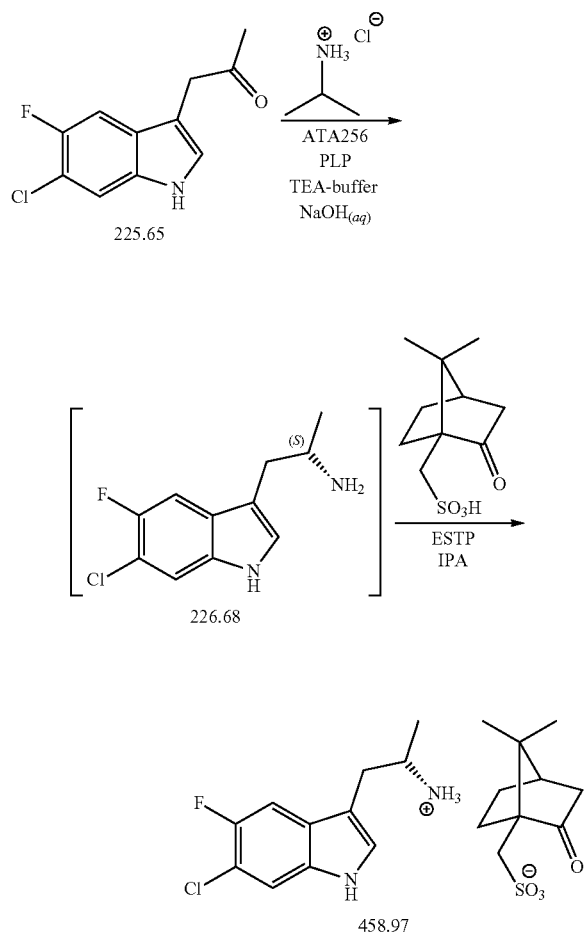

152.48 g iso-propylamine hydrochloride and 0.204 g pyridoxalphosphate monohydrate were dissolved in 495 ml water while stirring. To this yellow clear solution a solution of 30.0 g ketone in 85 ml poly ethylene glycol (average mol weight 200) within 15 minutes. Upon addition the ketone precipitates as fine particles which are evenly distributed in the reaction media. To the suspension 180 ml triethanolamine buffer (0.1 mol/l, pH 7) were added and the pH was adjusted to 7 by addition of aqueous sodium hydroxide solution (1 mol/l). The reaction mixture is heated to 50° C. and a solution of 1.62 g transaminase SEQ ID NO: 134 dissolved in 162 ml triethanolamine buffer (0.1 mol/l, pH 7) is added. The reaction mixture is continuously kept at pH 7 by addition of 1 mol/l aqueous sodium hydroxide solution. The reaction mixture is stirred 24 h at 50° C. and a stream of Nitrogen is blown over the surface of the reaction mixture to strip off formed acetone. The reaction mixture is then cooled to 25° C. and filtered over a bed of cellulose flock. The pH of the filtrate is adjusted to ≈1 by addition of concentrated sulfuric acid. The acidified filtrated is extracted with 250 ml iso-Propyl acetate. The layers are separated and the pH of the aqueous phase is adjusted to ≈10 by addition of concentrated aqueous sodium hydroxide solution. The basified aqueous phase is extracted with iso-propyl acetate. The layers are separated and the organic phase is washed with 100 ml water. The organic phase is concentrated by distillation to ⅔ of its origin volume. In a second reactor 33.98 g (+)-camphor sulfonic acid is dissolved in 225 ml iso-propyl acetate upon refluxing and the concentrated organic phase is added within 10 minutes. After complete addition the formed thin suspension is cooled to 0° C. within 2 hours and kept at 0° C. for 15 hours. The precipitated amine-(+)-camphor sulfonate salt is filtered, washed with 70 ml iso-propyl acetate and dried at 40° C. in vacuum yielding 51.57 g of colourless crystals (84.5% yield t.q.)

Analytical Data

IR:

$\tilde{\nu}(cm^{-1})$=3296, 3061, 2962, 2635, 2531, 2078, 1741, 1625, 1577, 1518, 1461, 1415, 1392, 1375, 1324, 1302, 1280, 1256, 1226, 1170, 1126, 1096, 1041, 988, 966, 937, 868, 834, 814, 790, 766, 746, 719, 669, 615.

LC-MS (ESI+):

Ammonium ion: m/z=227 ([M+H]), 268 ([M+H+CH$_3$CN]), 453 ([2M+H]).

Camphorsulfonate ion: m/z=250 ([M+NH$_4$]), 482 ([2M+NH4]).

LC-MS (ESI−):

Camphorsulfonate ion: m/z=231 ([M−H]), 463 ([2M−H]).

$^1$H-NMR (DMSO-d6, 400 MHz):

11.22 (br. s., 1H), 7.75 (br. s., 3H), 7.59 (d, J=10.3 Hz, 1H), 7.54 (d, J=6.5 Hz, 1H), 7.36 (d, J=2.3 Hz, 1H), 3.37-3.50 (m, 1H), 2.98 (dd, J=14.3, 5.8 Hz, 1H), 2.91 (d, J=14.8 Hz, 1H), 2.81 (dd, J=14.3, 8.0 Hz, 1H), 2.63-2.74 (m, 1H), 2.41 (d, J=14.6 Hz, 1H), 2.24 (dt, J=18.3, 3.8 Hz, 1H), 1.94 (t, J=4.4 Hz, 1H), 1.86 (dt, J=7.4, 3.6 Hz, 1H), 1.80 (d, J=18.1 Hz, 1H), 1.23-1.35 (m, 2H), 1.15 (d, J=6.3 Hz, 3H), 1.05 (s, 3H), 0.74 (s, 3H)

Free Amine (obtained by evaporating the iso-Propylacetate layer after extraction of the basified aqueous layer):

$^1$H NMR (400 MHz, DMSO-d$_6$): 11.04 (br. s., 1H), 7.50 (d, J=10.5 Hz, 1H), 7.48 (d, J=6.5 Hz, 1H), 7.25 (s, 1H), 3.03 (sxt, J=6.3 Hz, 1H), 2.61 (dd, J=14.3, 6.5 Hz, 1H), 2.57 (dd, J=14.1, 6.5 Hz, 1H), 1.36 (br. s., 2H), 0.96 (d, J=6.3 Hz, 3H)

Example 11

Process for Conversion of Compound (IIA) to Compound (IVB)

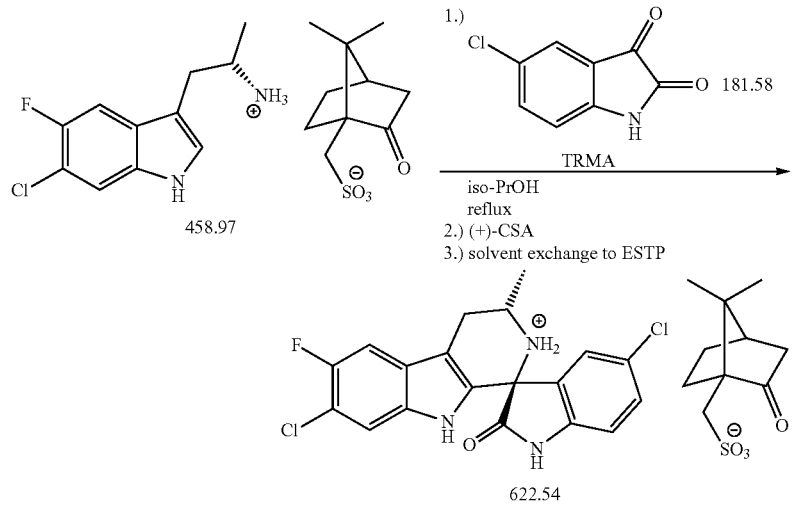

13.62 g 5-chloroisatin is suspended in 35 ml iso-propanol and 2.3 g triethyl amine is added. The suspension is heated to reflux and a solution of 34.42 g amine-(+)-camphor sulfonate salt dissolved in 300 ml iso-propanol is added within 50 minutes. The reaction mixture is stirred at reflux for 17 hours. The reaction mixture is cooled to 75° C. and 17.4 g (+)-camphorsulfonic acid are added to the reaction mixture. Approximately 300 ml iso-propanol are removed by vacuum distillation. Distilled off iso-propanol is replaced by iso-propyl acetate and vacuum distillation is continued. This is distillation is repeated a second time. To the distillation residue 19 ml ethanol and 265 ml ethyl acetate is added and the mixture is heated to reflux. The mixture is cooled in ramps to 0° C. and kept at 0° C. for 24 hours. The beige to off white crystals are filtered off, washed with 3 portions (each 25 ml) precooled (0° C.) ethylacetate and dried in vacuum yielding 40.3 g beige to off white crystals. (86.3% yield t.q.)

IR:
$\tilde{\nu}(cm^{-1})$=3229, 3115, 3078, 3052, 2971, 2890, 2841, 2772, 2722, 2675, 2605, 2434, 1741, 1718, 1621, 1606, 1483, 1460, 1408, 1391, 1372, 1336, 1307, 1277, 1267, 1238, 1202, 1184, 1162, 1149, 1128, 1067, 1036, 987, 973, 939, 919, 896, 871, 857, 843, 785, 771, 756, 717, 690, 678, 613.

LC-MS (ESI+):
Ammonium ion: m/z=390 ([M+H]), 431 ([M+H+CH$_3$CN])
Camphorsulfonate ion: m/z=250 ([M+NH$_4$]), 482 ([2M+NH4])

LC-MS (ESI−):
Camphorsulfonate ion: m/z=231 ([M−H]), 463 ([2M−H])

$^1$H NMR (DMSO-d$_6$, 600 MHz):
11.49 (s, 1H), 11.23 (s, 1H), 10.29-10.83 (m, 1H), 9.78-10.31 (m, 1H), 7.55-7.60 (m, 2H), 7.52 (s, 1H), 7.40 (d, J=6.2 Hz, 1H), 7.16 (d, J=8.8 Hz, 1H), 4.52-4.63 (m, 1H), 3.20 (dd, J=16.3, 4.2 Hz, 1H), 2.96 (dd, J=16.1, 11.3 Hz, 1H), 2.90 (d, J=15.0 Hz, 1H), 2.56-2.63 (m, 1H), 2.39 (d, J=14.6 Hz, 1H), 2.21 (dt, J=18.0, 3.8 Hz, 1H), 1.89-1.93 (m, 1H), 1.81 (ddd, J=15.3, 7.8, 3.7 Hz, 1H), 1.76 (d, J=18.3 Hz, 1H), 1.53 (d, J=6.6 Hz, 3H), 1.20-1.33 (m, 2H), 0.98 (s, 3H), 0.70 (s, 3H)

Example 12

Process for Preparing a Compound of Formula (IVA) ½ Hydrate

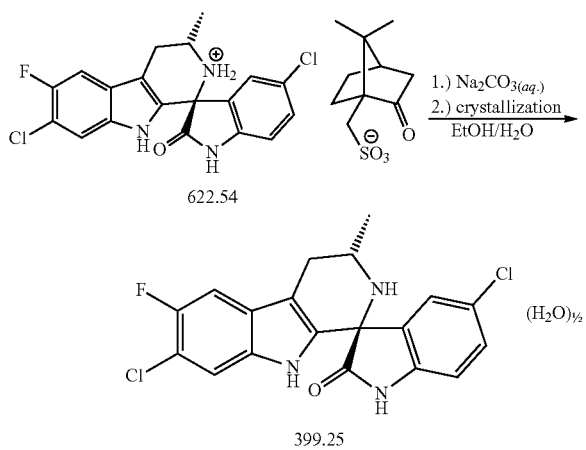

In a 750 ml reactor with impeller stirrer 50 g of compound (IVB) salt were dissolved in 300 ml Ethanol (ALABD) and 100 ml deionised Water (WEM). The clear, yellowish solution was heated to 58° C. internal temperature. To the solution 85 g of a 10% aqueous sodium carbonate solution was added within 10 minutes. The clear solution was particle filtered into a second reaction vessel. Vessel and particle filter were each rinsed with 25 ml of a mixture of ethanol:water (3:1 v/v) in the second reaction vessel. The combined particle filtered solution is heated to 58° C. internal temperature and 200 ml water (WEM) were added dropwise within 15 minutes. Towards the end of the addition the solution gets turbid. The mixture is stirred for 10 minutes at 58° C. internal temperature and is then cooled slowly to room temperature within 4 hours 30 minutes forming a thick, well stirable white suspension. To the suspension 200 ml water are added and the mixture is stirred for additional 15 hours 20 minutes at room temperature. The suspension is filtered and the filter cake is washed twice with 25 ml portions of a mixture of ethanol:water 9:1 (v/v). The colourless crystals are dried at 60° C. in vacuum yielding 26.23 g (=91.2% yield).

$^1$H NMR (400 MHz, DMSO-$d_6$)

10.70 (s, 1H), 10.52 (s, 1H), 7.44 (d, J=10.0 Hz, 1H), 7.33 (dd, J=8.4, 2.1 Hz, 1H), 7.26 (d, J=6.5 Hz, 1H), 7.05 (d, J=2.3 Hz, 1H), 6.93 (d, J=8.3 Hz, 1H), 3.83-4.00 (m, 1H), 3.13 (d, J=6.0 Hz, 1H), 2.77 (dd, J=15.1, 3.8 Hz, 1H), 2.38 (dd, J=15.1, 10.5 Hz, 1H), 1.17 (d, J=6.3 Hz, 3H).

The invention claimed is:

1. A process for preparing a compound of formula (II), or a salt, solvate, or hydrate thereof,

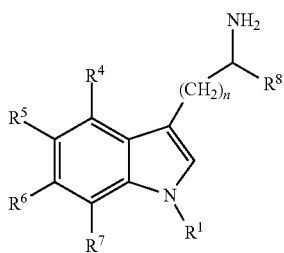
(II)

Comprising enzymatically converting a compound of formula (I) to compound of formula (II), or a salt, solvate or hydrate thereof,

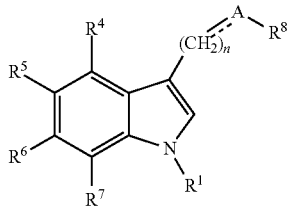
(I)

wherein:
the enzyme is SEQ ID NO: 134
the dashed line is a bond or absent;
A is selected from C=O or C=NH; or when the dashed line is a double bond A-R$^8$ is:

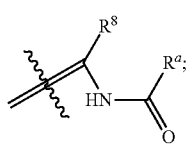

$R^a$ is $C_{1-6}$ alkyl;
$R^1$ is H, —CH$_3$,

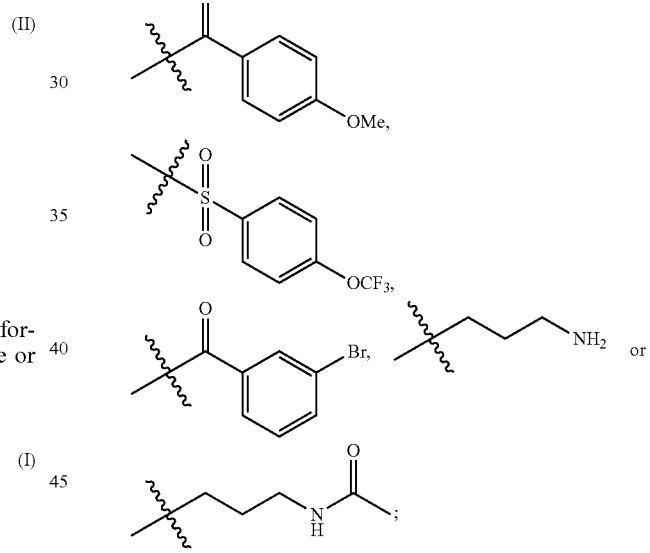

$R^4$ and $R^7$ are each, independently, H or —Cl;
$R^5$ is H, —OH, —CH$_3$, —OCH$_3$, —F, —Cl, —CF$_3$ or —CN;
$R^6$ is H, —OH, —OCH$_3$, —F or —Cl;
$R^8$ is H, —CH$_3$, —CH$_2$CH$_3$, —CH$_2$OH, —CO$_2$H, —CO$_2$CH$_2$CH$_3$ or —CF$_3$; and
n is 1 or 2.

2. The process of claim 1, wherein $R^5$ and $R^6$ are fluoro when: $R^8$ is —CH$_3$, and n is 1.

3. The process of claim 1, wherein $R^5$ and $R^6$ are each, independently, fluoro or chloro, when: $R^8$ is —CH$_3$, and n is 1.

4. The claim 1, wherein $R^5$ and $R^6$ are hydrogen when: $R^8$ is —CH$_3$ and n is 1.

5. The process of claim 1, wherein $R^5$ is fluoro when; n is 1, and $R^6$ is hydrogen.

6. The process of claim 1, wherein the compound of formula (II) is of formula (IIA), or a salt or solvate or hydrate thereof,

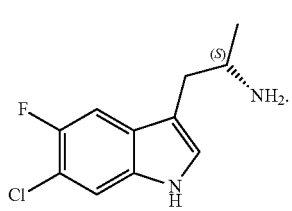
(IIA)
7. The process according to claim 1 or 6, wherein the compound of formula (I) is a compound of formula (IA) or a salt or hydrate, or solvate thereof,
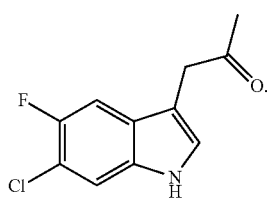
(IA)
* * * * *

SEQUENCE LISTING

```
<160> NUMBER OF SEQ ID NOS: 154

<210> SEQ ID NO 1
<211> LENGTH: 1362
<212> TYPE: DNA
<213> ORGANISM: Artificial Sequence
<220> FEATURE:
<223> OTHER INFORMATION: Codon optimized transaminase gene from Vibrio
      fluvialis

<400> SEQUENCE: 1
atgaacaaac cgcagagctg ggaagcgcgt gcggaaacct atagcctgta tggctttacc       60
gatatgccga gcctgcatca gcgtggcacc gtggtggtga cccatggcga aggcccgtat      120
atcgtggatg tgaacggccg tcgttatctg gatgcgaaca cgcgcctgtg aacatggtg       180 gcgggctttg atcataaagg cctgattgat gcggcgaaag cgcagtatga acgttttccg      240
ggctatcatg cgtttttgg ccgtatgagc gatcagaccc tgatgctgtc tgaaaaactg       300
gtggaagtga gcccgtttga tagcggccgt gtgttttata ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggcgtga ccgcggtgag cgcgagcatg      480
accggcaaac gtataacag cgtgtttggc ctgccgctgc cgggctttgt gcatctgacc       540
tgcccgcatt attggcgtta tggcgaagaa ggcgaaaccg aagaacagtt tgtggcgcgt      600
ctggcccgtg aactggaaga aaccattcag cgtgaaggcg cggataccat tgcgggcttt      660
tttgcggaac cggtgatggg tgcgggcggt gttattccgc cggcgaaagg ctatttttcag     720 gcgattctgc cgatcctgcg caaatatgat attccggtga tcagcgatga agtgatttgc      780
ggctttggcc gtaccggcaa cacctgggc tgcgtgacct atgatttac cccggatgcg        840 attattagca gcaaaaacct gaccgcgggt ttttttccga tgggcgcggt gattctgggt      900
ccggaactga gcaaacgtct ggaaaccgcg attgaagcga tcgaagaatt tccgcatggt      960
tttaccgcga gcggccatcc ggtgggttgt gcgattgcgc tgaaagcgat tgatgtggtg     1020
atgaacgaag gcctggccga aaacgtgcgt cgtctggccc gcgttttga agaacgtctg      1080 aaacatattg cggaacgtcc gaacattggc gaatatcgtg gcattggctt tatgtgggcg     1140
ctggaagcgg tgaaagataa agcgagcaaa accccgtttg atggcaacct gagcgtgagc     1200
gaacgtattg cgaacacctg caccgatctg ggcctgattt gcgtccgct gggccagagc      1260 gtggttctgt gcccgccgtt tattctgacc gaagcgcaga tggatgaaat gttcgataaa     1320
ctggaaaaag cgctggataa agtgtttgcg gaagtggcgt aa                       1362

<210> SEQ ID NO 2
<211> LENGTH: 453
<212> TYPE: PRT
<213> ORGANISM: Vibrio fluvialis

<400> SEQUENCE: 2
```

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
```

```
                420            425              430
Gln Met Asp Glu Met Phe Asp Lys Leu Glu Lys Ala Leu Asp Lys Val
            435                440                445

Phe Ala Glu Val Ala
    450

<210> SEQ ID NO 3
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 3
atgaacaaac cgcagagctg ggaaacgcgt gcggaaacct atagcctgta tgcctttacc        60
cacatgccga gcctacatca gcgtggcacc atggtggtga cccatggcga aggcccgtat       120
atcgtggatg tgcatggccg tcgttatctg gatgcgaaca gcggcctgtg aacatggtg        180 gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatcgtg cggaaggcaa accgcagaaa       420
cgtaaaattc tgaccctgaa aacgcgtat catggctcca ccgcggtgag cgcgagcatg       480 accggcttc cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactggaaga accattcag aaggaaggcg cggataccat tgcgggcttt        660
tttgcggaac cggtgatggg tgcgggcggt gttattaccc cgccaaaagg ctattttcag       720
gcgattctga ccatcctgcg caaatatgat attccggtga tcagcgatga agtgatttgc       780
ggctttggtc gtaccggcaa cacctggggc tgcgtgacct atgattttac cccggatgcg       840
attattagca gtaaaaacct aaccgcgggt tttttccag taggagcggt gattttgggg        900
ccggaactga gcaaacgtct ggaaaccgcg attgaagcga tcgaagaatt tgatcatggt       960
tttaccacag gcggccatcc ggtgggttgt gcgattgcgc tgaaagcgat tgatgtggtg      1020
atgaacgaag gcctggccga aaacgtgcgt cgtctggccc gcgttttga agaacgtctg       1080 aaacatattg cggaacgtcc gaacattggc gaatatcgtg gtattggctt tatgtgggcg      1140
ctggaagtgg tgaaagataa agcgagcaaa gccccgtttg atggcaacct gagcgtgagc      1200
gaacgtattg cgaacacctg caccgatctg ggactgattt gccgaccgtt gggccagagc      1260
gtggttctgg caccgccgta cattctgacc gaagcgcaga tggatgaaat gttcgataaa      1320
ctggaaaaag cgctggataa agtgtttgcg gaagtggcgt aa                         1362

<210> SEQ ID NO 4
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 4

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

```
Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
     50                  55                  60

His Lys Gly Leu Ile Asp Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
                115                 120                 125

Trp Phe Leu His Arg Ala Glu Gly Lys Pro Gln Lys Arg Lys Ile Leu
            130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445
```

Phe Ala Glu Val Ala
    450

<210> SEQ ID NO 5
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 5

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 6
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 6

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
```

```
                    50                  55                  60
His Lys Gly Leu Ile Asp Ala Lys Ala Gln Tyr Glu Arg Phe Pro
 65                  70                  75                  80

Gly Tyr His Ala Phe Tyr Gly Arg Met Ser Asp Gln Thr Val Met Leu
                     85                  90                  95

Ser Glu Lys Leu Val Glu Val Ser Pro Phe Asp Ser Gly Arg Val Phe
                    100                 105                 110

Tyr Thr Asn Ser Gly Ser Glu Ala Asn Asp Thr Met Val Lys Met Leu
                    115                 120                 125

Trp Phe Leu His Arg Ala Glu Gly Lys Pro Gln Lys Arg Lys Ile Leu
                    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                    165                 170                 175

Leu His Leu Thr Cys Pro His Tyr Trp Arg Tyr Gly Glu Glu Gly Glu
                    180                 185                 190

Thr Glu Glu Gln Phe Val Ala Arg Leu Ala Arg Glu Leu Glu Glu Thr
                    195                 200                 205

Ile Gln Lys Glu Gly Ala Asp Thr Ile Ala Gly Phe Phe Ala Glu Pro
                    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                    245                 250                 255

Glu Val Ile Cys Gly Phe Gly Arg Thr Gly Asn Thr Trp Gly Cys Val
                    260                 265                 270

Thr Tyr Asp Phe Thr Pro Asp Ala Ile Ile Ser Ser Lys Asn Leu Thr
                    275                 280                 285

Ala Gly Phe Phe Pro Val Gly Ala Val Ile Leu Gly Pro Glu Leu Ser
                    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                    325                 330                 335

Ile Asp Val Val Met Asn Glu Gly Leu Ala Glu Asn Val Arg Arg Leu
                    340                 345                 350

Ala Pro Arg Phe Glu Glu Arg Leu Lys His Ile Ala Glu Arg Pro Asn
                    355                 360                 365

Ile Gly Glu Tyr Arg Gly Ile Gly Phe Met Trp Ala Leu Glu Val Val
                    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                    405                 410                 415

Leu Gly Gln Ser Val Val Leu Ala Pro Pro Tyr Ile Leu Thr Glu Ala
                    420                 425                 430

Gln Met Asp Glu Met Phe Asp Lys Leu Glu Lys Ala Leu Asp Lys Val
                    435                 440                 445

Phe Ala Glu Val Ala
                    450
```

<210> SEQ ID NO 7

<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 7

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggcattc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgatttac cccggatgcg     840
attattagca gtaaaaacct aaccgcgggt tttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga gaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgac Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
            130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
450

<210> SEQ ID NO 9
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 9

```
atgaacaaac cgcagagctg ggaaacgcgt gcggaaacct atagcctgta tgcctttacc    60
cacatgccga gcctacatca gcgtggcacc atggtggtga cccatggcga aggcccgtat   120
atcgtggatg tgcatggccg tcgttatctg gatgcgaaca gcggcctgtg gaacatggtg   180
gcgggctttg atcataaagg cctgattgat gcggcgaaag cgcagtatga acgttttccg   240
ggctatcatg cgttttacgg ccgtatgagc gatcagaccg tgatgctgtc tgaaaaactg   300
gtggaagtga gcccgtttga tagcggccgt gtgttttata ccaacagcgg cagcgaagcg   360
aacgatacca tggtgaaaat gctgtggttt ctgcatcgtg cggaaggcaa accgcagaaa   420
cgtaaaattc tgaccctgaa gaacgcgtat catggctcca ccgcggtgag cgcgagcatg   480
accggccgtc gtataacag cgtgtttggc ctgccgctgc cgggcttttct gcatctgacc   540
tgcccgcatt attggcgtta tggcgaagaa ggcgaaaccg aagaacagtt tgtcgcgcgt   600
ctggcccgtg aactggaaga accattcag aaggaaggcg cggataccat tgcgggcttt   660
tttgcggaac cggtgatggg tgcgggcggt gttattaccc cgccaaaagg ctattttcag   720
gcgattctga ccatcctgcg caaatatgat attccggtga tcagcgatga agtgatttgc   780
ggctttggtc gtaccggcaa cacctggggc tgcgtgacct atgattttac cccggatgcg   840
attattagca gtaaaaacct aaccgcgggt tttttttccag taggagcggt gattttgggg   900
ccggaactga gcaaacgtct ggaaaccgcg attgaagcga tcgaagaatt tgatcatggt   960
tttaccacag cggccatcc ggtgggttgt gcgattgcgc tgaaagcgat tgatgtggtg  1020
atgaacgaag gcctggccga aacgtgcgt cgtctggccc cgcgttttga agaacgtctg  1080
aaacatattg cggaacgtcc gaacattggc gaatatcgtg gtattggctt tatgtgggcg  1140
ctggaagtgg tgaaagataa agcgagcaaa gccccgtttg atggcaacct gagcgtgagc  1200
gaacgtattg cgaacacctg caccgatctg ggactgattt gcc Tyr Thr Asn Ser Gly Ser Glu Ala Asn Asp Thr Met Val Lys Met Leu
         115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Arg Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
                210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
                290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Val Val
                370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 11
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 11
atgaacaaac cgcagagct

```
cacatgccga gcctacatca gcgtggcacc atggtggtga cccatggcga aggcccgtat    120
atcgtggatg tgcatggccg tcgttatctg gatgcgaaca gcggcctgtg aacatggtg     180
gcgggctttg atcataaagg cctgattgat gcggcgaaag cgcagtatga acgttttccg    240
ggctatcatg cgtttgatgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa aacgcgtat catggctcca ccgcggtgag cgcgagcatg     480
accggctttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctatttttcag   720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt tttttttccag taggagcggt gattttgggg   900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg    1020
atgaacgaag gcctggccga aaacgtgcgt cgtctggccc gcgttttga agaacgtctg     1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacaccctg caccgatctg ggactgattt gccgaccgtt gggccagagc   1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 12
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 12

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
```

```
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 13
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 13
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
```

```
ggctatcatg cgttttacgg ccgtatgagc gatcagaccg tgatgctgtc tgaaaaactg      300
gtggaagtga gcccgtttga tagcggccgt gtgttttata ccaacagcgg cagcgaagcg      360
aacgatacca tggtgaaaat gctgtggttt ctgcatcgtg cggaaggcaa accgcagaaa      420
cgtaaaattc tgaccctgaa aaacgcgtat catggctcca ccgcggtgag cgcgagcatg      480
accggcgtgc gtataacag cgtgtttggc ctgccgctgc cgggcttttct gcatctgacc      540 tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcggcggt gttattaccc cgccaaaagg ctatttttcag     720 gcgattctga ccatcctgcg caaatatgat attccggtga tcagcgatga agtgatttgc      780
ggctttggtc gtaccggcaa cacctggggc tgcgtgacct atgattttac cccggatgcg      840
attattagca gtaaaaacct aaccgcgggt ttttttccag taggagcggt gattttgggg      900
ccggaactga gcaaacgtct ggaaaccgcg attgaagcga tcgaagaatt tgatcatggt      960
tttaccacag gcggccatcc ggtgggttgt gcgattgcgc tgaaagcgat tgatgtggtg     1020
atgaacgaag gcctggccga aaacgtgcgt cgtctggccc gcgttttga agaacgtctg     1080 aaacatattg cggaacgtcc gaacattggc gaatatcgtg gtattggctt tatgtgggcg     1140
ctggaagtgg tgaaagataa agcgagcaaa gccccgtttg atggcaacct gagcgtgagc     1200
gaacgtattg cgaacacctg caccgatctg ggactgattt gccgaccgtt gggccagagc     1260
gtggttctgg caccgccgta cattctgacc gaagcgcaga tggatgaaat gttcgataaa     1320
ctggaaaaag cgctggataa agtgtttgcg gaagtggcgt aa                         1362
```

<210> SEQ ID NO 14
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 14

```
Met Asn Lys Pro Gln Ser Trp Glu Thr Arg Ala Glu Thr Tyr Ser Leu

-continued

```
Thr Gly Val Pro Tyr Asn Ser Val Phe Gly Leu Pro Leu Pro Gly Phe
            165                 170                 175
Leu His Leu Thr Cys Pro His Tyr Trp Arg Tyr Gly Glu Glu Gly Glu
        180                 185                 190
Thr Glu Glu Gln Phe Val Ala Arg Leu Ala Arg Glu Leu Glu Glu Thr
    195                 200                 205
Ile Gln Lys Glu Gly Ala Asp Thr Ile Ala Gly Phe Phe Ala Glu Pro
210                 215                 220
Val Met Gly Ala Gly Val Ile Thr Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Gly Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450
```

<210> SEQ ID NO 15
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 15

```
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgtttctga ccaacagcgg cagcgaagcg     360
```

-continued

```
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 16
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 16

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
                100                 105                 110

Leu Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
        130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 17
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 17
atgaacaaac cgcagagctg ggaaacgcgt gcggaaaccg tgagcctgta tgcctttacc 60
cacatgccga gcctacgtca gcgtggcacc atggtggtga cccatggcga aggcccgtat 120
atcgtggatg tgcatggccg tcgttatctg gatgcgaaca gcggcctgtt caacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggccttc cgtataacag cgtgtttggc ctgccgctgc cgggctttct gcatctgacc 540

```
tgcccgcatt attggcgtta tggcgaagaa ggcgaaaccg aagaacagtt tgtcgcgcgt        600
ctggcccgtg aactggaaga aaccattcag aaggaaggcg cggataccat tgcgggcttt        660
tttgcggaac cggtgatggg tgcgggcggt gttattaccc cgccaaaagg ctatttcag         720 gcgattctga ccatcctgcg caaatatgat attccggtga tcagcgatga agtgatttgc        780
ggctttggtc gtaccggcaa cacctggggc tgcgtgacct atgatttac cccggatgcg         840 attattagca gtaaaaacct aaccgcgggt tttttccag taggagcggt gattttgggg         900
ccggaactga gcaaacgtct ggaaaccgcg attgaagcga tcgaagaatt tgatcatggt        960
tttaccacag gcggccatcc ggtggggttgt gcgattgcgc tgaaagcgat tgatgtggtg      1020
atgaacgaag gcctggccga aaacgtgcgt cgtctggccc cgcgttttga agaacgtctg      1080
aaacatattg cggaacgtcc gaacattggc gaatatcgtg gtattggctt tatgtgggcg      1140
ctggaagtgg tgaaagataa agcgagcaaa gccccgtttg atggcaacct gagcgtgagc      1200
gaacgtattg cgaacacctg caccgatctg ggactgattt gccgaccgtt gggccagagc      1260
gtggttctgg caccgccgta cattctgacc gaagcgcaga tggatgaaat gttcgataaa      1320
ctggaaaaag cgctggataa agtgtttgcg gaagtggcgt aa                         1362
```

<210> SEQ ID NO 18
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 18

```
Met Asn Lys Pro Gln Ser Trp Glu Thr Arg Ala Glu Thr Val Ser Leu
1               5                   10                  15

Tyr Ala Phe Th

```
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 19
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 19

```
atgaacaaac cgcagagctg ggaaacgcgt gcggaaaccg tgagcctgta tgcctttacc      60
cacatgccga gcctacatca gcgtggcacc atggtgacca cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgtttctga ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
```

```
tttgcggaac cggtgatggg tgcgggcggt gttattaccc cgccaaaagg ctatttt

```
Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
        435                 440                 445

Phe Ala Glu Val Ala
    450

<210> SEQ ID NO 21
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 21
atgaacaaac cgcagagctg ggaaacgcgt gcggaaaccg tgagcctgta tgcctttacc      60
cacatgccga gcctacgtca gcgtggcacc atggtggtaa cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg cgccatgagc gatcagaccg tgatgctgtc tgaaaaactg     300
gtggaagtga gcccgtttga tagcggccgt gtgtttctga ccaacagcgg cagcgaagcg     360
aacgatacca tggtgaaaat gctgtggttt ctgcatcgtg cggaaggcaa accgcagaaa     420
cgtaaaattc tgaccctgaa gcaggcgtat catggctcca ccgcggtgag cgcgagcatg     480
accggcatcc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggccagtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
```

```
attattagca gtaaaaacct aaccgcgggt tttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc gcgttttga agaacgtctg    1080 aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacaccctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 22
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 22

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Ser Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 23
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 23
atgaacaaac cgcagagctg ggaaacgcgt gcggaaacct atagcctgta tgcctttacc     60
cacatgccga gcctacatca gcgtggcacc atggtggtga cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga acgttttccg    240
ggctatcatg cgttttacgg cctgatgagc gatcagaccg tgatgctgtc tgaaaaactg    300
gtggaagtga gcccgtttga tagcggccgt gtgtttctga ccaacagcgg cagcgaagcg    360
aacgatacca tggtgaaaat gctgtggttt ctgcatcgtg cggaaggcaa accgcagaaa    420
cgtaaaattc tgaccctgaa gcaggcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
```

```
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt atgtgggcg     1140 ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agagtttgcg gaagtggcgt aa                      1362
```

<210> SEQ ID NO 24
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 24

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
```

```
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
        435                 440                 445

Phe Ala Glu Val Ala
    450

<210> SEQ ID NO 25
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 25
atgaacaaac cgcagagctg ggaaacgcgt gcggaaaccg tgagcctgta tgcctttacc     60
cacatgccga gcctacatca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
```

```
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

```
<210> SEQ ID NO 26
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 26
```

```
Met Asn Lys Pro Gln Ser Trp Glu Thr Arg Ala Glu Thr Val Ser Leu
  1               5                  10                  15

Tyr Ala Phe Thr His Met Pro Ser Leu His Gln Arg Gly Thr Met Val
             20                  25                  30

Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320
```

-continued

```
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 27
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 27
atgaacaaac cgcagagctg ggaaacgcgt gcggaaaccg tgagcctgta tgcctttacc     60
cacatgccga gcctacgtca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg cgccatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gcaggcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
```

```
gtggttctgg caccgccgta cattctgacc gaagcgcaga tggatgaaat gttcgataaa    1320
ctggaaaaag cgctggataa agtgtttgcg gaagtggcgt aa                        1362
```

<210> SEQ ID NO 28
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 28

```
Met Asn Lys Pro Gln Ser Trp Glu Thr Arg Ala Glu Thr Val Ser Leu
  1               5                  10                  15

Tyr Ala Phe Thr His Met Pro Ser Leu Arg Gln Arg Gly Thr Met Val
             20

```
Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450
```

<210> SEQ ID NO 29
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 29

```
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgtttgtga ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgatttac cccggatgcg     840
attattagca gtaaaaacct aaccgcgggt ttttttccag taggagcggt gatttttgggg    900
ccggaactga gcaaacgtct ggaaaccgcg attgaagcga tcgaagaatt tgatcatggt     960
tttaccacag cggccatcc ggtgggttgt gcgattgcgc tgaaagcgat tgatgtggtg    1020
atgaacgaag gcctggccga aacgtgcgt cgtctggccc gcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

```
<210> SEQ ID NO 30
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 30
```

Met Asn Lys Pro Gln Ser Tr 370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Leu Gly Gln Ser Val Val Leu Ala Pro Pro Tyr Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 31
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 31
atgaacaaac cgcagagctg ggaaacgcgt gcggaaaccg tgagcctgta tgcctttacc 60
cacatgccga gcctacatca gcgtggcacc atggtggtga cccatggcga aggcccgtat 120
atcgtggatg tgcatggccg tcgttatctg gatgcgaaca gcggcctgtt caacatggtg 180
gcgggctttg atcataaagg cctgattgat gcggcgaaag cgcagtatga acgttttccg 240
ggctatcatg cgttttacgg ccgcatgagc gatcagaccg tgatgctgtc tgaaaaactg 300
gtggaagtga gcccgtttga tagcggccgt gtgtttgtga ccaacagcgg cagcgaagcg 360
aacgatacca tggtgaaaat gctgtggttt ctgcatcgtg cggaaggcaa accgcagaaa 420
cgtaaaattc tgaccctgaa gcaggcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 32
<211> LENGTH: 453
<212> TYPE: PRT
<213> ORGANISM: Artificial Sequence
<220> FEATURE:

<223> OTHER INFORMATION: Engineered variant of V. fluvialis transaminase

<400> SEQUENCE: 32

```
Met Asn Lys Pro G

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 33
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 33
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgacccctga gcaggcgtat catggctcca ccgcggtgag cgcgagcatg     480
accggcatcc gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag cggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362

<210> SEQ ID NO 34
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 34

Met Asn Lys Pro Gln Ser Trp Glu Thr Arg Ala Glu Thr Val Ser Leu

-continued

```
1               5                   10                  15
Tyr Ala Phe Thr His Met Pro Ser Leu Arg Gln Arg Gly Thr Met Val
                20                  25                  30
Val Thr His Gly Glu Gly Pro Tyr Ile Val Asp Val His Gly Arg Arg
                35                  40                  45
Tyr Leu Asp Ala Asn Ser Gly Leu Phe Asn Met Val Ala Gly Phe Asp
                50                  55                  60
His Lys Gly Leu Ile Asp Ala Lys Ala Gln Tyr Glu Arg Phe Pro
65                  70                  75                  80
Gly Tyr His Ala Phe Tyr Gly Arg Met Ser Asp Gln Thr Val Met Leu
                    85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Met Leu
                115                 120                 125
Trp Phe Leu His Arg Ala Glu Gly Lys Pro Gln Lys Arg Lys Ile Leu
                130                 135                 140
Thr Leu Lys Gln Ala Tyr His Gly Ser Thr Ala Val Ser Ala Ser Met
145                 150                 155                 160
Thr Gly Ile Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
210                 215                 220
Val Met Gly Ala Gly Gly Val Ile Thr Pro Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ser Ser Lys Asn Leu Thr
                275                 280                 285
Ala Gly Phe Phe Pro Val Gly Ala Val Ile Leu Gly Pro Glu Leu Ser
                290                 295                 300
Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                    325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Val Val
                370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
                420                 425                 430
```

Gln Met Asp Glu Met Phe Asp Lys Leu Glu Lys Ala Leu Asp Lys Val
        435                 440                 445

Phe Ala Glu Val Ala
    450

<210> SEQ ID NO 35
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 35

| | | | | | |
|---|---|---|

-continued

```
Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
                115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
                290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Val Val
                370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
```

<210> SEQ ID NO 37
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 37

```
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgcatgagc gatcagaccg tgatgctgtc tgaaaaactg     300
gtggaagtga gcccgtttga tagcggccgt gtgtttctga ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgatttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                        1362
```

<210> SEQ ID NO 38
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 38

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Phe Asn Met Val Ala Gly Phe Asp
        50                  55                  60
```

His Lys Gly Leu Ile Asp Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
            115                 120                 125

Trp Phe Leu His Arg Ala Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
450

<210> SEQ ID NO 39
<211> LENGTH: 1362

<212> TYPE: DNA
<213> ORGANISM: Artificial Sequence
<220> FEATURE:
<223> OTHER INFORMATION: Engineered variant of V. fluvialis transaminase

<400> SEQUENCE: 39

```
atgaacaaac cgcagagctg ggaaacgcgt gcggaaaccg tgagcctgta tgcctttacc         60
cacatgccga gcctacgtca gcgtggcacc atggtggtga c

```
                85                  90                  95
Ser Glu Lys Leu Val Glu Val Ser Pro Phe Asp Ser G

<400> SEQUENCE: 41

```
atgaacaaac cgcagagctg ggaaacgcgt gcggaaaccg tgagcctgta tgcctttacc      60
cacatgccga gcctacgtca gcgtggcacc atggtggtga cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga acgttttccg    240
ggctatcatg cgttttacgg cctgatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc gtataacag cgtgtttggc ctgccgctgc cgggcttcct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt tttttccag taggagcggt gattttgggg    900
ccggaactga gcaaacgtct ggaaccgcg attgaagcga tcgaagaatt tgatcatggt    960
tttaccacag gcggccatcc ggtgggttgt gcgattgcgc tgaaagcgat tgatgtggtg  1020
atgaacgaag cctggccga aaacgtgcgt cgtctggccc gcgttttga agaacgtctg  1080
aaacatattg cggaacgtcc gaacattggc gaatatcgtg gtattggctt tatgtgggcg  1140
ctggaagtgg tgaaagataa agcgagcaaa gccccgtttg atggcaacct gagcgtgagc  1200
gaacgtattg cgaacacctg caccgatctg ggactgattt gccgaccgtt gggccagagc  1260
gtggttctgg caccgccgta cattctgacc gaagcgcaga tggatgaaat gttcgataaa  1320
ctggaaaaag cgctggataa agtgtttgcg gaagtggcgt aa                    1362
```

<210> SEQ ID NO 42
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 42

```
Met Asn Lys Pro Gln Ser Trp Glu Thr Arg Ala Glu Thr Val Ser Leu
1               5                  10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110
```

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 43
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 43
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120

-continued

```
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgtttgtga ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc gtataacag cgtgtttggc ctgccgctgc gggctttct gcatctgacc      540 tgcccgcatt attggcgtta tggcgaagaa ggcgaaaccg aagaacagtt tgtcgcgcgt    600
ctggcccgtg aactggaaga accattcag aaggaaggcg cggataccat tgcgggcttt      660
tttgcggaac cggtgatggg tgcggccggt gttattaccc cgccaaaagg ctatttcag     720 gcgattctga ccatcctgcg caaatatgat attccggtga tcagcgatga agtgatttgc    780
ggctttggtc gtaccggcaa cacctggggc tgcgtgacct atgatttac cccggatgcg      840 attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc gcgtttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 44
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 44

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140
```

```
Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Thr
        195                 200                 205

Ile Gln Lys Glu Gly Ala Asp Thr Ile Ala Gly Phe Phe Ala Glu Pro
    210                 215                 220

Val Met Gly Ala Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Gly Arg Pro Asn
    355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 45
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 45
atgaacaaac cgcagagctg ggaaacgcgt gcggaaaccg tgagcctgta tgcctttacc        60
cacatgccga gcctacgtca gcgtggcacc atggtggtaa cccatggcga aggcccgtat       120
atcgtggatg tgcatggccg tcgttatctg gatgcgaaca gcggcctgtt caacatggtg       180
gcgggctttg atcataaagg cctgattgat gcggcgaaag cgcagtatga acgttttccg       240
```

-continued

```
ggctatcatg cgttttacgg cctgatgagc gatcagaccg tgatgctgtc tgaaaaactg      300
gtggaagtga gcccgtttga tagcggccgt gtgtttctga ccaacagcgg cagcgaagcg      360
aacgatacca tggtgaaaat gctgtggttt ctgcatcgtg cggaaggcaa accgcagaaa      420
cgtaaaattc tgaccctgaa gcaggcgtat catggctcca ccgcggtgag cgcgagcatg      480
accggcatcc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattaccc cgccaaaagg ctattttcag      720
gcgattctga ccatcctgcg caaatatgat attccggtga tcagcgatga agtgatttgc      780
ggctttggtc gtaccggcaa cacctggggc tgcgtgacct atgattttac cccggatgcg      840
attattagca gtaaaaacct aaccgcgggt tttttttccag taggagcggt gattttgggg      900
ccggaactga gcaaacgtct ggaaaccgcg attgaagcga tcgaagaatt tgatcatggt      960
tttaccacag gcggccatcc ggtgggttgt gcgattgcgc tgaaagcgat tgatgtggtg     1020
atgaacgaag gcctggccga aaacgtgcgt cgtctggccc gcgttttga agaacgtctg      1080
aaacatattg cggaacgtcc gaacattggc gaatatcgtg gtattggctt atgtgggcg      1140
ctggaagtgg tgaaagataa agcgagcaaa gccccgtttg atggcaacct gagcgtgagc      1200
gaacgtattg cgaacacctg caccgatctg ggactgattt gccgaccgtt gggccagagc      1260
gtggttctgg caccgccgta cattctgacc gaagcgcaga tggatgaaat gttcgataaa      1320
ctggaaaaag cgctggataa agtgtttgcg gaagtggcgt aa                         1362
```

<210> SEQ ID NO 46
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 46

```
Met Asn Lys Pro Gln Ser Tr

```
                165                 170                 175
Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 47
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 47

```
atgaacaaac cgcagagctg ggaaacgcgt gcggaaaccg tgagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
```

```
cgtaaaattc tgaccctgaa gcaggcgtat catggctcca ccgcggtgag cgcgagcatg      480
accggcatcc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattaccc cgccaaaagg ctatttcag      720 gcgattctga ccatcctgcg caaatatgat attccggtga tcagcgatga agtgatttgc      780
ggctttggtc gtaccggcaa cacctggggc tgcgtgacct atgatttac cccggatgcg      840 attattagca gtaaaaacct aaccgcgggt ttttttccag taggagcggt gattttgggg      900
ccggaactga gcaaacgtct ggaaaccgcg attgaagcga tcgaagaatt tgatcatggt      960
tttaccacag gcggccatcc ggtgggttgt gcgattgcgc tgaaagcgat tgatgtggtg     1020
atgaacgaag gcctggccga aaacgtgcgt cgtctggccc cgcgttttga agaacgtctg     1080
aaacatattg cggaacgtcc gaacattggc gaatatcgtg gtattggctt tatgtgggcg     1140
ctggaagtgg tgaaagataa agcgagcaaa gccccgtttg atggcaacct gagcgtgagc     1200
gaacgtattg cgaacacctg caccgatctg ggactgattt gccgaccgtt gggccagagc     1260
gtggttctgg caccgccgta cattctgacc gaagcgcaga tggatgaaat gttcgataaa     1320
ctggaaaaag cgctggataa agtgtttgcg gaagtggcgt aa                        1362

<210> SEQ ID NO 48
<211> LENGTH: 453
<212> TYPE: PRT
<213> ORGANISM: Artificial Sequence
<220> FEATURE:
<223> OTHER INFORMATION: Engineered variant of V. fluvialis trans

```
Thr Glu Glu Gln Phe Val Ala Arg Leu Ala Arg Glu Leu Glu Glu Thr
        195                 200                 205
Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450
```

<210> SEQ ID NO 49
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 49

```
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgtttgtga ccaacagcgg cagcgaagcg     360
aacgatacca tggtgaaaat gctgtggttt ctgcatcgtg cggaaggcaa accgcagaaa     420
cgtaaaattc tgaccctgaa gcgtgcgtat catggctcca ccgcggtgag cgcgagcatg     480
accggccttc cgtataacag cgtgtttggc ctgccgctgc cgggctttct gcatctgacc     540
```

-continued

```
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                       1362
```

<210> SEQ ID NO 50
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 50

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Arg Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

```
Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 51
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 51

```
atgaacaaac cgcagagctg ggaaacgcgt gcggaaaccg tgagcctgta tgcctttacc     60
cacatgccga gcctacatca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg cgccatgagc gatcagaccg tgatgctgtc tgaaaaactg    300
gtggaagtga gcccgtttga tagcggccgt gtgtttgtga ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
```

-continued

```
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc gcgttttga agaacgtctg    1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 52
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 52

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp

```
            245                 250                 255
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 53
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 53
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtg aacatggtg      180 gcgggctttg atcataaagg cctgattgat gcggcgaaag cgcagtatga acgttttccg     240
ggctatcatg cgttttacgg ccgcatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa aacgcgtat catggctcca ccgcggtgag cgcgagcatg     480
accggccttc gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactgaaga aaccattcag aaggaaggcg cggataccat tgcgggcttt     660
tttgcggaac cggtgatggg tgcgggcggt gttattaccc cgccaaaagg ctatttttcag    720 gcgattctga ccatcctgcg caaatatgct attccggtga tcagcgatga agtgatttgc     780
ggctttggtc gtaccggcaa caccctgggc tgcgtgacct atgattttac cccggatgcg     840
```

```
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 54
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 54

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Ala Ile Pro Val Ile Ser Asp
                245                 250                 255

Glu Val Ile Cys Gly Phe Gly Arg Thr Gly Asn Thr Trp Gly Cys Val
            260                 265                 270
```

-continued

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 55
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 55

```
atgaacaaac cgcagagctg ggaaacgcgt gcggaaaccg tgagcctgta tgcctttacc     60
cacatgccga gcctacgtca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg cctgatgagc gatcagaccg tgatgctgtc tgaaaaactg    300
gtggaagtga gcccgtttga tagcggccgt gtgtttctga ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
```

-continued

```
atgaacgaag gcctggccga aaacgtgcgt cgtctggccc cgcgttttga agaacgtctg      1080
aaacatattg cggaacgtcc gaacattggc gaatatcgtg gtattggctt tatgtgggcg      1140
ctggaagtgg tgaaagataa agcgagcaaa gccccgtttg atggcaacct gagcgtgagc      1200
gaacgtattg cgaacacctg caccgatctg ggactgattt gccgaccgtt gggccagagc      1260
gtggttctgg caccgccgta cattctgacc gaagcgcaga tggatgaaat gttcgataaa      1320
ctggaaaaag cgctggataa agtgtttgcg gaagtggcgt aa                         1362
```

<210> SEQ ID NO 56
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 56

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Arg Leu Lys His Ile Ala Glu Arg Pro Asn
    355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 57
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 57

| | | |
|---|---|---|
| atgaacaaac cgcagagctg ggaaacgcgt gcggaaaccg tgagcctgta tgcctttacc | 60 |
| cacatgccga gc

```
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 58
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 58

| Met<br>1 | Asn | Lys | Pro | Gln<br>5 | Ser | Trp | Glu | Thr | Arg<br>10 | Ala | Glu | Thr | Val | Ser<br>15 | Leu |
|---|---|---|---|---|---|---|---|---|---|---|---|---|---|---|---|
| Tyr | Ala | Phe | Thr<br>20 | His | Met | Pro | Ser<br>25 | Leu | His | Gln | Arg | Gly<br>30 | Thr | Met | Val |
| Val | Thr | His<br>35 | Gly | Glu | Gly | Pro<br>40 | Tyr | Ile | Val | Asp | Val<br>45 | His | Gly | Arg | Arg |
| Tyr | Leu<br>50 | Asp | Ala | Asn | Ser | Gly<br>55 | Leu | Phe | Asn | Met | Val<br>60 | Ala | Gly | Phe | Asp |
| His<br>65 | Lys | Gly | Leu | Ile | Asp<br>70 | Ala | Ala | Lys | Ala | Gln<br>75 | Tyr | Glu | Arg | Phe | Pro<br>80 |
| Gly | Tyr | His | Ala | Phe<br>85 | Tyr | Gly | Ala | Met | Ser<br>90 | Asp | Gln | Thr | Val | Met<br>95 | Leu |
| Ser | Glu | Lys | Leu<br>100 | Val | Glu | Val | Ser | Pro<br>105 | Phe | Asp | Ser | Gly | Arg<br>110 | Val | Phe |
| Leu | Thr | Asn<br>115 | Ser | Gly | Ser | Glu | Ala<br>120 | Asn | Asp | Thr | Met | Val<br>125 | Lys | Met | Leu |
| Trp | Phe<br>130 | Leu | His | Arg | Ala | Glu<br>135 | Gly | Lys | Pro | Gln | Lys<br>140 | Arg | Lys | Ile | Leu |
| Thr<br>145 | Leu | Lys | Asn | Ala | Tyr<br>150 | His | Gly | Ser | Thr | Ala<br>155 | Val | Ser | Ala | Ser | Met<br>160 |
| Thr | Gly | Leu | Pro | Tyr<br>165 | Asn | Ser | Val | Phe | Gly<br>170 | Leu | Pro | Leu | Pro | Gly<br>175 | Phe |
| Leu | His | Leu | Thr<br>180 | Cys | Pro | His | Tyr | Trp<br>185 | Arg | Tyr | Gly | Glu | Glu<br>190 | Gly | Glu |
| Thr | Glu | Glu<br>195 | Gln | Phe | Val | Ala | Arg<br>200 | Leu | Ala | Arg | Glu | Leu<br>205 | Glu | Glu | Thr |
| Ile | Gln<br>210 | Lys | Glu | Gly | Ala | Asp<br>215 | Thr | Ile | Ala | Gly | Phe<br>220 | Phe | Ala | Glu | Pro |
| Val<br>225 | Met | Gly | Ala | Gly | Gly<br>230 | Val | Ile | Thr | Pro | Pro<br>235 | Lys | Gly | Tyr | Phe | Gln<br>240 |
| Ala | Ile | Leu | Thr | Ile<br>245 | Leu | Arg | Lys | Tyr | Asp<br>250 | Ile | Pro | Val | Ile | Ser<br>255 | Asp |
| Glu | Val | Ile | Cys<br>260 | Gly | Phe | Gly | Arg | Thr<br>265 | Gly | Asn | Thr | Trp | Gly<br>270 | Cys | Val |
| Thr | Tyr | Asp<br>275 | Phe | Thr | Pro | Asp | Ala<br>280 | Ile | Ile | Ser | Ser | Lys<br>285 | Asn | Leu | Thr |
| Ala | Gly<br>290 | Phe | Phe | Pro | Val | Gly<br>295 | Ala | Val | Ile | Leu | Gly<br>300 | Pro | Glu | Leu | Ser |
| Lys<br>305 | Arg | Leu | Glu | Thr | Ala<br>310 | Ile | Glu | Ala | Ile | Glu<br>315 | Glu | Phe | Asp | His | Gly<br>320 |
| Phe | Thr | Thr | Gly | Gly<br> | His | Pro | Val | Gly | Cys<br> | Ala | Ile | Ala | Leu | Lys<br> | Ala |

```
                          325                 330                 335
Ile Asp Val Val Met Asn Glu Gly Leu Ala Glu Asn Val Arg Arg Leu
                340

```
ctggaaaaag cgctggataa agtgtttgcg gaagtggcgt aa                    1362
```

<210> SEQ ID NO 60
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 60

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Gly Lys Pro Gln Lys Arg Lys Ile Leu
    130                 135                 140

Thr Leu Lys Arg Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 61
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 61
atgaacaaac cgcagagctg ggaaacgcgt gcggaaa

```
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 62
```

Met Asn Lys Pro Gln Ser Trp Glu Thr Arg Ala Glu Thr Val Ser

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Ala Pro Pro Tyr Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 63
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 63

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggcatcc gtataacag cgtgtttggc ctgccggctc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaaa ccggtgatgg gtgcggccgg gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgatttac cccgatgcg     840
attattagcg ccaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc gcgtttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atgcaacct gagcgtgggt    1200
gaacgtattg cgaacacctg caccgatctg ggactgattt gtcgaccgat gggccagagc    1260
gtggttctgg tgccgccgta cattctgacc gaagcgcaga tggatgaaat gttcgataaa    1320
ctggaaaaag cgctggataa agtgtttgcg gaagtggcgt aa                       1362
```

<210> SEQ ID NO 64
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 64

```
Met Asn Lys Pro Gln Ser Trp Glu Thr Arg Ala Glu Thr Tyr Ser Leu
  1               5                  10                  15

Tyr Ala Phe Thr His Met Pro Ser Leu His Gln Arg Gly Thr Met Val
             20                  25                  30

Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
     50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Leu Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
```

```
                    405                 410                 415
Met Gly Gln Ser Val Val Leu Val Pro Pro Tyr Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 65
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 65
atgaacaaac cgcagagctg ggaaacgcgt gcggaaacct atagcctgta tgcctttacc      60
cacatgccga gcctacatca gcgtggcacc atggtgacca cccatggcga aggcccgtat    120
atcgtggatg tgcatggccg tcgttatctg gatgcgaaca gcggcctgtg aacatggtg     180 gcgggctttg atcataaagg cctgattgat gcggcgaaag cgcagtatga acgttttccg    240
ggctatcatg cgtttacgg cctgatgagc gatcagaccg tgatgctgtc tgaaaaactg     300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggctttc cgtataacag cgtgtttggc ctgccggctc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcggccggt gttattaccc cgccaaaagg ctatttttcag   720 gcgattctga ccatcctgcg caaatatgat attccggtga tcagcgatga agtgatttgc    780
ggctttggtc gtaccggcaa cacctggggc tgcgtgacct atgattttac cccggatgcg    840
attattagcg ccaaaaacct aaccgcgggt tttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc gcgtttttga gaacgtctg    1080 aaacatattg cggaacgtcc gaacattggc gaatatcgtg gtattggctt atgtgggcg    1140 ctggaagccg tgaaagataa agcgagcaaa gccccgtttg atggcaacct gagcgtgggt   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362

<210> SEQ ID NO 66
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 66

Met Asn Lys Pro Gln Ser Trp Glu Thr Arg Ala Glu Thr Tyr Ser Leu
1               5                   10                  15
```

-continued

```
Tyr Ala Phe Thr His Met Pro Ser Leu His Gln Arg Gly Thr Met Val
             20                  25                  30

Thr Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Leu Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
            275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430
```

```
Gln Met Asp Glu Met Phe Asp Lys Leu Glu Lys Ala Leu Asp Lys Val
            435                 440                 445

Phe Ala Glu Val Ala
    450
```

<210> SEQ ID NO 67
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 67

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca cgggcctgtg gaacatggtg     180
gcgggctttg atcataaagg cctgattgat gcggcgaaag cgcagtatga acgttttccg     240
ggctatcatg cgtttgatgg ccgtatgagc gatcagaccc tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggctttc gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt tttttttccag taggagcggt gattttgggg     900
ccggaactga gcaaacgtct ggaaaccgcg attgaagcga tcgaagaatt tgatcatggt     960
tttaccacac acggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt atgtgggcg     1140
ctggaagtgg tgaaagataa agcgagcaaa gccccgtttg atggcaacct gagcgtgggt    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                        1362
```

<210> SEQ ID NO 68
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 68

```
Met Asn Lys Pro Gln Ser Trp Glu Thr Arg Ala Glu Thr Tyr Ser Leu
  1               5                  10                  15

Tyr Ala Phe Thr His Met Pro Ser Leu His Gln Arg Gly Thr Met Val
                 20                  25                  30

Val Thr His Gly Glu Gly Pro Tyr Ile Val Asp Val His Gly Arg Arg
```

-continued

```
                35                  40                  45
Tyr Leu Asp Ala Asn Ser Gly Leu Trp Asn Met Val Ala Gly Phe Asp
             50                  55                  60
His Lys Gly Leu Ile Asp Ala Ala Lys Ala Gln Tyr Glu Arg Phe Pro
 65                  70                  75                  80
Gly Tyr His Ala Phe Asp Gly Arg Met Ser Asp Gln Thr Val Met Leu
                 85                  90                  95
Ser Glu Lys Leu Val Glu Val Ser Pro Phe Asp Ser Gly Arg Val Phe
            100                 105                 110
Tyr Thr Asn Ser Gly Ser Glu Ala Asn Asp Thr Met Val Lys Met Leu
            115                 120                 125
Trp Phe Leu His Arg Ala Glu Gly Lys Pro Gln Lys Arg Lys Ile Leu
        130                 135                 140
Thr Leu Lys Asn Ala Tyr His Gly Ser Thr Ala Val Ser Ala Ser Met
145                 150                 155                 160
Thr Gly Phe Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
            195                 200                 205
Ile Gln Lys Glu Gly Ala Asp Thr Ile Ala Gly Phe Phe Ala Glu Pro
        210                 215                 220
Val Met Gly Ala Gly Gly Val Ile Thr Pro Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
            275                 280                 285
Ala Gly Phe Phe Pro Val Gly Ala Val Ile Leu Gly Pro Glu Leu Ser
        290                 295                 300
Lys Arg Leu Glu Thr Ala Ile Glu Ala Ile Glu Glu Phe Asp His Gly
305                 310                 315                 320
Phe Thr Thr His Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
            355                 360                 365
Ile Gly Glu Tyr Arg Gly Ile Gly Phe Met Trp Ala Leu Glu Val Val
        370                 375                 380
Lys Asp Lys Ala Ser Lys Ala Pro Phe Asp Gly Asn Leu Ser Val Gly
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
            435                 440                 445
Phe Ala Glu Val Ala
            450
```

<210> SEQ ID NO 69
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 69

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgtttgatgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggctttc gtataacag caagtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagcg ccaaaaacct aaccgcgggt ttttttccag taggagcggt gattttgggg     900
ccggaactga gcaaacgtct ggaaaccgcg attgaagcga tcgaagaatt tgatcatggt     960
tttaccacac acggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gtattggctt tatgtgggcg    1140
ctggaagccg tgaaagataa agcgagcaaa gccccgtttg atggcaacct gagcgtgggt    1200
gaacgtattg cgaacaccct caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 70
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 70

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60
```

```
His Lys Gly Leu Ile Asp Ala Ala Lys Ala Gln Tyr Glu Arg Phe Pro
 65                  70                  75                  80

Gly Tyr His Ala Phe Asp Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Lys Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 71
<211> LENGTH: 1362
<212> TYPE: DNA
```

<213> ORGANISM: Artificial Sequence
<220> FEATURE:
<223> OTHER INFORMATION: Engineered variant of V. fluvialis transaminase

<400> SEQUENCE: 71

```
atgaacaaac cgcagagctg ggaaacgcgt gcggaaacct atagcctgta tgcctttacc      60
cacatgccga gcctacatca gcgtggcacc atggtggtga c

```
Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
            275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Arg Leu Lys His Ile Ala Glu Arg Pro Asn
            355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 73
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 73
```

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgtttgatgg ccgtatgagc gatcagaccg tgatgctgtc tgaaaaactg     300
gtggaagtga gcccgtttga tagcggccgt gtgtttata caacagcgg cagcgaagcg      360 aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggctttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattaccc cgccaaaagg ctatttcag      720 gcgattctga ccatcctgcg caaatatgat attccggtga tcagcgatga agtgatttgc     780
ggctttggtc gtaccggcaa cacctggggc tgcgtgacct atgatttac cccggatgcg     840 attattagca gtaaaaacct aaccgcgggt ttttttccag taggagcggt gattttgggg     900
ccggaactga gcaaacgtct ggaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc gcgttttga agaacgtctg    1080 aaacatattg cggaacgtcc gaacattggc gaatatcgtg gtattggctt tatgtgggcg    1140
ctggaagccg tgaaagataa agcgagcaaa gccccgtttg atggcaacct gagcgtgggt    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 74
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 74

```
Met Asn Lys Pro Gln Ser Trp Glu Thr Arg Ala Glu Th

```
              115                 120                 125
Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 75
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 75
atgaacaaac cgcagagctg ggaaacgcgt gcggaaacct atagcctgta tgcctttacc      60
cacatgccga gcctacatca gcgtggcacc atggtggtga cccatggcga aggcccgtat     120
```

```
atcgtggatg tgcatggccg tcgttatctg gatgcgaaca gcggcctgtg gaacatggtg      180
gcgggctttg atcataaagg cctgattgat gcggcgaaag cgcagtatga acgttttccg      240
ggctatcatg cgtttgatgg ccgtatgagc gatcagaccg tgatgctgtc tgaaaaactg      300
gtggaagtga gcccgtttga tagcggccgt gtgttttata ccaacagcgg cagcgaagcg      360
aacgatacca tggtgaaaat gctgtggttt ctgcatcgtg cggaaggcaa accgcagaaa      420
cgtaaaattc tgaccctgaa gaacgcgtat catggctcca ccgcggtgag cgcgagcatg      480
accggctttc gtataacag cgtgtttggc ctgccggctc cgggctttct gcatctgacc       540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcggcggt gttattaccc cgccaaaagg ctattttcag       720
gcgattctga ccatcctgcg caaatatgat attccggtga tcagcgatga agtgatttgc      780
ggctttggtc gtaccggcaa cacctggggc tgcgtgacct atgatttac cccggatgcg       840 attattagca gtaaaaacct aaccgcgggt ttttttccag taggagcggt gattttgggg      900
ccggaactga gcaaacgtct ggaaaccgcg attgaagcga tcgaagaatt tgatcatggt      960
tttaccacag gcgccatcc ggtgggttgt gcgattgcgc tgaaagcgat tgatgtggtg      1020
atgaacgaag gcctggccga aaacgtgcgt cgtctggccc cgcgttttga gaacgtctg      1080 aaacatattg cggaacgtcc gaacattggc gaatatcgtg gtattggctt tatgtgggcg      1140
ctggaagtgg tgaaagataa agcgagcaaa gccccgtttg atggcaacct gagcgtgggt      1200
gaacgtattg cgaacacctg caccgatctg ggactgattt gccgaccgtt gggccagagc      1260
gtggttctgg caccgccgta cattctgacc gaagcgcaga tggatgaaat gttcgataaa      1320
ctggaaaaag cgct

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
            210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
            435                 440                 445

Phe Ala Glu Val Ala
    450

<210> SEQ ID NO 77
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 77 atgaacaa

-continued

```
gtggaagtga gcccgtttga tagcggccgt gtgttttata ccaacagcgg cagcgaagcg      360
aacgatacca tggtgaaaat gctgtggttt ctgcatcgtg cggaaggcaa accgcagaaa      420
cgtaaaattc tgaccctgaa gaacgcgtat catggctcca ccgcggtgag cgcgagcatg      480
accggctttc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga accattcag aaggaaggcg cggataccat tgcgggcttt       660
tttgcggaac cggtgatggg tgcgggcggt gttattaccc cgccaaaagg ctatttcag      720
gcgattctga ccatcctgcg caaatatgat attccggtga tcagcgatga agtgatttgc      780
ggctttggtc gtaccggcaa cacctggggc tgcgtgacct atgatttac cccggatgcg       840
attattagcg ccaaaaacct aaccgcgggt tttttccag taggagcggt gattttgggg       900
ccggaactga gcaaacgtct ggaaaccgcg attgaagcga tcgaagaatt tgatcatggt      960
tttaccacac acggccatcc ggtggttgt gcgattgcgc tgaaagcgat tgatgtggtg      1020
atgaacgaag gcctggccga aaacgtgcgt cgtctggccc cgcgttttga agaacgtctg      1080
aaacatattg cggaacgtcc gaacattggc gaatatcgtg gtattggctt tatgtgggcg      1140
ctggaagtgg tgaaagataa agcgagcaaa gccccgtttg atggcaacct gagcgtgggt      1200
gaacgtattg cgaacacctg caccgatctg ggactgattt gccgaccgtt gggccagagc     1260
gtggttctgg caccgccgta cattctgacc gaagcgcaga tggatgaaat gttcgataaa     1320
ctggaaaaag cgctggataa agtgtttgcg gaagtggcgt aa                        1362
```

```
<210> SEQ ID NO 78
<211> LENGTH: 453
<212> TYPE: PRT
<213> ORGANISM: Artificial Sequence
<220> FEATURE:
<223> OTHER INFORMATION: Engineered variant of V. fluvialis trans Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 79
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 79
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgtttgatgg ccgtatgagc gatcagaccg tgatgctgtc tgaaaaactg     300
gtggaagtga gcccgtttga tagcggccgt gtgtttttata ccaacagcgg cagcgaagcg     360
aacgatacca tggtgaaaat gctgtggttt ctgcatcgtg cggaaggcaa accgcagaaa     420

-continued

```
cgtaaaattc tgaccctgaa gaacgcgtat catggctcca ccgcggtgag cgcgagcatg    480
accggctttc cgtataacag cgtgtttggc ctgccggctc cgggcttcct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgatttttac cccggatgcg    840 attattagcg ccaaaaacct aaccgcgggt ttttttccag taggagcggt gattttgggg    900
ccggaactga gcaaacgtct ggaaaccgcg attgaagcga tcgaagaatt tgatcatggt    960
tttaccacac acggccatcc ggtgggttgt gcgattgcgc tgaaagcgat tgatgtggtg   1020
atgaacgaag gcctggccga aacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgggt   1200
gaacgtattg cgaacaccctg caccgatctg ggactgattt gccgaccgct gggccagagc   1260
gtggttctgg caccgccgta cattctgacc gaagcgcaga tggatgaaat gttcgataaa   1320
ctggaaaaag cgctggataa agtgtttgcg gaagtggcgt aa                     1362
```

<210> SEQ ID NO 80
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 80

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
```

```
                195                 200                 205
Ile Gln Lys Glu Gly Ala Asp Thr Ile Ala Gly Phe Phe Ala Glu Pro
    210                 215                 220

Val Met Gly Ala Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                    245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ala Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                    325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
        370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                    405                 410                 415

Leu Gly Gln Ser Val Val Leu Ala Pro Pro Tyr Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 81
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 81
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca gcggcctgta taacatggtg     180
gcgggctttg atcataaagg cctgattgcg gcggcgaaag cgcagtatga acgttttccg     240
ggctatcatg cgttttacgg ccgtatgagc gatcagaccg tgatgctgtc tgaaaaactg     300
gtggaagtga gcccgtttcc aagcggccgt gtgttttata ccaacagcgg cagcgaagcg     360
aacgatacca tggtgaaaat gctgtggttt ctgtttcgtg cggaaggcaa accgcagaaa     420
cgtaaaattc tgaccctgaa gaacgcgtat catggctcca ccgcggtgag cgcgagcatg     480 accggcttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
```

```
ctggcccgtg aactggaaga aaccattcag aaggaaggcg cggataccat tgcgggcttt      660
tttgcggaac cggtgatggg tgcgggcggt gttattaccc cgccaaaagg ctattttcag      720
gcgattctga ccatcctgcg caaatatgat attccggtga tcagcgatga agtgatttgc      780
ggctttggtc gtaccggcaa cacctggggc tgcgtgacct atgattttac cccggatgcg      840
attattagca gtaaaaacct aaccgcgggt tttttccag taggagcggt gattttgggg       900
ccggaactga gcaaacgtct ggaaaccgcg attgaagcga atgaggaatt tgatcatggt      960
tttaccacag gcggccatcc ggtgggttgt gcgattgcgc tgaaagcgat tgatgtggtg     1020
atgaacgaag gcctggccga aaacgtgcgt cgtctggccc cgcgttttga agaacgtctg     1080
aaacatattg cggaacgtcc gaacattggc gaatatcgtg gtattggctt tatgtgggcg     1140
ctggaagtgg tgaaagataa agcgagcaaa gccccgtttg atggtaacct ggttgtgagc     1200
gaacgtattg cgaacaccctg caccgatctg ggactgattt gccgaccgtt gggccagagc    1260
gtggttctgg caccgccgta cattctgacc gaagcgcaga tggatgaaat gttcgataaa     1320
ctggaaaaag cgctggataa agtgtttgcg gatgtggcgt aa                        1362
```

<210> SEQ ID NO 82
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 82

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

```
Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 83
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 83

```
atgaacaaac cgcagagctg ggaaacgcgt gcggaaacct atagcctgta tgcctttacc     60
cacatgccga gcctacatca gcgtggcacc atggtggtga cccatggcga aggcccgtat    120
ctggtggatg tgcatggcaa ccgttatctg gatgcgaaca gcggcctgta taacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
```

```
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaccgcgg attgaagcga ttggggaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggtaaacct ggttgtgagc   1200 gaacgtattg cgaacacctg caccgatctg ggactgattt gccgaccgtt gggccagagc   1260
gtggttatcg cgccgccgta cattctgacc gaagcgcaga tggatgaaat gttcgataaa   1320
ctggaaaaag cgctggataa agtgtttgcg gaagtggcgt aa                      1362
```

<210> SEQ ID NO 84
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 84

```
Met Asn Lys Pro Gln Ser Trp Glu Thr Arg Ala Glu Thr Tyr Ser

```
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 85
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 85

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca gcggcctgta taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
```

```
ccggaactga gcaaacgtct ggaaaccgcg attgaagcga ttggggaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggtaacct ggttgtgagc   1200
gaacgtattg cgaacacctg caccgatctg ggactgattt gccgaccgtt gggccagagc   1260
gtggttctgg cgccgccgta cattctgacc gaagcgcaga tggatgaaat gttcgataaa   1320
ctggaaaaag cgctggataa agtgtttgcg gaagtggcgt aa                      1362
```

<210> SEQ ID NO 86
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 86

```
Met Asn Lys Pro Gln Ser Tr

```
       275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Gly Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Val Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 87
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 87
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca cgcggcctgta taacatggtg    180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttcc aagcggccgt gtgttttata ccaacagcgg cagcgaagcg     360
aacgatacca tggtgaaaat gctgtggttt ctgtttcgtg cggaaggcaa accgcagaaa     420
cgtaaaattc tgaccctgaa gaacgcgtat catggctcca ccgcggtgag cgcgagcatg     480
accggccttc gtataacag cgtgtttggc ctgccgctgc cgggctttct gcatctgacc      540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctatttcag     720 gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt tttttttccag taggagcggt gattttgggg    900
ccggaactga gcaaacgtct ggaaaccgcg attgaagcga ttggggaatt tgatcatggt    960
tttaccacag gcggccatcc ggtgggttgt gcgattgcgc tgaaagcgat tgatgtggtg   1020
```

-continued

```
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atccaaacct gtgggtgagc    1200
gaacgtattg cgaacacctg caccgatctg ggactgattt gccgaccgtt gggccagagc    1260
gtggttctgg cgccgccgta cattctgacg gaagcgcaga tggatgaaat gttcgataaa    1320
ctggaaaaag cgctggataa agtgtttgcg gaagtggcgt aa                       1362
```

<210> SEQ ID NO 88
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 88

```
Met Asn Lys Pro Gln Ser Trp Glu Thr Arg Ala Glu Thr Tyr Ser

```
Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Arg Leu Lys His Ile Ala Glu Arg Pro Asn
        355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Pro Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450
```

<210> SEQ ID NO 89
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 89

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttcc aagcggccgt gtgttttata ccaacagcgg cagcgaagcg     360
aacgatacca tggtgaaaat gctgtggttt ctgtttcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt tttttttccag taggagcggt gattttgggg     900
ccggaactga gcaaacgtct ggaaaccgcg attgaagcga ttgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
```

-continued

```
gaacgtattg cgaacacctg caccgatctg ggactgattt gccgaccgtt gggccagagc    1260
gtggttctgg cgccgccgta cattctgacc gaagcgcaga tgatgaaat gttcgataaa    1320 ctggaaaaag cgctggataa agtgtttgcg gatgtggcgt aa                      1362
```

<210> SEQ ID NO 90
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 90

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450

<210> SEQ ID NO 91
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> S ctggaaaaag cgctggataa agtgtttgcg gatgtggcgt aa                    1362

<210> SEQ ID NO 92
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 92

```
Met Asn Lys Pro Gln Ser Trp Glu Thr Arg Ala Glu Thr Tyr Ser Leu
1               5                  10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Asp Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly As

```
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450

<210> SEQ ID NO 93
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 93
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca gcggcctgta taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttcc aagcggccgt gtgttttata ccaacagcgg cagcgaagcg     360
aacgatacca tggtgaaaat gctgtggttt ctgtttcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga ttggggaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
gaacgtattg cgaacacctg caccgatctg ggactgattt gccgaccgtt gggccagagc    1260
gtggttatcg cgccgccgta cattctgacc gaagcgcaga tggatgaaat gttcgataaa    1320
ctggaaaaag cgctggataa agtgtttgcg gaagtggcgt aa                       1362

<210> SEQ ID NO 94
<211> LENGTH: 453
```

```
<212> TYPE: PRT
<213> ORGANISM: Artificial Sequence
<220> FEATURE:
<223> OTHER INFORMATION: Engineered variant of V. fluvialis transaminase

<400> SEQUENCE: 94
```

| | | | | | | | | | | | | | | |
|---|---|---|---|---|---|---|---|---|

-continued

```
Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 95
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 95

```
atgaacaaac cgcagagctg ggaaacgcgt gcggaaacct atagcctgta tgcctttacc      60
cacatgccga gcctacatca gcgtggcacc atggtggtga cccatggcga aggcccgtat     120
ctggtggatg tgcatggccg tcgttatctg gatgcgaaca gcggcctgta taacatggtg     180
gcgggctttg atcataaagg cctgattgcg gcggcgaaag cgcagtatga acgttttccg     240
ggctatcatg cgttttacgg ccgtatgagc gatcagaccg tgatgctgtc tgaaaaactg     300
gtggaagtga gcccgtttcc aagcggccgt gtgttttata ccaacagcgg cagcgaagcg     360
aacgatacca tggtgaaaat gctgtggttt ctgtttcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga atgaggaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct gtgggtgagc    1200
gaacgtattg cgaacacctg caccgatctg ggactgattt gccgaccgtt gggcagcagc    1260
gtggttctgg cgccgccgta cattctgacc gaagcgcaga tggatgaaat gttcgataaa    1320
ctggaaaaag cgctggataa agtgtttgcg gaagtggcgt aa                       1362
```

<210> SEQ ID NO 96
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 96

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Ala Ala Lys Ala Gln Tyr Glu Arg Phe Pro
65                  70                  75                  80

Gly Tyr His Ala Phe Tyr Gly Arg Met Ser Asp Gln Thr Val Met Leu
            85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
            115                 120                 125

Trp Phe Leu Phe Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
            405                 410                 415
```

```
Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
        450

<210> SEQ ID NO 97
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400

```
Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Pro Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
```

<210> SEQ ID NO 99
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 99

```
atgaacaaac cgcagagctg ggaaacgcgt gcggaaacct atagcctgta tgcctttacc      60
cacatgccga gcctacatca g

```
Tyr Leu Asp Ala Asn Ser Gly Leu Phe Asn Met Val Ala Gly Phe Asp
     50                  55                  60
His Lys Gly Leu Ile Asp Ala Ala Lys Ala Gln Tyr Glu Arg Phe Pro
 65                  70                  75                  80
Gly Tyr His Ala Phe Tyr Gly Arg Met Ser Asp Gln Thr Val Met Leu
                 85                  90                  95
Ser Glu Lys Leu Val Glu Val Ser Pro Phe Asp Ser Gly Arg Val Phe
             100                 105                 110
Tyr Thr Asn Ser Gly Ser Glu Ala Asn Asp Thr Met Val Lys Met Leu
             115                 120                 125
Trp Phe Leu His Arg Ala Glu Gly Lys Pro Gln Lys Arg Lys Ile Leu
130                 135                 140
Thr Leu Lys Asn Ala Tyr His Gly Ser Thr Ala Val Ser Ala Ser Met
145                 150                 155                 160
Thr Gly Ile Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
             180                 185                 190
Thr Glu Glu Gln Phe Val Ala Arg Leu Ala Arg Glu Leu Glu Glu Thr
             195                 200                 205
Ile Gln Lys Glu Gly Ala Asp Thr Ile Ala Gly Phe Phe Ala Glu Pro
210                 215                 220
Val Met Gly Ala Gly Gly Val Ile Thr Pro Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
             260                 265                 270
Thr Tyr Asp Phe Thr Pro Asp Ala Ile Ile Ser Ser Lys Asn Leu Thr
             275                 280                 285
Ala Gly Phe Phe Pro Val Gly Ala Val Ile Leu Gly Pro Glu Leu Ser
290                 295                 300
Lys Arg Leu Glu Thr Ala Ile Glu Ala Ile Gly Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Leu Glu Asn Val Arg Arg Leu
             340                 345                 350
Ala Pro Arg Phe Glu Glu Arg Leu Lys His Ile Ala Glu Arg Pro Asn
             355                 360                 365
Ile Gly Glu Tyr Arg Gly Ile Gly Phe Met Trp Ala Leu Glu Val Val
370                 375                 380
Lys Asp Lys Ala Ser Lys Ala Pro Phe Asp Gly Asn Leu Leu Val Ser
385                 390                 395                 400
Glu Arg Ile Ala Asn Thr Cys Thr Asp Leu Gly Leu Ile Cys Arg Pro
                405                 410                 415
Leu Gly Ser Ser Val Val Leu Ala Pro Pro Tyr Ile Leu Thr Glu Ala
             420                 425                 430
Gln Met Asp Glu Met Phe Asp Lys Leu Glu Lys Ala Leu Asp Lys Val
             435                 440                 445
Phe Ala Glu Val Ala
    450
```

<210> SEQ ID NO 101
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 101

```
atgaacaaac cgcagagctg ggaaacgcgt gcggaaacct atagcctgta tgcctttacc      60
cacatgccga gcctacatca gcgtgg

```
                65                  70                  75                  80
Gly Tyr His Ala Phe Tyr Gly Ala Met Ser Asp Gln Thr Val Met Leu
                    85                  90                  95

Ser Glu Lys Leu Val Glu Val Ser Pro Phe Asp Ser Gly Arg Val Phe
                    100                 105                 110

Tyr Thr Asn Ser Gly Ser Glu Ala Asn Asp Thr Met Val Lys Met Leu
                    115                 120                 125

Trp Phe Leu His Arg Ala Glu Gly Lys Pro Gln Lys Arg Lys Ile Leu
            130                 135                 140

Thr Leu Lys Asn Ala Tyr His Gly Ser Thr Ala Val Ser Ala Ser Met
145                 150                 155                 160

Thr Gly Ile Pro Tyr Asn Ser Ser Phe Gly Leu Pro Leu Pro Gly Phe
                    165                 170                 175

Leu His Leu Thr Cys Pro His Tyr Trp Arg Tyr Gly Glu Glu Gly Glu
                    180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
            210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                    245                 250                 255

Glu Val Ile Cys Gly Phe Gly Arg Thr Gly Asn Thr Trp Gly Cys Val
                    260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                    325                 330                 335

Ile Asp Val Val Met Asn Glu Gly Leu Leu Glu Asn Val Arg Arg Leu
                    340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                    405                 410                 415

Leu Gly Gln Ser Val Val Leu Ala Pro Pro Tyr Ile Leu Thr Glu Ala
                    420                 425                 430

Gln Met Asp Glu Met Phe Asp Lys Leu Glu Lys Ala Leu Asp Lys Val
                435                 440                 445

Phe Ala Asp Val Ala
        450

<210> SEQ ID NO 103
<211> LENGTH: 1362
<212> TYPE: DNA
<213> ORGANISM: Artificial Sequence
```

```
<220> FEATURE:
<223> OTHER INFORMATION: Engineered variant of V. fluvialis transaminase

<400> SEQUENCE: 103 atgaac

```
Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
            130                 135                 140

Thr Leu Lys Asn Ala Tyr His Gly Ser Thr Ala Val Ser Ala Ser Met
145                 150                 155                 160

Thr Gly Leu Pro Tyr Asn Ser Ser Phe Gly Leu Pro Leu Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
            210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
            405                 410                 415

Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 105
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 105
```

```
atgaacaaac cgcagagctg ggaaacgcgt gcggaaacct atagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattaccc cgccaaaagg ctatttttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gatttttggg     900
ccggaactga gcaaacgtct ggaaaccgcg attgaagcga atgaggaatt tgatcatggt     960
tttaccacag gcgccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct gtgggtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 106  
<211> LENGTH: 453  
<212> TYPE: PRT  
<213> ORGANISM: Artificial Sequence  
<220> FEATURE:  
<223> OTHER INFORMATION: Engineered variant of V. fluvialis transaminase

<400> SEQUENCE: 106

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125
```

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 107
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 107
atgaacaaac cgcagagctg ggaaacgcgt gcggaaacct atagcctgta tgcctttacc    60
cacatgccga gcctacatca gcgtggcacc tcagtggtaa cccatggcga aggcccgtat   120
atcgtggatg tgcatggccg tcgttatctg gatgcgaaca gcggcctgtt caacatggtg   180

```
gcgggctttg atcataaagg cctgattgat gcggcgaaag cgcagtatga acgttttccg      240
ggctatcatg cgttttacgg ccgtatgagc gatcagaccg tgatgctgtc tgaaaaactg      300
gtggaagtga gcccgtttga tagcggccgt gtgttttata ccaacagcgg cagcgaagcg      360
aacgatacca tggtgaaaat gctgtggttt ctgcatcgtg cggaaggcaa accgcagaaa      420
cgtaaaattc tgaccctgaa gaacgcgtat catggctcca ccgcggtgag cgcgagcatg      480
accggccttc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga accattcag aaggaaggcg cggataccat tgcgggcttt       660
tttgcggaac cggtgatggg tgcgggcggt gttattaccc cgccaaaagg ctattttcag      720
gcgattctga ccatcctgcg caaatatgat attccggtga tcagcgatga agtgatttgc      780
ggctttggtc gtaccggcaa cacctggggc tgcgtgacct atgatttac cccggatgcg       840 attattagca gtaaaaacct aaccgcgggt ttttttccag taggagcggt gatttttgggg     900 ccggaactga gcaaacgtct ggaaaccgcg attgaagcga tcgaagaatt tgatcatggt      960
tttaccacag cgccgcatcc ggtggggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 108
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 108

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
```

```
            145                 150                 155                 160
        Thr Gly Leu Pro Tyr Asn Ser Val Phe Gly Leu Pro Leu Pro Gly Phe
                        165                 170                 175

Leu His Leu Thr Cys Pro His Tyr Trp Arg Tyr Gly Glu Glu Gly Glu
                        180                 185                 190

Thr Glu Glu Gln Phe Val Ala Arg Leu Ala Arg Glu Leu Glu Glu Thr
                        195                 200                 205

Ile Gln Lys Glu Gly Ala Asp Thr Ile Ala Gly Phe Phe Ala Glu Pro
        210                 215                 220

Val Met Gly Ala Gly Gly Val Ile Thr Pro Pro Lys Gly Tyr Phe Gln
        225                 230                 235                 240

Ala Ile Leu Thr Ile Leu Arg Lys Tyr Asp Ile Pro Val Ile Ser Asp
                        245                 250                 255

Glu Val Ile Cys Gly Phe Gly Arg Thr Gly Asn Thr Trp Gly Cys Val
                        260                 265                 270

Thr Tyr Asp Phe Thr Pro Asp Ala Ile Ile Ser Ser Lys Asn Leu Thr
                        275                 280                 285

Ala Gly Phe Phe Pro Val Gly Ala Val Ile Leu Gly Pro Glu Leu Ser
                        290                 295                 300

Lys Arg Leu Glu Thr Ala Ile Glu Ala Ile Glu Glu Phe Asp His Gly
        305                 310                 315                 320

Phe Thr Thr Gly Gly His Pro Val Gly Cys Ala Ile Ala Leu Lys Ala
                        325                 330                 335

Ile Asp Val Val Met Asn Glu Gly Leu Ala Glu Asn Val Arg Arg Leu
                        340                 345                 350

Ala Pro Arg Phe Glu Glu Arg Leu Lys His Ile Ala Glu Arg Pro Asn
                        355                 360                 365

Ile Gly Glu Tyr Arg Gly Ile Gly Phe Met Trp Ala Leu Glu Val Val
                        370                 375                 380

Lys Asp Lys Ala Ser Lys Ala Pro Phe Asp Gly Asn Leu Ser Val Ser
        385                 390                 395                 400

Glu Arg Ile Ala Asn Thr Cys Thr Asp Leu Gly Leu Ile Cys Arg Pro
                        405                 410                 415

Leu Gly Gln Ser Val Val Leu Ala Pro Pro Tyr Ile Leu Thr Glu Ala
                        420                 425                 430

Gln Met Asp Glu Met Phe Asp Lys Leu Glu Lys Ala Leu Asp Lys Val
                        435                 440                 445

Phe Ala Glu Val Ala
            450

<210> SEQ ID NO 109
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 109

```
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc cgtataacag caagtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctatttcag    720 gcgattctga ccatcctgcg caaatatgat attccggtga tcagcgatga agtgatttgc    780
ggctttggtc gtaccggcaa cacctggggc tgcgtgacct atgatttac cccggatgcg    840 attattagca gtaaaaacct aaccgcgggt ttttttccag taggagcggt gattttgggg    900
ccggaactga gcaaacgtct ggaaaccgcg attgaagcga ttggggaatt tgatcatggt    960
tttaccacag gcggccatcc ggtgggttgt gcgattgcgc tgaaagcgat tgatgtggtg   1020
atgaacgaag gcctgctgga aaacgtgcgt cgtctggccc gcgttttga agaacgtctg   1080 aaacatattg cggaacgtcc gaacattggc gaatatcgtg gtattggctt tatgtgggcg   1140
ctggaagtgg tgaaagataa agcgagcaaa gccccgtttg atggtaacct gtgggtgagc   1200
gaacgtattg cgaacacctg caccgatctg ggactgattt gccgaccgtt gggccagagc   1260
gtggttctgg cgccgccgta cattctgacc gaagcgcaga tggatgaaat gttcgataaa   1320
ctggaaaaag cgctggataa agtgtttgcg gatgtggcgt aa                      1362
```

<210> SEQ ID NO 110
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 110

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Lys Phe Gly Leu Pro Leu Pro Gly Phe
                165                 170                 175
```

```
Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 111
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 111

```
atgaacaaac cgcagagctg ggaaacgcgt gcggaaaccg tgagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
```

```
accggccttc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattaccc cgccaaaagg ctatttcag       720 gcgattctga ccatcctgcg caaatatgat attccggtga tcagcgatga agtgatttgc      780
ggctttggtc gtaccggcaa cacctggggc tgcgtgacct atgatttac cccggatgcg       840 attattagca gtaaaaacct aaccgcgggt tttttccag taggagcggt gattttgggg       900
ccggaactga gcaaacgtct ggaaaccgcg attgaagcga atgaggaatt tgatcatggt      960
tttaccacag gcggccatcc ggtgggttgt gcgattgcgc tgaaagcgat tgatgtggtg     1020
atgaacgaag gctgctgga aaacgtgcgt cgtctggccc gcgttttga agaacgtctg      1080 aaacatattg cggaacgtcc gaacattggc gaatatcgtg gtattggctt tatgtgggcg     1140
ctggaagtgg tgaaagataa agcgagcaaa gccccgtttg atggtaacct ggttgtgagc     1200
gaacgtattg cgaacacctg caccgatctg ggactgattt gccgaccgtt gggccagagc     1260
gtggttctgg cgccgccgta cattctgacc gaagcgcaga tggatgaaat gttcgataaa     1320
ctggaaaaag cgctggataa agtgtttgcg gaagtggcgt aa                        1362

<210> SEQ ID NO 112
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE

```
Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 113
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 113

```
atgaacaaac cgcagagctg ggaaacgcgt gcggaaacct atagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggcatcc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
```

```
ctggcccgtg aactggaaga aaccattcag aaggaaggcg cggataccat tgcgggcttt    660
tttgcggaac cggtgatggg tgcgggcggt gttattaccc cgccaaaagg ctatttcag     720 gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaccgcg attgaagcga ttggggaatt tgatcatggt     960
tttaccacag gcggccatcc ggtgggttgt gcgattgcgc tgaaagcgat tgatgtggtg   1020
atgaacgaag gcctgctgga aaacgtgcgt cgtctggccc gcgttttga agaacgtctg    1080 aaacatattg cggaacgtcc gaacattggc gaatatcgtg gtattggctt tatgtgggcg   1140
ctggaagtgg tgaaagataa agcgagcaaa gccccgtttg atgg

```
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Leu Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 115
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 115

```
atgaacaaac cgcagagctg ggaaacgcgt gcggaaacct atagcctgta tgcctttacc     60
cacatgccga gcctacatca gcgtggcacc tcagtggtaa cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaattg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
```

```
ggctttggtc gtaccggcaa cacctggggc tgcgtgacct atgatttac cccggatgcg      840 attattagca gtaaaaacct aaccgcgggt ttttttccag taggagcggt gatttgggg      900 ccggaactga gcaaacgtct ggaaaccgcg attgaagcga ttggggaatt tgatcatggt     960
tttaccacag gcggccatcc ggtgggttgt gcgattgcgc tgaaagcgat tgatgtggtg    1020
atgaacgaag gcctgctgga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gatgtggcgt aa                       1362
```

<210> SEQ ID NO 116
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 116

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 117
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 117

| | | | | | |
|---|---|---|---|---|---|
| atgaacaaac | cgcagagctg | ggaaacgcgt | gcggaaacct | atagcctgta | tgcctttacc | 60 |
| cacatgccga | gcctacatca | gcgtggcacc | tcagtggtaa | cccatggcga | aggcccgtat | 120 |
| atcgtggatg | tgcatggccg | tcgttatctg | gatgcgaaca | gcggcctgtt | caacatggtg | 180 |
| gcaggctttg | atcataaagg | cctgattgat | gcggcgaaag | cgcagtatga | acgttttccg | 240 |
| ggctatcatg | cgttttacgg | ccgtatgagc | gatcagaccg | tgatgctgtc | tgaaaaactg | 300 |
| gtggaagtga | gcccgtttga | tagcggccgt | gtgtttata | ccaacagcgg | cagcgaagcg | 360 |
| aacgatacca | tggtgaaaat | gctgtggttt | ctgcatcgtg | cggaaggcaa | accgcagaaa | 420 |
| cgtaaaattc | tgaccctgaa | gaacgcgtat | catggctcca | ccgcggtgag | cgcgagcatg | 480 |
| accggcatcc | gtataacag | cgtgtttggc | ctgccgctgc | cgggctttct | gcatctgacc | 540 |
| tgcccgcatt | attggcgtta | tggcgaagaa | ggcgaaaccg | aagaacagtt | tgtcgcgcgt | 600 |
| ctggcccgtg | aactggaaga | aaccattcag | aaggaaggcg | cggataccat | tgcgggcttt | 660 |
| tttgcggaac | cggtgatggg | tgcgggcggt | gttattaccc | cgccaaaagg | ctatttttcag | 720 |
| gcgattctga | ccatcctgcg | caaatatgat | attccggtga | tcagcgatga | agtgatttgc | 780 |
| ggctttggtc | gtaccggcaa | cacctggggc | tgcgtgacct | atgattttac | cccggatgcg | 840 |
| attattagca | gtaaaaacct | aaccgcgggt | ttttttccag | taggagcggt | gattttgggg | 900 |

-continued

```
ccggaactga gcaaacgtct ggaaaccgcg attgaagcga ttggggaatt tgatcatggt      960
tttaccacag gcggccatcc ggtgggttgt gcgattgcgc tgaaagcgat tgatgtggtg     1020
atgaacgaag gcctgctgga aacgtgcgt cgtctggccc gcgttttga agaacgtctg      1080 aaacatattg cggaacgtcc gaacattggc gaatatcgtg gtattggctt tatgtgggcg     1140
ctggaagtgg tgaaagataa agcgagcaaa gccccgtttg atggtaacct gtgggtgagc     1200
gaacgtattg cgaacacctg caccgatctg ggactgattt gccgaccgtt gggccagagc     1260
gtggttctgg cgccgccgta cattctgacc gaagcgcaga tggatgaaat gttcgataaa     1320
ctggaaaaag cgctggataa agtgtttgcg gatgtggcgt aa                        1362
```

<210> SEQ ID NO 118
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 118

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr

```
Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450

<210> SEQ ID NO 119
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 119
atgaacaaac cgcagagctg ggaaacgcgt gcggaaacct atagcctgta tgcctttacc     60
cacatgccga gcctacatca gcgtggcacc tcagtggtaa cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcatcc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga ttggggaatt tgatcatggt    960
tttaccacag gcggccatcc ggtgggttgt gcgattgcgc tgaaagcgat tgatgtggtg   1020
atgaacgaag gcctgctgga aaacgtgcgt cgtctggccc cgcgttttga agaacgtctg   1080
```

```
aaacatattg cggaacgtcc gaacattggc gaatatcgtg gtattggctt tatgtgggcg   1140
ctggaagtgg tgaaagataa agcgagcaaa gccccgtttg atggtaacct ggttgtgagc   1200
gaacgtattg cgaacacctg caccgatctg ggactgattt gccgaccgtt gggccagagc   1260
gtggttctgg cgccgccgta cattctgacc gaagcgcaga tggatgaaat gttcgataaa   1320
ctggaaaaag cgctggataa agtgtttgcg gaagtggcgt aa                      1362
```

<210> SEQ ID NO 120
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 120

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
```

```
                305                 310                 315                 320
            Phe Thr Thr Gly Gly His Pro Val Gly Cys Ala Ile Ala Leu Lys Ala
                            325                 330                 335
            Ile Asp Val Val Met Asn Glu Gly Leu Leu Glu Asn Val Arg Arg Leu
                            340                 345                 350
            Ala Pro Arg Phe Glu Glu Arg Leu Lys His Ile Ala Glu Arg Pro Asn
                            355                 360                 365
            Ile Gly Glu Tyr Arg Gly Ile Gly Phe Met Trp Ala Leu Glu Val Val
                            370                 375                 380
            Lys Asp Lys Ala Ser Lys Ala Pro Phe Asp Gly Asn Leu Val Val Ser
            385                 390                 395                 400
            Glu Arg Ile Ala Asn Thr Cys Thr Asp Leu Gly Leu Ile Cys Arg Pro
                            405                 410                 415
            Leu Gly Gln Ser Val Val Leu Ala Pro Pro Tyr Ile Leu Thr Glu Ala
                            420                 425                 430
            Gln Met Asp Glu Met Phe Asp Lys Leu Glu Lys Ala Leu Asp Lys Val
                            435                 440                 445
            Phe Ala Glu Val Ala
                450

<210> SEQ ID NO 121
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 121
atgaacaaac cgcagagctg ggaaacgcgt gcggaaacct atagcctgta tgcctttacc     60
cacatgccga gcctacatca gcgtggcacc atggtggtga cccatggcga aggcccgtat

-continued

```
gaacgtattg cgaacacctg caccgatctg ggactgattt gccgaccgtt gggccagagc    1260
gtggttctgg cgccgccgta cattctgacc gaagcgcaga tggatgaaat gttcgataaa    1320
ctggaaaaag cgctggataa agtgtttgcg gaagtggcgt aa                        1362
```

<210> SEQ ID NO 122
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 122

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val

```
Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Leu Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 123
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 123
atgaacaaac cgcagagctg ggaaacgcgt gcggaaacct atagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag caagtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gatttttgggg    900 ccggaactga gcaaacgtct ggaaaccgcg attgaagcga atggggaatt tgatcatggt     960
tttaccacag gcggccatcc ggtgggttgt gcgattgcgc tgaaagcgat tgatgtggtg    1020
atgaacgaag gcctgctgga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
gaacgtattg cgaacacctg caccgatctg ggactgattt gccgaccgtt gggccagagc    1260
gtggttctgg cgccgccgta cattctgacc gaagcgcaga tggatgaaat gttcgataaa    1320
ctggaaaaag cgctggataa agtgtttgcg gaagtggcgt aa                       1362
```

<210> SEQ ID NO 124
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 124

| | | | | | | | | | | | | | | |
|---|---|---|---|---|---|---|

```
Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 125
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 125
atgaacaaac cgcagagctg ggaaacgcgt gcggaaacct atagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggcatcc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gatttttggg     900
ccggaactga gcaaacgtct ggaaaccgcg attgaagcga ttggggaatt tgatcatggt     960
tttaccacag gcggccatcc ggtgggttgt gcgattgcgc tgaaagcgat tgatgtggtg    1020
atgaacgaag gcctgctgga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
gaacgtattg cgaacacctg caccgatctg ggactgattt gccgaccgtt gggccagagc    1260
gtggttatcg cgccgccgta cattctgacc gaagcgcaga tggatgaaat gttcgataaa    1320
ctggaaaaag cgctggataa agtgtttgcg gaagtggcgt aa                        1362

<210> SEQ ID NO 126
<211> LENGTH: 453
<212> TYPE: PRT
```

<213> ORGANISM: Artificial Sequence
<220> FEATURE:
<223> OTHER INFORMATION: Engineered variant of V. fluvialis transaminase

<400> SEQUENCE: 126

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
```

```
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 127
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 127
atgaacaaac cgcagagctg ggaaacgcgt gcggaaacct atagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga atggggaatt tgatcatggt     960
tttaccacag gcggccatcc ggtgggttgt gcgattgcgc tgaaagcgat tgatgtggtg    1020
atgaacgaag gcctgctgga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggtaacct ggttgtgagc    1200
gaacgtattg cgaacacctg caccgatctg ggactgattt gccgaccgtt gggcagcagc    1260
gtggttctgg cgccgccgta cattctgacc gaagcgcaga tggatgaaat gttcgataaa    1320
ctggaaaaag cgctggataa agtgtttgcg gaagtggcgt aa                       1362

<210> SEQ ID NO 128
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 128
```

-continued

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Asn Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
            370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415
```

```
Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 129
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 129
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggcatcc gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagcg ccaaaaacct aaccgcgggt tttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgggt    1200
gaacgtattg cgaacaccctg caccgatctg ggactgattt gtcgaccgat gggccagaac    1260
gtggttctgg caccgccgta cattctgacc gaagcgcaga tggatgaaat gttcgataaa    1320
ctggaaaaag cgctggataa agtgtttgcg gaagtggcgt aa                        1362

<210> SEQ ID NO 130
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 130

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
```

-continued

```
            20                  25                  30
Val Thr His Gly Glu Gly Pro Tyr Ile Val Asp Val His Gly Arg Arg
        35                  40                  45
Tyr Leu Asp Ala Asn Ser Gly Leu Trp Asn Met Val Ala Gly Phe Asp
    50                  55                  60
His Lys Gly Leu Ile Asp Ala Ala Lys Ala Gln Tyr Glu Arg Phe Pro
65                  70                  75                  80
Gly Tyr His Ala Phe Tyr Gly Arg Met Ser Asp Gln Thr Val Met Leu
                85                  90                  95
Ser Glu Lys Leu Val Glu Val Ser Pro Phe Asp Ser Gly Arg Val Phe
            100                 105                 110
Tyr Thr Asn Ser Gly Ser Glu Ala Asn Asp Thr Met Val Lys Met Leu
        115                 120                 125
Trp Phe Leu His Arg Ala Glu Gly Lys Pro Gln Lys Arg Lys Ile Leu
    130                 135                 140
Thr Leu Lys Asn Ala Tyr His Gly Ser Thr Ala Val Ser Ala Ser Met
145                 150                 155                 160
Thr Gly Ile Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
        195                 200                 205
Ile Gln Lys Glu Gly Ala Asp Thr Ile Ala Gly Phe Phe Ala Glu Pro
    210                 215                 220
Val Met Gly Ala Gly Gly Val Ile Thr Pro Lys Gly Tyr Phe Gln
225                 230                 235                 240
Ala Ile Leu Thr Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ala Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Gly
385                 390                 395                 400
Glu Arg Ile Ala Asn Thr Cys Thr Asp Leu Gly Leu Ile Cys Arg Pro
                405                 410                 415
Met Gly Gln Asn Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
```

Phe Ala Glu Val Ala
    450

<210> SEQ ID NO 131
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 131

```
atgaacaaac cgcagagctg ggaaacgcgt gcggaaaccg tgagcctgta tgcctttacc      60
cacatgccga gcctacatca gcgtggcacc atggtggtaa cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccggctc cgggcttttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt tttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc gcgtttttga agaacgtctg    1080
aaacatattg cggaacgtcc gaacattggc gaatatcgtg gtattggctt tatgtgggcg    1140
ctggaagtgg tgaaagataa agcgagcaaa gcccgtttg atggcaacct gagcgtgggt    1200
gaacgtattg cgaacacctg caccgatctg ggactgattt gtcgaccgct gggccagaac    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 132
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 132

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

```
Tyr Leu Asp Ala Asn Ser Gly Leu Trp Asn Met Val Ala Gly Phe Asp
 50                  55                  60

His Lys Gly Leu Ile Asp Ala Lys Ala Gln Tyr Glu Arg Phe Pro
 65                  70                  75                  80

Gly Tyr His Ala Phe Tyr Gly Arg Met Ser Asp Gln Thr Val Met Leu
                     85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
                115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
                290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Gly Arg Pro Asn
                355                 360                 365

Ile Gly Glu Tyr Arg Gly Ile Gly Phe Met Trp Ala Leu Glu Val Val
                370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Asn Val Val Leu Ala Pro Pro Tyr Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
                450
```

<210> SEQ ID NO 133
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 133

```
atgaacaaac cgcagagctg ggaaacgcgt gcggaaaccg tgagcctgta tgcctttacc      60
cacatgccga gc Gly Tyr His Ala Phe Tyr Gly Arg Met Ser Asp Gln Thr Val Met Leu
            85                  90                  95

Ser Glu Lys Leu Val Glu Val Ser Pro Phe Asp Ser Gly Arg Val Phe
        100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
        210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ala Lys Asn Leu Thr
                275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Val Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Val Pro Pro Tyr Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 135
<211> LENGTH: 1362
<212> TYPE: DNA
<213> ORGANISM: Artificial Sequence
<220> FEATURE:

<223> OTHER INFORMATION: Engineered variant of V. fluvialis transaminase

<400> SEQUENCE: 135

```
atgaacaa

```
                100             105              110
Tyr Thr Asn Ser Gly Ser Glu Ala Asn Asp Thr Met Val Lys Met Leu
            115                 120             125

Trp Phe Leu His Arg Ala Glu Gly Lys Pro Gln Lys Arg Lys Ile Leu
        130                 135             140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
        210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
        370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Met Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 137
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 137
atgaacaaac cgcagagctg ggaaacgcgt gcggaaaccg tgagcctgta tgcctttacc      60
```

```
cacatgccga gcctacgtca gcgtggcacc atggtggtga cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgtttctga ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc gtataacag cgtgtttggc ctgccgctgc cggctttct gcatctgacc        540
tgcccgcatt attggcgtta tggcgaagaa ggcgaaaccg aagaacagtt tgtcgcacgt     600
ctggcccgtg aactggaaga aaccattcag aaggaaggcg cggataccat tgcgggcttt     660
tttgcggaac cggtgatggg tgcgggcggt gttattaccc cgccaaaagg ctatttcag     720
gcgattctga ccatcctgcg caaatatgat attccggtga tcagcgatga agtgatttgc     780
ggctttggtc gtaccggcaa cacctggggc tgcgtgacct atgatttac cccggatgcg     840
attattagcg ccaaaaaacct aaccgcgggt tttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 138
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 138

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125
```

```
Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 139
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 139

```
atgaacaaac cgcagagctg ggaaacgcgt gcggaaaccg tgagcctgta tgcctttacc     60
cacatgccga gcctacgtca gcgtggcacc atggtggtga cccatggcga aggcccgtat    120
atcgtggatg tgcatggccg tcgttatctg gatgcgaaca gcggcctgtg gaacatggtg    180
```

-continued

```
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagcg ccaaaaacct aaccgcgggt tttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc gcgttttga agaacgtctg   1080
aaacatattg cggaacgtcc gaacattggc gaatatcgtg gtattggctt tatgtgggcg   1140
ctggaagccg tgaaagataa agcgagcaaa gccccgtttg atggcaacct gagcgtgggt   1200
gaacgtattg cgaacaccct caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 140
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 140

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160
```

Thr Gly Leu Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Thr Pro Lys Gly Tyr Phe Gln
225                 230                 235                 240

Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 141
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 141
atgaacaaac cgcagagctg ggaaacgcgt gcggaaaccg tgagcctgta tgcctttacc 60
cacatgccga gcctacgtca gcgtggcacc atggtggtga cccatggcga aggcccgtat 120
atcgtggatg tgcatggccg tcgttatctg gatgcgaaca gcggcctgtg gaacatggtg 180
gcgggctttg atcataaagg cctgattgat gcggcgaaag cgcagtatga acgttttccg 240
ggctatcatg cgttttacgg ccgcatgagc gatcagaccg tgatgctgtc tgaaaaactg 300
gtggaagtga gcccgtttga tagcggccgt gtgtttctga ccaacagcgg cagcgaagcg 360

-continued

```
aacgatacca tggtgaaaat gctgtggttt ctgcatcgtg cggaaggcaa accgcagaaa      420
cgtaaaattc tgaccctgaa gaacgcgtat catggctcca ccgcggtgag cgcgagcatg      480
accggccttc cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattaccc cgccaaaagg ctatttcag       720 gcgattctga ccatcctgcg caaatatgat attccggtga tcagcgatga agtgatttgc      780
ggctttggtc gtaccggcaa cacctggggc tgcgtgacct atgattttac cccggatgcg      840
attattagca gtaaaaacct aaccgcgggt ttttttccag taggagcggt gattttgggg      900
ccggaactga gcaaacgtct ggaaccgcg attgaagcga tcgaagaatt tgatcatggt       960
tttaccacag gcggccatcc ggtgggttgt gcgattgcgc tgaaagcgat tgatgtggtg     1020
atgaacgaag gcctggccga aaacgtgcgt cgtctggccc gcgttttga agaacgtctg     1080 aaacatattg cggaacgtcc gaacattggc gaatatcgtg gtattggctt tatgtgggcg     1140
ctggaagccg tgaaagataa agcgagcaaa gccccgtttg atggcaacct gagcgtgagc     1200
gaacgtattg cgaacacctg caccgatctg ggactgattt gccgaccgtt gggccagagc     1260
gtggttctgg tgccgccgta cattctgacc gaagcgcaga tggatgaaat gttcgataaa     1320
ctggaaaaag cgctggataa agtgtttgcg gaagtggcgt aa                        1362
```

<210> SEQ ID NO 142
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 142

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
```

```
              180              185              190
Thr Glu Glu Gln Phe Val Ala Arg Leu Ala Arg Glu Leu Glu Glu Thr
        195                  200                  205
Ile Gln Lys Glu Gly Ala Asp Thr Ile Ala Gly Phe Phe Ala Glu Pro
    210                  215                  220
Val Met Gly Ala Gly Gly Val Ile Thr Pro Pro Lys Gly Tyr Phe Gln
225                  230                  235                  240
Ala Ile Leu Thr Ile Leu Arg Lys Tyr Asp Ile Pro Val Ile Ser Asp
            245                  250                  255
Glu Val Ile Cys Gly Phe Gly Arg Thr Gly Asn Thr Trp Gly Cys Val
                260                  265                  270
Thr Tyr Asp Phe Thr Pro Asp Ala Ile Ile Ser Ser Lys Asn Leu Thr
        275                  280                  285
Ala Gly Phe Phe Pro Val Gly Ala Val Ile Leu Gly Pro Glu Leu Ser
    290                  295                  300
Lys Arg Leu Glu Thr Ala Ile Glu Ala Ile Glu Glu Phe Asp His Gly
305                  310                  315                  320
Phe Thr Thr Gly Gly His Pro Val Gly Cys Ala Ile Ala Leu Lys Ala
            325                  330                  335
Ile Asp Val Val Met Asn Glu Gly Leu Ala Glu Asn Val Arg Arg Leu
                340                  345                  350
Ala Pro Arg Phe Glu Glu Arg Leu Lys His Ile Ala Glu Arg Pro Asn
        355                  360                  365
Ile Gly Glu Tyr Arg Gly Ile Gly Phe Met Trp Ala Leu Glu Ala Val
    370                  375                  380
Lys Asp Lys Ala Ser Lys Ala Pro Phe Asp Gly Asn Leu Ser Val Ser
385                  390                  395                  400
Glu Arg Ile Ala Asn Thr Cys Thr Asp Leu Gly Leu Ile Cys Arg Pro
            405                  410                  415
Leu Gly Gln Ser Val Val Leu Val Pro Pro Tyr Ile Leu Thr Glu Ala
                420                  425                  430
Gln Met Asp Glu Met Phe Asp Lys Leu Glu Lys Ala Leu Asp Lys Val
        435                  440                  445
Phe Ala Glu Val Ala
    450
```

<210> SEQ ID NO 143
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 143

| | | | | | |
|---|---|---|---|---|---|
| atgaacaaac | cgcagagctg | ggaaacgcgt | gcggaaacct | atagcctgta | tgcctttacc | 60 |
| cacatgccga | gcctacatca | gcgtggcacc | atggtggtga | cccatggcga | aggcccgtat | 120 |
| atcgtggatg | tgcatggccg | tcgttatctg | gatgcgaaca | gcggcctgtg | aacatggtg | 180 |
| gcgggctttg | atcataaagg | cctgattgat | gcggcgaaag | cgcagtatga | acgttttccg | 240 |
| ggctatcatg | cgttttacgg | cctgatgagc | gatcagaccc | tgatgctgtc | tgaaaaactg | 300 |
| gtggaagtga | gcccgtttga | tagcggccgt | gtgttttata | ccaacagcgg | cagcgaagcg | 360 |
| aacgatacca | tggtgaaaat | gctgtggttt | ctgcatcgtg | cggaaggcaa | accgcagaaa | 420 |
| cgtaaaattc | tgaccctgaa | gaacgcgtat | catggctcca | ccgcggtgag | cgcgagcatg | 480 |

```
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgatttac cccggatgcg    840 attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt atgtgggcg    1140 ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 144
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 144

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205
```

Ile Gln Lys Glu Gly Ala Asp Thr Ile Ala Gly Phe Ala Glu Pro
    210                 215                 220

Val Met Gly Ala Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 145
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 145
atgaacaaac cgcagagctg ggaaacgcgt gcggaaaccg tgagcctgta tgcctttacc      60
cacatgccga gcctacgtca gcgtggcacc atggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gcaggcgtat catggctcca ccgcggtgag cgcgagcatg     480
accggcatcc cgtataacag cgtgtttggc ctgccgctgc cgggctttct gcatctgacc     540
tgcccgcatt attggcgtta tggcgaagaa ggcgaaaccg aagaacagtt gtcgcgcgt      600 ctggcccgtg aactggaaga aaccattcag aaggaaggcg cggataccat tgcgggcttt     660

-continued

```
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgatttttac cccggatgcg   840 attattagcg ccaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagccg tgaaagataa agcgagcaaa gccccgtttg atggcaacct gagcgtgggt   1200
gaacgtattg cgaacacctg caccgatctg ggactgattt gtcgaccgct gggccagaac   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 146
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 146

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20

```
Ala Ile Leu Thr Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Asn Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 147
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 147
atgaacaaac cgcagagctg ggaaacgcgt gcggaaaccg tgagcctgta tgcctttacc      60
cacatgccga gcctacatca gcgtggcacc atggtgacca cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga cgttttccg    240 ggctatcatg cgttttacgg ccgtatgagc gatcagaccg tgatgctgtc tgaaaaactg    300
gtggaagtga gcccgtttga tagcggccgt gtgtttctga ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcggcggt gttattaccc cgccaaaagg ctatttcag    720 gcgattctga ccatcctgcg caaatatgat attccggtga tcagcgatga agtgatttgc    780
```

-continued

```
ggctttggtc gtaccggcaa cacctggggc tgcgtgacct atgattttac cccggatgcg      840
attattagca gtaaaaacct aaccgcgggt ttttttccag taggagcggt gattttgggg      900
ccggaactga gcaaacgtct ggaaaccgcg attgaagcga tcgaagaatt tgatcatggt      960
tttaccacag gcggccatcc ggtgggttgt gcgattgcgc tgaaagcgat tgatgtggtg     1020
atgaacgaag gcctggccga aaacgtgcgt cgtctggccc cgcgttttga agaacgtctg     1080
aaacatattg cggaacgtcc gaacattggc gaatatcgtg gtattggctt tatgtgggcg     1140
ctggaagtgg tgaaagataa agcgagcaaa gccccgtttg atggcaacct gagcgtgagc     1200
gaacgtattg cgaacacctg caccgatctg ggactgattt gccgaccgtt gggccagagc     1260
gtggttctgg caccgccgta cattctgacc gaagcgcaga tggatgaaat gttcgataaa     1320
ctggaaaaag cgctggataa agtgtttgcg aagtggcgt aa                         1362
```

<210> SEQ ID NO 148
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 148

```
Met Asn Lys Pro Gln Ser Trp Glu Thr Arg Ala Glu Thr Val Ser Leu
1               5                  10                  15

Tyr Ala Phe Thr His Met Pro Ser Leu His Gln Arg Gly Thr Met Val
            20                  25                  30

Thr Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
```

```
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320
Phe Thr Thr Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Val Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Ala Pro Pro Tyr Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 149
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 149
atgaacaaac cgcagagctg ggaaacgcgt gcggaaaccg tgagcctgta tgcctttacc      60
cacatgccga gcctacatca gcgtggcacc atggtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgtttctga ccaacagcgg cagcgaagcg     360
aacgatacca tggtgaaaat gctgtggttt ctgcatcgtg cggaaggcaa accgcagaaa     420
cgtaaaattc tgaccctgaa gcaggcgtat catggctcca ccgcggtgag cgcgagcatg     480
accggcatcc cgtataacag cgtgtttggc ctgccggctc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
```

-continued

```
tttaccacag cggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagccg tgaaagataa agcgagcaaa gccccgtttg atggcaacct gagcgtgggt    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                      1362
```

<210> SEQ ID NO 150
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 150

```
Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

```
Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 151
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 151

```
atgaacaaac cgcagagctg ggaaacgcgt gcggaaacct atagcctgta tgcctttacc        60
cacatgccga gcctacatca gcgtggcacc atggtggtga cccatggcga aggcccgtat       120
atcgtggatg tgcatggccg tcgttatctg gatgcgaaca gcggcctgtt caacatggtg       180
gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatcgtg cggaaggcaa accgcagaaa       420
cgtaaaattc tgaccctgaa aacgcgtat catggctcca ccgcggtgag cgcgagcatg       480
accggccttc cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactggaaga aaccattcag aaggaaggcg cggataccat tgcgggcttt       660
tttgcggaac cggtgatggg tgcggcggt gttattaccc cgccaaaagg ctattttcag       720
gcgattctga ccatcctgcg caaatatgat attccggtga tcagcgatga agtgatttgc       780
ggctttggtc gtaccggcaa cacctggggc tgcgtgacct atgatttac cccggatgcg       840
attattagca gtaaaaacct aaccgcgggt tttttttccag taggagcggt gattttgggg       900
ccggaactga gcaaacgtct ggaaaccgcg attgaagcga tcgaagaatt tgatcatggt       960
tttaccacag cggccatcc ggtgggttgt gcgattgcgc tgaaagcgat tgatgtggtg      1020
atgaacgaag gcctggccga aaacgtgcgt cgtctggccc cgcgttttga agaacgtctg      1080
```

```
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

\<210\> SEQ ID NO 152
\<211\> LENGTH: 453
\<212\> TYPE: PRT
\<213\> ORGANISM: Artificial Sequence
\<220\> FEATURE:
\<223\> OTHER INFORMATION: Engineered variant of V. fluvialis transaminase

\<400\> SEQUENCE: 152

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320
```

```
Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Arg Leu Lys His Ile Ala Glu Arg Pro Asn
        355                 360                 365

Ile Gly Glu Tyr Arg Gly Ile Gly Phe Met Trp Ala Leu Glu Val Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 153
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 153

```
atgaacaaac cgcagagctg ggaaacgcgt gcggaaaccg tgagcctgta tgcctttacc      60
cacatgccga gctacgtca gcgtggcacc atggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgtttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc gtataacag cgtgtttggc ctgccgctgc gggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattaccc cgccaaaagg ctatttcag     720
gcgattctga ccatcctgcg caaatatgat attccggtga tcagcgatga agtgatttgc     780
ggctttggtc gtaccggcaa cacctgggc tgcgtgacct atgatttac cccggatgcg     840
attattagcg ccaaaaacct aaccgcgggt ttttttccag taggagcggt gattttgggg     900
ccggaactga gcaaacgtct ggaaaccgcg attgaagcga tcgaagaatt tgatcatggt     960
tttaccacac acggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gcccgtttg atggcaacct gagcgtgggt    1200
gaacgtattg cgaacacctg caccgatctg ggactgattt gccgaccgtt gggccagagc    1260
```

```
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 154
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 154

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
```

-continued

```
                340                 345                 350
Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
        370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
                420                 425                 430

Gln Met Asp Glu Met Phe Asp Lys Leu Glu Lys Ala Leu Asp Lys Val
        435                 440                 445

Phe Ala Glu Val Ala
        450
```